Figure 1:
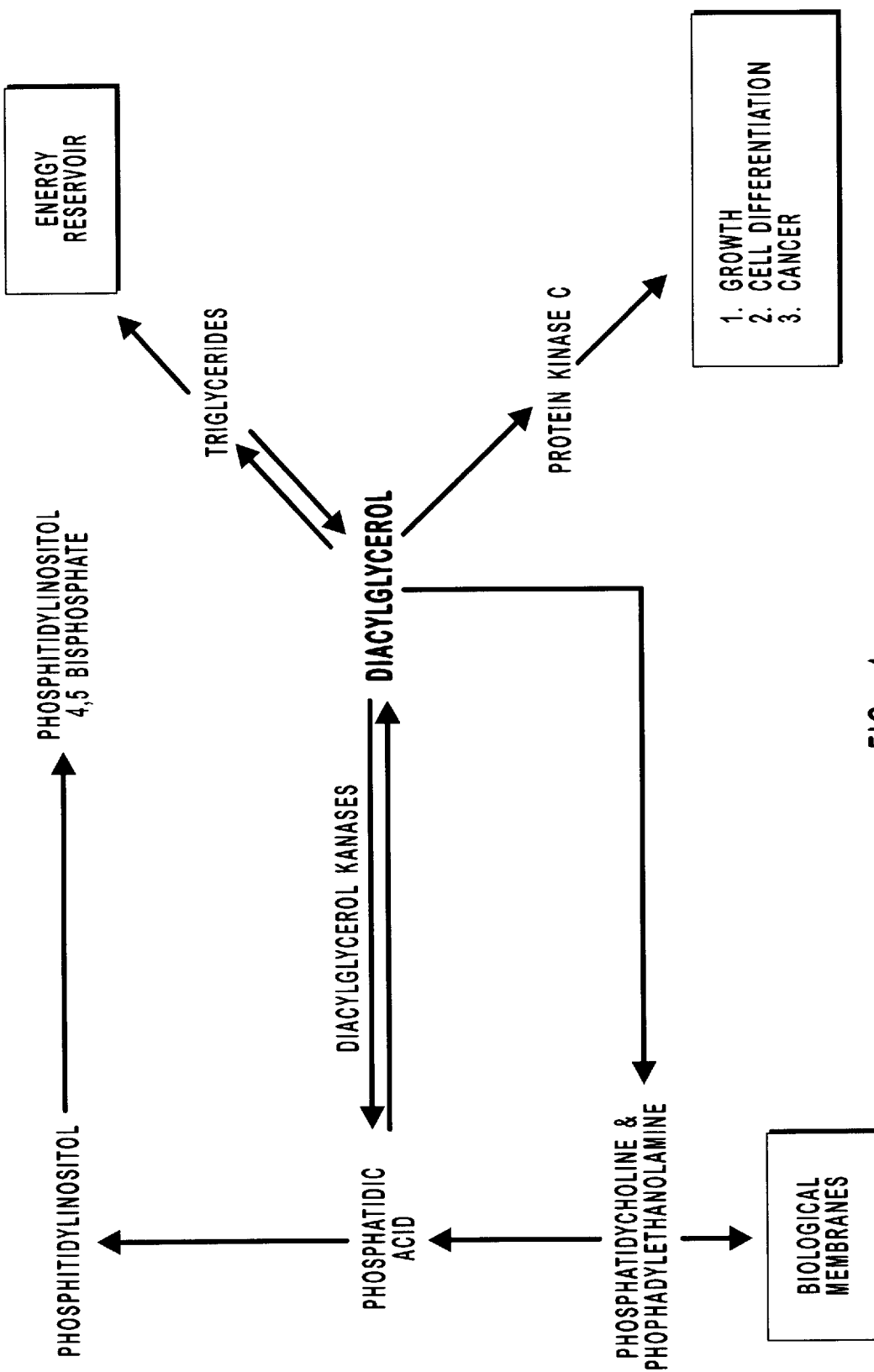

United States Patent [19]
Prescott et al.

[11] Patent Number: 5,976,875
[45] Date of Patent: Nov. 2, 1999

[54] DIACYLGLYCEROL KINASE ISOFORMS EPSILON AND ZETA AND METHODS OF USE THEREOF

[75] Inventors: Stephen M. Prescott; Michaeline Bunting; Wen Tang; Matthew Topham, all of Salt Lake City, Utah

[73] Assignee: University of Utah, Salt Lake City, Utah

[21] Appl. No.: 08/841,483

[22] Filed: Apr. 22, 1997

Related U.S. Application Data

[60] Provisional application No. 60/016,210, Apr. 22, 1996.
[51] Int. Cl.$^6$ .............................. C12N 1/20; C07H 21/04
[52] U.S. Cl. ............... 435/325; 435/252.3; 435/252.33; 435/135; 435/320.1; 435/194; 536/23.1; 536/23.2; 536/23.5
[58] Field of Search ..................... 435/193, 194, 435/320.1, 325, 252.3, 135, 370; 536/23.2, 23.1, 23.5

[56] References Cited

PUBLICATIONS

"Cloning and Characterization of a Glucocorticoid–induced Diacylglycerol Kinase", Klauck et ala., *The Journal of Biological Chemistry*, vol. 271, No. 33, Aug. 16, 1996, pp. 19781–19788.
"Nucleocytoplasmic Transport", Görlich et al., *Science*, vol. 271, Mar. 15, 1996, pp. 1513–1518.
"The C–terminal Part of Diacylglycerol Kinase α Lacking Zinc Fingers Serves as a Catalytic Domain", Sakane et al., *Biochem Journal*, 318, 1996, pp. 583–590.
"Structural Studies on the PH Domains of Db., Sosl, IRS–1, and βARK1 and Their Differential Binding to $G_{\beta\gamma}$ Subunits", Mahadeven et al., *Biochemistry*, 1995, 34, pp. 9111–9117.
"Arachidonoyl–Diacylglycerol Kinase", Walsh et al., *The Journal of Biological Chemistry*, vol. 270, No. 48, Dec. 1, 1995, pp. 27647–28653.
"Two Distinct Raf Domains Mediate Interaction with Ras", Brtva et al., *The Journal of Biological Chemistry*, vol. 270, No. 17, Apr. 28, 1995, pp. 9809–9812.
"Role for Ceramide in Cell Cycle Arrest", Jayadev et al., *The Journal of Biological Chemistry*, vol. 270, No. 5, Feb. 2, 1995, pp. 2047–2052.
"Attenuation of Ceramide–Induced Apoptosis by Diglyceride in Human Myeloid Leukemia Cells", Jarvis et al., *The Journal of Biological Chemistry*, vol. 269, No. 50, Dec. 16, 1994, pp. 31685–31692.
"Binding of G Protein βγ–Subunits to Pleckstrin Homology Domains", Touhara et al., *The Journal of Biological Chemistry*, vol. 269, No. 14, Apr. 8, 1994, pp. 10217–10220.
"The Sphingomyelin Cycle and the Second Messenger Function of Ceramide", Hannun, *The Journal of Biological Chemistry*, vol. 269, No. 5, Feb. 4, 1994, pp. 3125–3128.
"Normal and Oncogenic $p21^{ras}$ Proteins Bind to the Amino–Terminal Regulatory Domain of c–Raf–1", Zhang et al., *Nature*, vol. 364, Jul. 22, 1993, pp. 308–313.
"The MARCKS Family of Cellular Protein Kinase C Substrates", Blackshear, *The Journal of Biological Chemistry*, vol. 268, No. 3, Jan. 25, 1993, pp. 1501–1504.
"Phosphatidic Acid is a Specific Activator of Phosphatidylinositol–4–Phosphate Kinase", Moritz et al., *The Journal of Biological Chemistry*, vol. 267, No. 11, Apr. 15, 1992, pp. 7207–7210.
Kai, M., *J.Biol.Chem.* 269:18492–18498 (1994).
Sakane, F. et al. *Nature* 344:345–348 (1990).

*Primary Examiner*—Dian C. Jocobson
*Assistant Examiner*—Nashaat T. Nasheel
*Attorney, Agent, or Firm*—Madson & Metcalf

[57] ABSTRACT

Two novel diacylglycerol kinase (DGK) isoforms are disclosed. The cDNA of one DGK isoform, designated DGKε, is about 2.6 kb in length. The DGKε cDNA has an open reading frame encoding 567 amino acids and has a predicted molecular mass of 63 kDA. DAG kinase ε is highly selective for arachidonate-containing diacylglycerol (DAG) substrates. The cDNA of the second isoform, designated DGK ζ, is 3.5 kb in length. The DGKζ cDNA contains a single large open reading frame encoding a 928-amino acid protein with a predicted molecular mass of 103.9 kDa. An alternatively spliced muscle specific species of DGK ζ, DGKζ-2 is also disclosed and characterized. DGKζ is localized to the nucleus. A lysine-rich region with homology to the MARCKS protein is shown to be necessary and sufficient to confer nuclear localization to DGKζ via a protein kinase C phosphorylation.

15 Claims, 23 Drawing Sheets

1 kb

DGKE1
DGKE2
DGKE3
DGKE13

FIG. 2A

GP3
-87 gcgtcgttctcctcctgcgcgaggcggccaaggcctgctggtccggagccgcgcctccacccgcgcgaggtatcgtccttggagaag 1 atggaagcggagaggcggccggcgccgggctcgccctccgagggcctgtttgcggacgggcacctgatcttgtggacgctgtgctcggtcctgctgccggtgttcatcaccttctggtgt
1 M E A E R R R P A P G S P S E G L F A D G H L I L W T L C S V L L P V F I T F W C 121 agcctccagcggtcgcgccggcagctgcaccgcagggacatcttccgcaagagcaagcacggtggcgcgacacggacctgttcagccagcccaccactactgctgcgtgtgcgcgcagcac
41 S L Q R S R R Q L H R R D I F R K S K H G W R D T D L F S Q P T Y C C V C A Q H 241 attctgcagggcgccttctgcgactgctgcgggctccgcgtggacgagggctgcctcaggaaggccgacaagcgcttccagtgcaaggagattatgctcaagaatgacaccaaggtcctg
81 I L Q G A F C D C C G L R V D E G C L R K A D K R F Q C K E I M L K N D T K V L 361 gacgccatgccccaccactggatccggggcaacgtgccccctgtgcagttactgtatggtttgcaagcagcagtgtggctgtcaacccaagctttgcgattacaggtgcatttggtgccag
121 D A M P H H W I R G N V P L C S Y C M V C K Q Q C G C Q P K L C D Y R C I W C Q 481 aaaacagtacatgatgagtgcatgaaaaatagttcaaagaatgaaaaatgtgattttggagaattcaaaaacctaatcattccaccaagttatttaacatccattaatcagatgcgtaaa
161 K T V H D E C M K N S L K N E K C D F G E F K N L I I P P S Y L T S I N Q M R K 601 gacaaaaaaacagattatgaagtgctagcctctaagcttggaaagcagtggaccccattaataatcctggccaactctcgtagtggaactaatatgggagaaggactgttgggagaattt
201 D K K T D Y E V L A S K L G K Q W T P L I I L A N S R S G T N M G E G L L G E F GP1
721 aggatcttgttgaatccagtccaggtttttgatgtaactaaaactcctcctatcaaagccctacaactctgtactcttctcccatattattcagctcgagtacttgtttgtggagggat
241 R I L L N P V Q V F D V T K T P P I K A L Q L C T L L P Y Y S A R V L V C G G D 841 gggactgtagggtgggtcctggatgcagttgatgacatgaagattaagggacaagaaaagtacattccacaagttgcagttttgcctctgggaacaggcaacgatctatccaatacattg
281 G T V G W V L D A V D D M K I K G Q E K Y I P Q V A V L P L G T G N D L S N T L 961 ggttggggtacaggttatgctggagaaattccagttgcgcaggttttgcgaaatgtaatggaagcagatggaattaaactagatcgatggaaagttcaagtaacaaataaaggatactac
321 G W G T G Y A G E I P V A Q V L R N V M E A D G I K L D R W K V Q V T N K G Y Y 1081 aacttaagaaaacccaaggaattcacaatgaacaactattttctgttggacctgatgctctcatggctctcaattttcatgctcatcgtgaaggccaccatctctgttttctagcaga
361 N L R K P K E F T M N N Y F S V G P D A L M A L N F H A H R E K A P S L F S S R 1201 attcttaataaggcggttacttattctatggaaccaaagattgttagtgcaagaatgtaaagatttgaataaaaaagttgagctagaactggatggtgagcgagtagcactgccagc
401 I L N K A V Y L F Y G T K D C L V Q E C K D L N K K V E L E L D G E R V A L P S 1321 ttggaaggtattatagttctgaacatcggatactgggcggttggctgcagactatgggaaggdatgggggacgagacttaccctctagccaggcatgacgatggtctgctggaagtcgtt
441 L E G I I V L N I G Y W G G G C R L W E G M G D E T Y P L A R H D D G L L E V V 1441 ggagtatatggtctttccactgtgctcagattcaagtaaaactggctaatcctttcgaataggacaggcacatacagtgaggctgattttgaagtgctccatgatgccaatgcaggtg
481 G V Y G S P H C A Q I Q V K L A N P F R I G Q A H T V R L I L K C S M N P M Q V GP2
1561 gatggggagccttgggcccaagggccctgcactgtcaccataactcacaagacacatgcaatgatgttatattctctggagaacaaacagatgatgacatctctagtacttcggatcaa
521 D G E P W A Q G P C T V T I T H K T H A M M L Y F S G E Q T D D D I S S T S D Q GP4
1681 gaagatataaaggcgactgaatagatggatgaggggagtgaaaactttgcatagaatcctcacgcaagtagatacatgttcatccaaaagtattaatagaaattctctatcagctattcag
561 E D I K A T E *

1801 tcttaatttcactagtagtataatgggtatacatttttgtaaatagcatcccaaaccagccagccttcagttatttacaaatgtttgtcctttttcagcaaaatacttcaaatgaata
1921 gtattaacttacaaaaagtcacgaaaaacttacatgagagtgaaaatttgttatgactgttttgagagtggggactcactctgaagtatgtgctgtctcatgtcttattttgaaccatgc
2041 atatgatggacacacaatggatggacacattatatctccaacaaggtgtgggtggaaagatcaaattaacctgctctttgaaatgattactgtcaaaccagcatgttaattgtgagca
2161 tcctctgcagcatgcccctaagattttctacaacccaaaccaagtgtatgtattgattctaggaaccccccaaaaggagaatagtaaaaaaagatcatacttaaaatttgtattacaat
2281 ttttattttaggaacttattcagacacgtaaatgttgttaattctgtaggtaaccatttgagctgcaattcaggatcttttttataacaccagtgtagccaaaagagaaacagataagt
2401 gaattggtaagaaataagattcagacacttgggattgtaagttataggttctgagctgaactgtttatc

FIG. 2B

```
                                     GCGGCGCGGAGCGGGCGTGCTGAGCCCC         28
     GGCCGCCGGCCCGGCATGGGCGTCTCCCGCGGGCCCTCCGCCGGCCGGGGCGTAGGGCCGG          88

ATGGAGCGCGGGACGGTAGCCCCGAGGCCCGGAGCAGCGACTCCGAGTCGGCTTCCGCC          148
  1  M  E  P  R  D  G  S  P  E  A  R  S  S  D  S  E  S  A  S  A

TCGTCCAGCGGCTCCGAGCGCGACGCCGGTCCCGAGCCGGACAAGGCGCGCGGCGACTC           208
 21  S  S  S  G  S  E  R  D  A  G  P  E  P  D  K  A  P  R  R  L

AACAAGCGGCGCTTCCCGGGGCTGCGGCTCTTCGGGCACAGGAAAGCCATCACCAAGTCG          268
 41  N  K  R  R  F  P  G  L  R  L  F  G  H  R  K  A  I  T  K  S

GGGCCTCCAGCACCTGGCCCCCCCTCCGCCCACCCCTGGGGCCCCGTGCAGCGAGTCAGAG        328
 61  G  L  Q  H  L  A  P  P  P  P  T  P  G  A  P  C  S  E  S  E

CGGCAGATCCGGAGTACAGTGGACTGGAGCGAGTCAGCGACATATGGGGAGCACATCTGG        388
 81  R  Q  I  R  S  T  V  D  W  S  E  S  A  T  Y  G  E  H  I  W

TTCGAGACCAACGTGTCCGGGGACTTCTGCTACGTTGGGGAGCAGTACTGTGTAGCCAGG        448
101  F  E  T  N  V  S  G  D  F  C  Y  V  G  E  Q  Y  C  V  A  R

ATGCTGAAGTCAGTGTCTCGAAGAAAGTGCGCAGCCTGCAAGATTGTGGTGCACACGCCC        508
121  M  L  K  S  V  S  R  R  K  C  A  A  C  K  I  V  V  H  T  P

TGCATCGAGCAGCTGGAGAAGATAAATTTCCGCTGTAAGCCGTCCTTCCGTGAATCAGGC        568
141  C  I  E  Q  L  E  K  I  N  F  R  C  K  P  S  F  R  E  S  G

TCCAGGAATGTCCGCGAGCCAACCTTTGTACGGCACCACTGGGTACACAGACGACGCCAG        628
161  S  R  N  V  R  E  P  T  F  V  R  H  H  W  V  H  R  R  R  Q

GACGGCAAGTGTCGGCACTGTGGGAAGGGATTCCAGCAGAAGTTCACCTTCCACAGCAAG        688
181  D  G  K  C  R  H  C  G  K  G  F  Q  Q  K  F  T  F  H  S  K

GAGATTGTGGCCATCAGCTGCTCGTGGTGCAAGCAGGCATACCACAGCAAGGTGTCCTGC        748
201  E  I  V  A  I  S  C  S  W  C  K  Q  A  Y  H  S  K  V  S  C

TTCATGCTGCAGCAGATCGAGGAGCCGTGCTCGCTGGGGGTTCCACGCAGCCGTGGTCATC        808
221  F  M  L  Q  Q  I  E  E  P  C  S  L  G  V  H  A  A  V  V  I

CCGCCCACCTGGATCCTCCGCGCCCGAGGCCCCAGAATACTCTGAAAGCAAGCAAGAAG        868
241  P  P  T  W  I  L  R  A  R  R  P  Q  N  T  L  K  A  S  K  K

AAGAAGAGGGCATCCTTCAAGAGGAAGTCCAGCAAGAAAGGGCCTGAGGAGGGCCGCTGG        928
261  K  K  R  A  S  F  K  R  K  S  S  K  E  G  P  E  E  G  R  W

AGACCCTTCATCATCAGGCCCACCCCCTCCCCGCTCATGAAGCCCCTGCTGGTGTTTGTG        988
281  R  P  F  I  I  R  P  T  P  S  P  L  M  K  P  L  L  V  F  V

AACCCCAAGAGTGGGGGCAACCAGGGTGCAAAGATCATCCAGTCTTTCCTCTGGTATCTC       1048
301  N  P  K  S  G  G  N  Q  G  A  K  I  I  Q  S  F  L  W  Y  L

AATCCCCGACAAGTCTTCGAGCTCAGCGAGGGGCCCAAGGAGGCGCTGGAGATGTAC        1108
321  N  P  R  Q  V  F  D  L  S  Q  G  G  P  K  E  A  L  E  M  Y

CGCAAAGTGCACAACCTGCGGATCCTGGCGTGCGGGGGCGACGGCACGGTGGGCTGGATC     1168
341  R  K  V  H  N  L  R  I  L  A  C  G  D  G  T  V  G  W  I

CTCTCCACCCTGGACCAGCTACGCCTGAAGCCGCACCCCCTGTTGCCATCCTCGCCCCTG     1228
361  L  S  T  L  D  Q  L  R  L  K  P  P  P  P  V  A  I  L  P  L

GGTACTGCAACGACTTGGCCCGAACCCTCAACTGGGGTGGGGGCTACACAGATGAGCCT       1288
381  G  T  G  N  D  L  A  R  T  L  N  W  G  G  G  Y  T  D  R  P

GTGTCCAAGATCCTCTCCCACGTGGAGGAGGGGAACGTGGTACAGCTGGACCGCTGGGAC      1348
401  V  S  K  I  L  S  H  V  E  E  G  N  V  V  Q  L  D  R  W  D

CTCCACGCTGAGCCCAACCCCGAGGCAGGGCCTGAGGACCGAGATGAAGGCGCCACCGAC      1408
421  L  H  A  E  P  N  P  E  A  G  P  E  D  R  D  E  G  A  T  D

CGGTTGCCCCTGGATGTCTTCAACAACTACTTCAGCCTGGGCTTTGACGCCCACGTCACC      1468
441  R  L  P  L  D  V  F  N  N  Y  F  S  L  G  F  D  A  H  V  T

CTGGAGTTCCACGAGTCTCGAGAGGCCAACCCAGAGAAATTCAACAGCCGCTTCCGGAAT     1528
461  L  E  F  H  E  S  R  E  A  N  P  E  K  F  N  S  R  F  R  N

AAGATGTTCTACGCCGGGACAGCTTTCTCTGACTTCCTGATGGGCAGCTCCAAGGACCTG     1588
481  K  M  F  Y  A  G  T  A  F  S  D  F  L  M  G  S  S  K  D  L

GCCAAGCACATCCGAGTGGTGTGTGATGGAATGGACTTGACTCCCAAGATCCAGGACCTG     1648
501  A  K  H  I  R  V  V  C  D  G  M  D  L  T  P  K  I  Q  D  L

AAACCCCAGTGTGTTGTTTTCCTGAACATCCCCAGGTACTGTGCGGGCACCATGCCCTGG     1708
521  K  P  Q  C  V  V  F  L  N  I  P  R  Y  C  A  G  T  M  P  W

GGCCACCCTGGGGAGCACCACGACTTTGAGCCCAGCGGCATGACGACGGCTACCTCGAG      1768
541  G  H  P  G  E  H  H  D  F  E  P  Q  R  H  D  D  G  Y  L  E

GTCATTGGCTTCACCATGACGTCGTTGGCCGCGCTGCAGGTGGGCGGACACGGCGAGCGG     1828
561  V  I  G  F  T  M  T  S  L  A  A  L  Q  V  G  G  H  G  E  R

CTGACGCAGTGTCGCGAGGTGGTGCTCACCACATCCAAGGCCATCCCGGTGCAGGTGGAT     1888
581  L  T  Q  C  R  E  V  V  L  T  T  S  K  A  I  P  V  Q  V  D

GGCGAGCCCTGCAAGCTTGCAGCCTCACGCATCCGCATCGCCTTGCGCAACCAGGCCACC    1948
601  G  E  P  C  K  L  A  A  S  R  I  R  I  A  L  R  N  Q  A  T

ATGGTGCAGAAGGCCAAGCGGCGGAGCGCCGCCCCCCTGCACAGCGACCAGCAGCCGGTG    2008
621  M  V  Q  K  A  K  R  R  S  A  A  P  L  H  S  D  Q  Q  P  V

CCAGAGCAGTTGCGCATCCAGGTGAGTCGCGTCAGCATGCACGACTATGAGGCCCTGCAC     2068
641  P  E  Q  L  R  I  Q  V  S  R  V  S  M  H  D  Y  E  A  L  H
```

```
     TACGACAAGGAGCAGCTCAAGGAGGCCTCTGTCCGCTGGGCACTGTGGTGGTCCCAGGA      2128
661  Y  D  K  E  Q  L  K  E  A  S  V  P  L  G  T  V  V  V  P  G

GACAGTGACCTAGAGCTCTGCCGTGCCCACATTGAGAGACTCCAGCAGGAGCCCGATGGT    2188
681  D  S  D  L  E  L  C  R  A  H  I  E  R  L  Q  Q  E  P  D  G

GCTGGAGCCAAGTCCCCGACATGCCAGAAACTGTCCCCCAAGTGGTGCTTCCTGGACGCC    2248
701  A  G  A  K  S  P  T  C  Q  K  L  S  P  K  W  C  F  L  D  A

ACCACTGCCAGCCGCTTCTACAGGATCGACCGAGCCCAGGAGCACCTCAACTATGTGACT    2308
721  T  T  A  S  R  F  Y  R  I  D  R  A  Q  E  H  L  N  Y  V  T

GAGATCGCACAGGATGAGATTTATATCCTGGACCCTGAGCTGCTGGGGCATCGGCCCGG    2368
741  E  I  A  Q  D  E  I  Y  I  L  D  P  E  L  L  G  A  S  A  R

CCTGACCTCCCAACCCCCACTTCCCCTCTCCCCACCTCACCCTGCTCACCCACGCCCCGG    2428
761  P  D  L  P  T  P  T  S  P  L  P  T  S  P  C  S  P  T  P  R

TCACTGCAAGGGGATGCTGCACCCCCTCAAGGTGAAGAGCTGATTGAGGCTGCCAAGAGG    2488
781  S  L  Q  G  D  A  A  P  P  Q  G  E  E  L  I  E  A  A  K  R

AACGACTTCTGTAAGCTCCAGGAGCTGCACCGAGCTGGGGCGGACCTCATGCACCGGGAC    2548
801  N  D  F  C  K  L  Q  E  L  H  R  A  G  G  D  L  M  H  R  D

GAGCAGAGTCGCACGCTCCTGCACCACGCAGTCAGCACTGGCAGCAAGGATGTGGTCCGC    2608
821  E  Q  S  R  T  L  L  H  H  A  V  S  T  G  S  K  D  V  V  R

TACCTGCTGGACCACGCCCCCCCAGAGATCCTTGATGCGGTGGAGGAAAACGGGGAGACC    2668
841  Y  L  L  D  H  A  P  P  E  I  L  D  A  V  E  E  N  G  E  T

TGTTTGCACCAAGCAGCGGCCCTGGGCCAGCGCACCATCTGCCACTACATCGTGGAGGCC    2728
861  C  L  H  Q  A  A  A  L  G  Q  R  T  I  C  H  Y  I  V  E  A

GGGGCCTCGCTCATGAAGACAGACCAGCAGGGCGACACTCCCCGGCAGCGGGCTGAGAAG    2788
881  G  A  S  L  M  K  T  D  Q  Q  G  D  T  P  R  Q  R  A  E  K

GCTCAGGACACCGAGCTGGCCGCCTACCTGGAGAACCGGCAGCACTACCAGATGATCCAG    2848
901  A  Q  D  T  E  L  A  A  Y  L  E  N  R  Q  H  Y  Q  M  I  Q

CGGGAGGACCAGGAGACGGCTGTGTAGCGGGCCGCCCACGGGCAGCAGGAGGGACAATGC    2906
921  R  E  D  Q  E  T  A  V  (928 aa)

GGCCAGGGGACGAGCGCCTTCCTTGCCCACCTCACTGCCACATTCCAGTGGGACGGCCAC    2968
     GGGGGGACCTAGGCCCCAGGGAAAGAGCCCCATGCCGCCCCCTAAGGAGCCGCCCAGACC    3028
     TAGGGCTGGACTCAGGAGCTGGGGGGGGCCTCACCTGTTCCCCTGAGGACCCCGCCGGACC    3088
     CGGAGGCTCACAGGGAACAAGACACGGCTGGGTTGGATATGCCTTTGCCGGGGTTCTGGG    3148
     GCAGGCGCTCCCTGGCCGCAGCAGATGCCCTCCCAGGAGTGGAGGGGCTGGAGAGGGGG    3208
     AGGCCTTCGGGAAGAGGCTTCCTGGGCCCCCTGGTCTTCGGCCGGGTCCCCAGCCCCCGC    3268
     TCCTGCCCCACCCCACCTTCCTCCGGGCTTCCTCCCGGAAACTCAGCGCCTGCTGCACTTG    3328
     CCTGCCCTGCCTTGCTTGGCACCCGCTCCGGCGACCCTCCCCGCTCCCCTGTCATTTCAT    3388
     CGCGGACTGTGCGGCCTGGGGGTGGGGGGCGGGACTCTCACGGTGACATGTTTACAGCTG    3448
     GGTGTGACTCAGTAAAGTGGATTTTTTTTCTTTAAAAAAA (3490 bp)
```

FIG. 5A

```
Ankyrin        -G-TPLH-AA--GH---V--LL--GA--N----
                            A            D
hDGKζ repeat1  -----L--AA-------L--L---G--------
hDGKζ repeat2  ---T-LH-AV--G----V--LL-----------
hDGKζ repeat3  -G-T-LH-AA--G-------IV--GA-------
hDGKζ repeat4  -G-TP---A---------A--L-----------
```

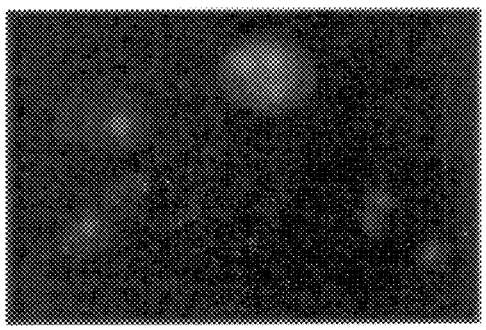
RRPQNTLKASKKKKRASFKRKSSKKGP
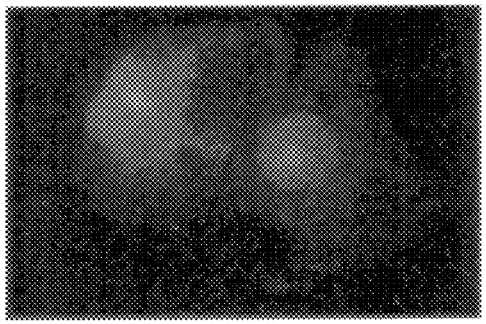
AAPQNTLKASKKKKRASFKRKSSKKGP
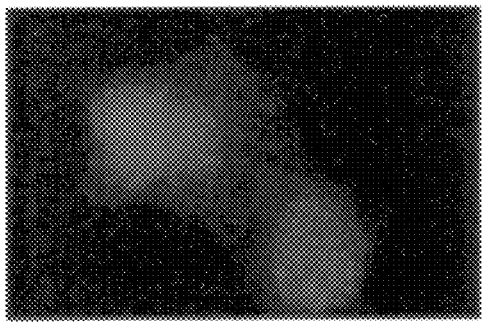
RRPQNTLAASAAAAASFKRKSSKKGP
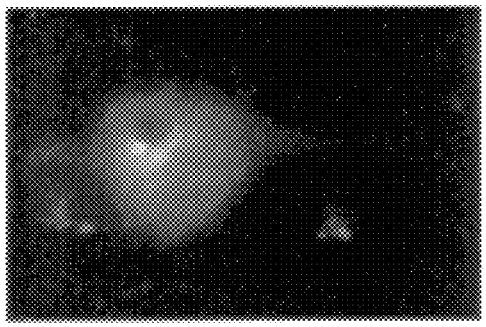
RRPQNTLKASKKKKRASFAAASSAAGP
FIG. 14

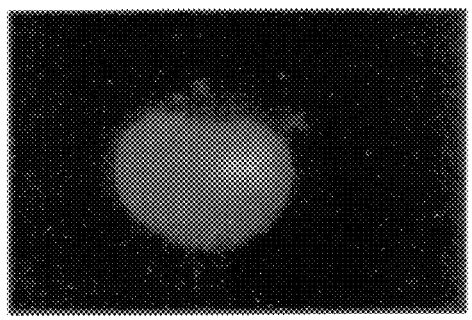
RRPQNTLKASKKKKRASFKRKSSKKGP
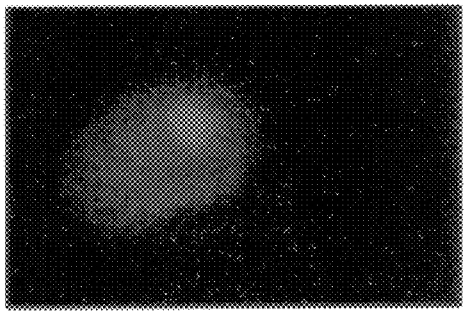
RRPQNTLKAAKKKKRAAFKRKAAKKGP
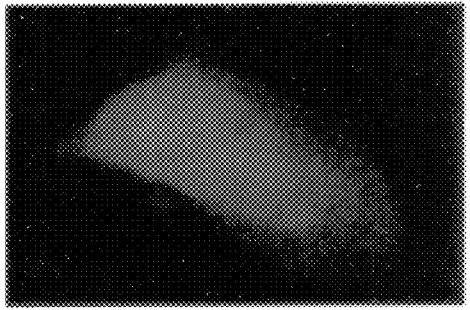
RRPQNTLKADKKKKRADFKRKDDKKGP
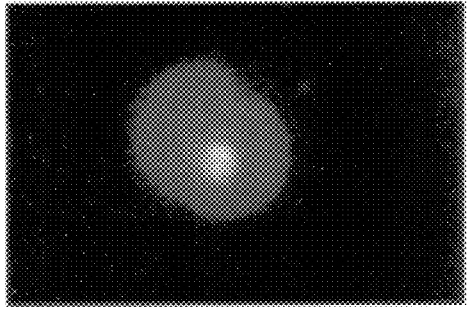
RRPQNTLKANKKKKRANFKRKNNKKGP
FIG. 16

Subdomain 1 (C4-a)

```
C. elegans DGK      442 PLLVLVNPKSGGKQGVKILQNFEYLLNPRQVYDISKTGE--EEGTQLFSTLRNGNILVCG 499
Drosophile DGK2     809 PVTVFINPKSGGKQGNQGHKLLGKYQHILMPRQVFDILTQGGE--INGIDMFRKAPNDRVLACG 866
Porcine DGKα        375 PLLVFVNPKSGGKQGERVLMFQYLLNPRQVENILKDGE--EEGIRFTREVPDYNRILVCG 432
Rat DGKβ            435 PLLVFVNPKSGGKQGERIYRNFQYLLNPRQVYSISGNGE--MEGDHFFRDVPDERVLACG 492
Human DGKγ          434 PLLVLVNPKSGGKQGRQGERILRNFHYLLNPRQVFNIDNGGE--TEGENFFRDTPDERVLVCG 491
Human DGKδ          277 PLLVFVNSKSGDNQCVKFLRETQLLNPRQVFDLDNGGE--EHGURLFQKFUTBRILVCG 334
Human DGKε          219 PLIILANSRSGTNMKEGLLGEFRILLLNFVQVFDVKTPEIKALQILCTILLPYYSARVLVCG 278
Human DGKζ          295 PLLVFVNPKSGGNQGAKIIQSETLHYLNFRQVFDISCGGE--KDAIEHYNRVEMIRILACG 352
Hamster DGKη        326 PLLVFVNSIKSGDNQGVKFLREFKQLALNPADVFDLMNGGE--HLGTRLFQKFDMERILVCE 383
Consensus              PLLVFVNPKSGGNQG....L..F..LLNPRQVFDL...GP......GL..F........R.LVCG
```

```
C. elegans DGK      500 GDGTIGAVLESMDRNTTPHGR----PRVAVLPLGTGNDLARCLMWGGGTDEN--LNKTIDQ 556
Drosophile DGK2     867 GDGTVGAVLSVLDQIQPFLQPA--PANGVLPLGTGNDLARCLMGGGGTDEP--IGKIXE 924
Porcine DGKα        433 GDGTVGWILETIDKANLPF-V---PEVAVLPLGTGNDLARCLMWGGGTEGGN--LGKTLDD 488
Rat DGKβ            493 GDGTVGWILDCIEKANVVK-H---PEVAILPLGTGNDLARCLMWGGGTEGGT--LNGKILD 548
Human DGKγ          492 GDGTVGWILDCIEKANFAK-H---PEVAVLPLGTGNDLARCLMWGGGTEGGS--LTKILD 547
Human DGKδ          335 GDGSVGWVLSEIDSLNLHKQC---QLGVLPLGTGNDLARVLGWGSAODDDTCLPQIKK 390
Human DGKε          279 GDGTVGWVLDAVDDMKIKGQEKYIPQVAVLPLGTGNDLSHTLWGGTGPAGEIPRAQVTRM 338
Human DGKζ          353 GDGTVGWIILSTLDQIR---LKPP---PRVAILPLGTGNDLARTLNWGGYTDEP--VSKIISK 407
Hamster DGKη        384 GDGSVGAVLSEIDCLNLNKQC---QLGVLPLGTGNDLARVLGWGGSDDDTCLROIEK 440
Consensus              GDG.VGAVL..ID.............P..VAVLPLGTGNDLAR..L..WGGGY.....L..IL...
```

```
C. elegans DGK      557 IEKSSLIDMDRMQIKIEI 574
Drosophile DGK2     925 IGMSQCVLHDRMQRVRVTP 942
Porcine DGKα        489 LERASKYVRMDRMSVEVIP 506
Rat DGKβ            549 IESSTEIMLDRMKFEVTP 566
Human DGKγ          548 IEQSPLVVQLDRMRILEVIP 565
Human DGKδ          391 LERASTNQLDRMSVNAYE 408
Human DGKε          339 VMEADGIKLDRMQKVQVTN 356
Human DGKζ          408 VEEGNVVQLDRMQLHAEP 425
Hamster DGKη        441 LERASTNQLDRMSIMTYE 458
Consensus              IE........LDRM.........
```

FIG. 22A

FIG. 22B

SEQUENCE LISTING

```
<160> NUMBER OF SEQ ID NOS: 33

<210> SEQ ID NO 1
<211> LENGTH: 2562
<212> TYPE: DNA
<213> ORGANISM: Homo sapiens
<220> FEATURE:
<221> NAME/KEY: CDS
<222> LOCATION: (88)..(1791)
<300> PUBLICATION INFORMATION:
<303> JOURNAL: J. Biol. Chem.
<304> VOLUME: 271
<305> ISSUE: 17
<306> PAGES: 10237-10241
<307> DATE: 1996-04-26

<400> SEQUENCE: 1
gcgtcgttct cctcctgcgc gaggcggcca aggcctgctg gtccggagcc gcgcctccac      60
ccgcgcgagg tatcgtcctt ggagaag atg gaa gcg gag agg cgg ccg gcg ccg     114
                              Met Glu Ala Glu Arg Arg Pro Ala Pro
                                1               5 ggc tcg ccc tcc gag ggc ctg ttt gcg gac ggg cac ctg atc ttg tgg       162
Gly Ser Pro Ser Glu Gly Leu Phe Ala Asp Gly His Leu Ile Leu Trp
 10              15                  20                  25 acg ctg tgc tcg gtc ctg ctg ccg gtg ttc atc acc ttc tgg tgt agc       210
Thr Leu Cys Ser Val Leu Leu Pro Val Phe Ile Thr Phe Trp Cys Ser
                 30                  35                  40 ctc cag cgg tcg cgc cgg cag ctg cac cgc agg gac atc ttc cgc aag       258
Leu Gln Arg Ser Arg Arg Gln Leu His Arg Arg Asp Ile Phe Arg Lys
             45                  50                  55 agc aag cac ggg tgg cgc gac acg gac ctg ttc agc cag ccc acc tac       306
Ser Lys His Gly Trp Arg Asp Thr Asp Leu Phe Ser Gln Pro Thr Tyr
         60                  65                  70 tgc tgc gtg tgc gcg cag cac att ctg cag ggc gcc ttc tgc gac tgc       354
Cys Cys Val Cys Ala Gln His Ile Leu Gln Gly Ala Phe Cys Asp Cys
     75                  80                  85 tgc ggg ctc cgc gtg gac gag ggc tgc ctc agg aag gcc gac aag cgc       402
Cys Gly Leu Arg Val Asp Glu Gly Cys Leu Arg Lys Ala Asp Lys Arg
 90                  95                 100                 105 ttc cag tgc aag gag att atg ctc aag aat gac acc aag gtc ctg gac       450
Phe Gln Cys Lys Glu Ile Met Leu Lys Asn Asp Thr Lys Val Leu Asp
                110                 115                 120 gcc atg ccc cac cac tgg atc cgg ggc aac gtg ccc ctg tgc agt tac       498
Ala Met Pro His His Trp Ile Arg Gly Asn Val Pro Leu Cys Ser Tyr
            125                 130                 135 tgt atg gtt tgc aag cag cag tgt ggc tgt caa ccc aag ctt tgc gat       546
Cys Met Val Cys Lys Gln Gln Cys Gly Cys Gln Pro Lys Leu Cys Asp
        140                 145                 150 tac agg tgc att tgg tgc cag aaa aca gta cat gat gag tgc atg aaa       594
Tyr Arg Cys Ile Trp Cys Gln Lys Thr Val His Asp Glu Cys Met Lys
    155                 160                 165 aat agt tta aag aat gaa aaa tgt gat ttt gga gaa ttc aaa aac cta       642
```

-continued

| | | |
|---|---|---|
| Asn Ser Leu Lys Asn Glu Lys Cys Asp Phe Gly Glu Phe Lys Asn Leu
170             175                 180                 185 | | |
| atc att cca cca agt tat tta aca tcc att aat cag atg cgt aaa gac
Ile Ile Pro Pro Ser Tyr Leu Thr Ser Ile Asn Gln Met Arg Lys Asp
            190                 195                 200 | 690 | |
| aaa aaa aca gat tat gaa gtg cta gcc tct aag ctt gga aag cag tgg
Lys Lys Thr Asp Tyr Glu Val Leu Ala Ser Lys Leu Gly Lys Gln Trp
        205                 210                 215 | 738 | |
| acc cca tta ata atc ctg gcc aac tct cgt agt gga act aat atg gga
Thr Pro Leu Ile Ile Leu Ala Asn Ser Arg Ser Gly Thr Asn Met Gly
            220                 225                 230 | 786 | |
| gaa gga ctg ttg gga gaa ttt agg atc ttg ttg aat cca gtc cag gtt
Glu Gly Leu Leu Gly Glu Phe Arg Ile Leu Leu Asn Pro Val Gln Val
    235                 240                 245 | 834 | |
| ttt gat gta act aaa act cct cct atc aaa gcc cta caa ctc tgt act
Phe Asp Val Thr Lys Thr Pro Pro Ile Lys Ala Leu Gln Leu Cys Thr
250                 255                 260                 265 | 882 | |
| ctt ctc cca tat tat tca gct cga gta ctt gtt tgt gga ggg gat ggg
Leu Leu Pro Tyr Tyr Ser Ala Arg Val Leu Val Cys Gly Gly Asp Gly
                270                 275                 280 | 930 | |
| act gta ggg tgg gtc ctg gat gca gtt gat gac atg aag att aag gga
Thr Val Gly Trp Val Leu Asp Ala Val Asp Asp Met Lys Ile Lys Gly
            285                 290                 295 | 978 | |
| caa gaa aag tac att cca caa gtt gca gtt ttg cct ctg gga aca ggc
Gln Glu Lys Tyr Ile Pro Gln Val Ala Val Leu Pro Leu Gly Thr Gly
        300                 305                 310 | 1026 | |
| aac gat cta tcc aat aca ttg ggt tgg ggt aca ggt tat gct gga gaa
Asn Asp Leu Ser Asn Thr Leu Gly Trp Gly Thr Gly Tyr Ala Gly Glu
            315                 320                 325 | 1074 | |
| att cca gtt gcg cag gtt ttg cga aat gta atg gaa gca gat gga att
Ile Pro Val Ala Gln Val Leu Arg Asn Val Met Glu Ala Asp Gly Ile
330                 335                 340                 345 | 1122 | |
| aaa cta gat cga tgg aaa gtt caa gta aca aat aaa gga tac tac aac
Lys Leu Asp Arg Trp Lys Val Gln Val Thr Asn Lys Gly Tyr Tyr Asn
                350                 355                 360 | 1170 | |
| tta aga aaa ccc aag gaa ttc aca atg aac aac tat ttt tct gtt gga
Leu Arg Lys Pro Lys Glu Phe Thr Met Asn Asn Tyr Phe Ser Val Gly
            365                 370                 375 | 1218 | |
| cct gat gct ctc atg gct ctc aat ttt cat gct cat cgt gag aag gca
Pro Asp Ala Leu Met Ala Leu Asn Phe His Ala His Arg Glu Lys Ala
        380                 385                 390 | 1266 | |
| cca tct ctg ttt tct agc aga att ctt aat aag gcg gtt tac tta ttc
Pro Ser Leu Phe Ser Ser Arg Ile Leu Asn Lys Ala Val Tyr Leu Phe
        395                 400                 405 | 1314 | |
| tat gga acc aaa gat tgt tta gtg caa gaa tgt aaa gat ttg aat aaa
Tyr Gly Thr Lys Asp Cys Leu Val Gln Glu Cys Lys Asp Leu Asn Lys
410                 415                 420                 425 | 1362 | |
| aaa gtt gag cta gaa ctg gat ggt gag cga gta gca ctg ccc agc ttg
Lys Val Glu Leu Glu Leu Asp Gly Glu Arg Val Ala Leu Pro Ser Leu
            430                 435                 440 | 1410 | |
| gaa ggt att ata gtt ctg aac atc gga tac tgg ggc ggt ggc tgc aga
Glu Gly Ile Ile Val Leu Asn Ile Gly Tyr Trp Gly Gly Gly Cys Arg
        445                 450                 455 | 1458 | |
| cta tgg gaa ggg atg ggg gac gag act tac cct cta gcc agg cat gac
Leu Trp Glu Gly Met Gly Asp Glu Thr Tyr Pro Leu Ala Arg His Asp
        460                 465                 470 | 1506 | |
| gat ggt ctg ctg gaa gtc gtt gga gta tat ggg tct ttc cac tgt gct
Asp Gly Leu Leu Glu Val Val Gly Val Tyr Gly Ser Phe His Cys Ala
475                 480                 485 | 1554 | |
| cag att caa gta aaa ctg gct aat cct ttt cga ata gga cag gca cat
 | 1602 | |

-continued

```
Gln Ile Gln Val Lys Leu Ala Asn Pro Phe Arg Ile Gly Gln Ala His
490                 495                 500                 505 aca gtg agg ctg att ttg aag tgc tcc atg atg cca atg cag gtg gat    1650
Thr Val Arg Leu Ile Leu Lys Cys Ser Met Met Pro Met Gln Val Asp
                    510                 515                 520 ggg gag cct tgg gcc caa ggg ccc tgc act gtc acc ata act cac aag    1698
Gly Glu Pro Trp Ala Gln Gly Pro Cys Thr Val Thr Ile Thr His Lys
                525                 530                 535 aca cat gca atg atg tta tat ttc tct gga gaa caa aca gat gat gac    1746
Thr His Ala Met Met Leu Tyr Phe Ser Gly Glu Gln Thr Asp Asp Asp
            540                 545                 550 atc tct agt act tcg gat caa gaa gat ata aag gcg act gaa tag        1791
Ile Ser Ser Thr Ser Asp Gln Glu Asp Ile Lys Ala Thr Glu
            555                 560                 565 atggatgagg gagtgaaaac tttgcataga atcctcacgc aagtagatac atgttcatcc  1851
aaaagtatta atagaaattc tctatcagct attcagtctt aatttcacta gtagtataat  1911
gggtatacat ttttgtaaat agcatcccca aaccagccag ccttcagtta tttacaaatg  1971
tttgtccttt tttcagcaaa atacttcaaa tgaatagtat taacttacaa aaagtcacga  2031
aaaacttaca tgagagtgaa aatttgttat gactgttttg agagtgggac tcactctgaa  2091
gtatgtgctg tctcatgtct tatttttgaa ccatgcatat gatggacaca caatggatgg  2151
acacattata tctccaacaa ggtgtgggtg gaaagatcaa attaacctgc ttttttgaaa  2211
ggaaatgatt actgtcaaac cagcatggtt aattgtgagc atcctctgca gcatgcccct  2271
taagattttc tacaacccaa accaagtgta tgtattgatt tctaggaacc cccaaaagga  2331
gaatagtaaa aaaagatcat acttaaaatt tgtattacaa ttttttatttt aggaacttat  2391 tcagacacgt aaatgttgtt taattctgta ggtaaccatt tgagctgcaa ttcaggatct  2451
tttttataac accagtgtag ccaaaagaga aacagataag tgaattggta agaaataaga  2511
ttcagagcac ttgggattgt aagttatagg ttctgagctg aactgtttat c           2562
```

<210> SEQ ID NO 2
<211> LENGTH: 567
<212> TYPE: PRT
<213> ORGANISM: Homo sapiens

<400> SEQUENCE: 2

```
Met Glu Ala Glu Arg Arg Pro Ala Pro Gly Ser Pro Ser Glu Gly Leu
1               5                   10                  15

Phe Ala Asp Gly His Leu Ile Leu Trp Thr Leu Cys Ser Val Leu Leu
                20                  25                  30

Pro Val Phe Ile Thr Phe Trp Cys Ser Leu Gln Arg Ser Arg Arg Gln
            35                  40                  45

Leu His Arg Arg Asp Ile Phe Arg Lys Ser Lys His Gly Trp Arg Asp
        50                  55                  60

Thr Asp Leu Phe Ser Gln Pro Thr Tyr Cys Cys Val Cys Ala Gln His
65                  70                  75                  80

Ile Leu Gln Gly Ala Phe Cys Asp Cys Cys Gly Leu Arg Val Asp Glu
                85                  90                  95

Gly Cys Leu Arg Lys Ala Asp Lys Arg Phe Gln Cys Lys Glu Ile Met
                100                 105                 110

Leu Lys Asn Asp Thr Lys Val Leu Asp Ala Met Pro His His Trp Ile
        115                 120                 125

Arg Gly Asn Val Pro Leu Cys Ser Tyr Cys Met Val Cys Lys Gln Gln
    130                 135                 140
```

-continued

| | | | | | | | | | | | | | | | |
|---|---|---|---|---|---|---|---|---|---|---|---|---|---|---|---|
|Cys|Gly|Cys|Gln|Pro|Lys|Leu|Cys|Asp|Tyr|Arg|Cys|Ile|Trp|Cys|Gln|
|145| | | | |150| | | |155| | | | |160| |

Lys Thr Val His Asp Glu Cys Met Lys Asn Ser Leu Lys Asn Glu Lys
                165             170             175

Cys Asp Phe Gly Glu Phe Lys Asn Leu Ile Ile Pro Ser Tyr Leu
            180             185             190

Thr Ser Ile Asn Gln Met Arg Lys Asp Lys Lys Thr Asp Tyr Glu Val
        195             200             205

Leu Ala Ser Lys Leu Gly Lys Gln Trp Thr Pro Leu Ile Ile Leu Ala
    210             215             220

Asn Ser Arg Ser Gly Thr Asn Met Gly Glu Gly Leu Leu Gly Glu Phe
225             230             235             240

Arg Ile Leu Leu Asn Pro Val Gln Val Phe Asp Val Thr Lys Thr Pro
                245             250             255

Pro Ile Lys Ala Leu Gln Leu Cys Thr Leu Leu Pro Tyr Tyr Ser Ala
            260             265             270

Arg Val Leu Val Cys Gly Gly Asp Gly Thr Val Gly Trp Val Leu Asp
        275             280             285

Ala Val Asp Asp Met Lys Ile Lys Gly Gln Glu Lys Tyr Ile Pro Gln
    290             295             300

Val Ala Val Leu Pro Leu Gly Thr Gly Asn Asp Leu Ser Asn Thr Leu
305             310             315             320

Gly Trp Gly Thr Gly Tyr Ala Gly Glu Ile Pro Val Ala Gln Val Leu
                325             330             335

Arg Asn Val Met Glu Ala Asp Gly Ile Lys Leu Asp Arg Trp Lys Val
            340             345             350

Gln Val Thr Asn Lys Gly Tyr Tyr Asn Leu Arg Lys Pro Lys Glu Phe
        355             360             365

Thr Met Asn Asn Tyr Phe Ser Val Gly Pro Asp Ala Leu Met Ala Leu
    370             375             380

Asn Phe His Ala His Arg Glu Lys Ala Pro Ser Leu Phe Ser Ser Arg
385             390             395             400

Ile Leu Asn Lys Ala Val Tyr Leu Phe Tyr Gly Thr Lys Asp Cys Leu
                405             410             415

Val Gln Glu Cys Lys Asp Leu Asn Lys Lys Val Glu Leu Glu Leu Asp
            420             425             430

Gly Glu Arg Val Ala Leu Pro Ser Leu Glu Gly Ile Ile Val Leu Asn
        435             440             445

Ile Gly Tyr Trp Gly Gly Gly Cys Arg Leu Trp Glu Gly Met Gly Asp
    450             455             460

Glu Thr Tyr Pro Leu Ala Arg His Asp Asp Gly Leu Leu Glu Val Val
465             470             475             480

Gly Val Tyr Gly Ser Phe His Cys Ala Gln Ile Gln Val Lys Leu Ala
                485             490             495

Asn Pro Phe Arg Ile Gly Gln Ala His Thr Val Arg Leu Ile Leu Lys
            500             505             510

Cys Ser Met Met Pro Met Gln Val Asp Gly Glu Pro Trp Ala Gln Gly
        515             520             525

Pro Cys Thr Val Thr Ile Thr His Lys Thr His Ala Met Met Leu Tyr
    530             535             540

Phe Ser Gly Glu Gln Thr Asp Asp Ile Ser Ser Thr Ser Asp Gln
545             550             555             560

Glu Asp Ile Lys Ala Thr Glu
            565

```
<210> SEQ ID NO 3
<211> LENGTH: 3490
<212> TYPE: DNA
<213> ORGANISM: Homo sapiens
<220> FEATURE:
<221> NAME/KEY: CDS
<222> LOCATION: (89)..(2875)

<400> SEQUENCE: 3
gcggcgcgga gcgggcgtgc tgagccccgg ccgccggccc ggcatgggcg tctcccgcgg      60
gccctccgcc ggccggggct agggccgg atg gag ccg cgg gac ggt agc ccc       112
                              Met Glu Pro Arg Asp Gly Ser Pro
                                1               5 gag gcc cgg agc agc gac tcc gag tcg gct tcc gcc tcg tcc agc ggc      160
Glu Ala Arg Ser Ser Asp Ser Glu Ser Ala Ser Ala Ser Ser Ser Gly
         10                  15                  20 tcc gag cgc gac gcc ggt ccc gag ccg gac aag gcg ccg cgg cga ctc      208
Ser Glu Arg Asp Ala Gly Pro Glu Pro Asp Lys Ala Pro Arg Arg Leu
 25                  30                  35                  40 aac aag cgg cgc ttc ccg ggg ctg cgg ctc ttc ggg cac agg aaa gcc      256
Asn Lys Arg Arg Phe Pro Gly Leu Arg Leu Phe Gly His Arg Lys Ala
                 45                  50                  55 atc acc aag tcg ggc ctc cag cac ctg gcc ccc cct ccg ccc acc cct      304
Ile Thr Lys Ser Gly Leu Gln His Leu Ala Pro Pro Pro Pro Thr Pro
             60                  65                  70 ggg gcc ccg tgc agc gag tca gag cgg cag atc cgg agt aca gtg gac      352
Gly Ala Pro Cys Ser Glu Ser Glu Arg Gln Ile Arg Ser Thr Val Asp
         75                  80                  85 tgg agc gag tca gcg aca tat ggg gag cac atc tgg ttc gag acc aac      400
Trp Ser Glu Ser Ala Thr Tyr Gly Glu His Ile Trp Phe Glu Thr Asn
 90                  95                 100 gtg tcc ggg gac ttc tgc tac gtt ggg gag cag tac tgt gta gcc agg      448
Val Ser Gly Asp Phe Cys Tyr Val Gly Glu Gln Tyr Cys Val Ala Arg
105                 110                 115                 120 atg ctg aag tca gtg tct cga aga aag tgc gca gcc tgc aag att gtg      496
Met Leu Lys Ser Val Ser Arg Arg Lys Cys Ala Ala Cys Lys Ile Val
                125                 130                 135 gtg cac acg ccc tgc atc gag cag ctg gag aag ata aat ttc cgc tgt      544
Val His Thr Pro Cys Ile Glu Gln Leu Glu Lys Ile Asn Phe Arg Cys
            140                 145                 150 aag ccg tcc ttc cgt gaa tca ggc tcc agg aat gtc cgc gag cca acc      592
Lys Pro Ser Phe Arg Glu Ser Gly Ser Arg Asn Val Arg Glu Pro Thr
                155                 160                 165 ttt gta cgg cac cac tgg gta cac aga cga cgc cag gac ggc aag tgt      640
Phe Val Arg His His Trp Val His Arg Arg Arg Gln Asp Gly Lys Cys
            170                 175                 180 cgg cac tgt ggg aag gga ttc cag cag aag ttc acc ttc cac agc aag      688
Arg His Cys Gly Lys Gly Phe Gln Gln Lys Phe Thr Phe His Ser Lys
185                 190                 195                 200 gag att gtg gcc atc agc tgc tcg tgg tgc aag cag gca tac cac agc      736
Glu Ile Val Ala Ile Ser Cys Ser Trp Cys Lys Gln Ala Tyr His Ser
                205                 210                 215 aag gtg tcc tgc ttc atg ctg cag cag atc gag gag ccg tgc tcg ctg      784
Lys Val Ser Cys Phe Met Leu Gln Gln Ile Glu Glu Pro Cys Ser Leu
            220                 225                 230 ggg gtc cac gca gcc gtg gtc atc ccg ccc acc tgg atc ctc cgc gcc      832
Gly Val His Ala Ala Val Val Ile Pro Pro Thr Trp Ile Leu Arg Ala
        235                 240                 245 cgg agg ccc cag aat act ctg aaa gca agc aag aag aag aag agg gca      880
Arg Arg Pro Gln Asn Thr Leu Lys Ala Ser Lys Lys Lys Lys Arg Ala
```

-continued

|  |  |  |  |  |  |  |  |  |  |  |  |  |  |  |  |
|---|---|---|---|---|---|---|---|---|---|---|---|---|---|---|---|
|  |  | 250 |  |  |  | 255 |  |  |  | 260 |  |  |  |  |  |
| tcc | ttc | aag | agg | aag | tcc | agc | aag | aaa | ggg | cct | gag | gag | ggc | cgc | tgg | 928 |
| Ser | Phe | Lys | Arg | Lys | Ser | Ser | Lys | Lys | Gly | Pro | Glu | Glu | Gly | Arg | Trp |  |
| 265 |  |  |  | 270 |  |  |  | 275 |  |  |  | 280 |  |  |  |  |

| aga | ccc | ttc | atc | atc | agg | ccc | acc | ccc | tcc | ccg | ctc | atg | aag | ccc | ctg | 976 |
| Arg | Pro | Phe | Ile | Ile | Arg | Pro | Thr | Pro | Ser | Pro | Leu | Met | Lys | Pro | Leu |  |
|  |  |  |  | 285 |  |  |  | 290 |  |  |  | 295 |  |  |  |  |

| ctg | gtg | ttt | gtg | aac | ccc | aag | agt | ggg | ggc | aac | cag | ggt | gca | aag | atc | 1024 |
| Leu | Val | Phe | Val | Asn | Pro | Lys | Ser | Gly | Gly | Asn | Gln | Gly | Ala | Lys | Ile |  |
|  |  |  | 300 |  |  |  | 305 |  |  |  | 310 |  |  |  |  |  |

| atc | cag | tct | ttc | ctc | tgg | tat | ctc | aat | ccc | cga | caa | gtc | ttc | gac | ctg | 1072 |
| Ile | Gln | Ser | Phe | Leu | Trp | Tyr | Leu | Asn | Pro | Arg | Gln | Val | Phe | Asp | Leu |  |
|  |  | 315 |  |  |  | 320 |  |  |  | 325 |  |  |  |  |  |  |

| agc | cag | gga | ggg | ccc | aag | gag | gcg | ctg | gag | atg | tac | cgc | aaa | gtg | cac | 1120 |
| Ser | Gln | Gly | Gly | Pro | Lys | Glu | Ala | Leu | Glu | Met | Tyr | Arg | Lys | Val | His |  |
| 330 |  |  |  | 335 |  |  |  | 340 |  |  |  |  |  |  |  |  |

| aac | ctg | cgg | atc | ctg | gcg | tgc | ggg | ggc | gac | ggc | acg | gtg | ggc | tgg | atc | 1168 |
| Asn | Leu | Arg | Ile | Leu | Ala | Cys | Gly | Gly | Asp | Gly | Thr | Val | Gly | Trp | Ile |  |
| 345 |  |  |  | 350 |  |  |  | 355 |  |  |  | 360 |  |  |  |  |

| ctc | tcc | acc | ctg | gac | cag | cta | cgc | ctg | aag | ccg | cca | ccc | cct | gtt | gcc | 1216 |
| Leu | Ser | Thr | Leu | Asp | Gln | Leu | Arg | Leu | Lys | Pro | Pro | Pro | Pro | Val | Ala |  |
|  |  |  | 365 |  |  |  | 370 |  |  |  | 375 |  |  |  |  |  |

| atc | ctg | ccc | ctg | ggt | act | ggc | aac | gac | ttg | gcc | cga | acc | ctc | aac | tgg | 1264 |
| Ile | Leu | Pro | Leu | Gly | Thr | Gly | Asn | Asp | Leu | Ala | Arg | Thr | Leu | Asn | Trp |  |
|  |  |  | 380 |  |  |  | 385 |  |  |  | 390 |  |  |  |  |  |

| ggt | ggg | ggc | tac | aca | gat | gag | cct | gtg | tcc | aag | atc | ctc | tcc | cac | gtg | 1312 |
| Gly | Gly | Gly | Tyr | Thr | Asp | Glu | Pro | Val | Ser | Lys | Ile | Leu | Ser | His | Val |  |
|  |  | 395 |  |  |  | 400 |  |  |  | 405 |  |  |  |  |  |  |

| gag | gag | ggg | aac | gtg | gta | cag | ctg | gac | cgc | tgg | gac | ctc | cac | gct | gag | 1360 |
| Glu | Glu | Gly | Asn | Val | Val | Gln | Leu | Asp | Arg | Trp | Asp | Leu | His | Ala | Glu |  |
| 410 |  |  |  | 415 |  |  |  | 420 |  |  |  |  |  |  |  |  |

| ccc | aac | ccc | gag | gca | ggg | cct | gag | gac | cga | gat | gaa | ggc | gcc | acc | gac | 1408 |
| Pro | Asn | Pro | Glu | Ala | Gly | Pro | Glu | Asp | Arg | Asp | Glu | Gly | Ala | Thr | Asp |  |
| 425 |  |  |  | 430 |  |  |  | 435 |  |  |  | 440 |  |  |  |  |

| cgg | ttg | ccc | ctg | gat | gtc | ttc | aac | aac | tac | ttc | agc | ctg | ggc | ttt | gac | 1456 |
| Arg | Leu | Pro | Leu | Asp | Val | Phe | Asn | Asn | Tyr | Phe | Ser | Leu | Gly | Phe | Asp |  |
|  |  |  | 445 |  |  |  | 450 |  |  |  | 455 |  |  |  |  |  |

| gcc | cac | gtc | acc | ctg | gag | ttc | cac | gag | tct | cga | gag | gcc | aac | cca | gag | 1504 |
| Ala | His | Val | Thr | Leu | Glu | Phe | His | Glu | Ser | Arg | Glu | Ala | Asn | Pro | Glu |  |
|  |  |  | 460 |  |  |  | 465 |  |  |  | 470 |  |  |  |  |  |

| aaa | ttc | aac | agc | cgc | ttt | cgg | aat | aag | atg | ttc | tac | gcc | ggg | aca | gct | 1552 |
| Lys | Phe | Asn | Ser | Arg | Phe | Arg | Asn | Lys | Met | Phe | Tyr | Ala | Gly | Thr | Ala |  |
|  |  | 475 |  |  |  | 480 |  |  |  | 485 |  |  |  |  |  |  |

| ttc | tct | gac | ttc | ctg | atg | ggc | agc | tcc | aag | gac | ctg | gcc | aag | cac | atc | 1600 |
| Phe | Ser | Asp | Phe | Leu | Met | Gly | Ser | Ser | Lys | Asp | Leu | Ala | Lys | His | Ile |  |
|  | 490 |  |  |  | 495 |  |  |  | 500 |  |  |  |  |  |  |  |

| cga | gtg | gtg | tgt | gat | gga | atg | gac | ttg | act | ccc | aag | atc | cag | gac | ctg | 1648 |
| Arg | Val | Val | Cys | Asp | Gly | Met | Asp | Leu | Thr | Pro | Lys | Ile | Gln | Asp | Leu |  |
| 505 |  |  |  | 510 |  |  |  | 515 |  |  |  | 520 |  |  |  |  |

| aaa | ccc | cag | tgt | gtt | gtt | ttc | ctg | aac | atc | ccc | agg | tac | tgt | gcg | ggc | 1696 |
| Lys | Pro | Gln | Cys | Val | Val | Phe | Leu | Asn | Ile | Pro | Arg | Tyr | Cys | Ala | Gly |  |
|  |  |  | 525 |  |  |  | 530 |  |  |  | 535 |  |  |  |  |  |

| acc | atg | ccc | tgg | ggc | cac | cct | ggg | gag | cac | cac | gac | ttt | gag | ccc | cag | 1744 |
| Thr | Met | Pro | Trp | Gly | His | Pro | Gly | Glu | His | His | Asp | Phe | Glu | Pro | Gln |  |
|  |  |  | 540 |  |  |  | 545 |  |  |  | 550 |  |  |  |  |  |

| cgg | cat | gac | gac | ggc | tac | ctc | gag | gtc | att | ggc | ttc | acc | atg | acg | tcg | 1792 |
| Arg | His | Asp | Asp | Gly | Tyr | Leu | Glu | Val | Ile | Gly | Phe | Thr | Met | Thr | Ser |  |
|  |  | 555 |  |  |  | 560 |  |  |  | 565 |  |  |  |  |  |  |

| ttg | gcc | gcg | ctg | cag | gtg | ggc | gga | cac | ggc | gag | cgg | ctg | acg | cag | tgt | 1840 |
| Leu | Ala | Ala | Leu | Gln | Val | Gly | Gly | His | Gly | Glu | Arg | Leu | Thr | Gln | Cys |  |

```
            570                 575                 580
cgc gag gtg gtg ctc acc aca tcc aag gcc atc ccg gtg cag gtg gat         1888
Arg Glu Val Val Leu Thr Thr Ser Lys Ala Ile Pro Val Gln Val Asp
585                 590                 595                 600 ggc gag ccc tgc aag ctt gca gcc tca cgc atc cgc atc gcc ctg cgc         1936
Gly Glu Pro Cys Lys Leu Ala Ala Ser Arg Ile Arg Ile Ala Leu Arg
                605                 610                 615 aac cag gcc acc atg gtg cag aag gcc aag cgg cgg agc gcc gcc ccc         1984
Asn Gln Ala Thr Met Val Gln Lys Ala Lys Arg Arg Ser Ala Ala Pro
            620                 625                 630 ctg cac agc gac cag cag ccg gtg cca gag cag ttg cgc atc cag gtg         2032
Leu His Ser Asp Gln Gln Pro Val Pro Glu Gln Leu Arg Ile Gln Val
                635                 640                 645 agt cgc gtc agc atg cac gac tat gag gcc ctg cac tac gac aag gag         2080
Ser Arg Val Ser Met His Asp Tyr Glu Ala Leu His Tyr Asp Lys Glu
650                 655                 660 cag ctc aag gag gcc tct gtg ccg ctg ggc act gtg gtg gtc cca gga         2128
Gln Leu Lys Glu Ala Ser Val Pro Leu Gly Thr Val Val Val Pro Gly
665                 670                 675                 680 gac agt gac cta gag ctc tgc cgt gcc cac att gag aga ctc cag cag         2176
Asp Ser Asp Leu Glu Leu Cys Arg Ala His Ile Glu Arg Leu Gln Gln
                685                 690                 695 gag ccc gat ggt gct gga gcc aag tcc ccg aca tgc cag aaa ctg tcc         2224
Glu Pro Asp Gly Ala Gly Ala Lys Ser Pro Thr Cys Gln Lys Leu Ser
            700                 705                 710 ccc aag tgg tgc ttc ctg gac gcc acc act gcc agc cgc ttc tac agg         2272
Pro Lys Trp Cys Phe Leu Asp Ala Thr Thr Ala Ser Arg Phe Tyr Arg
                715                 720                 725 atc gac cga gcc cag gag cac ctc aac tat gtg act gag atc gca cag         2320
Ile Asp Arg Ala Gln Glu His Leu Asn Tyr Val Thr Glu Ile Ala Gln
            730                 735                 740 gat gag att tat atc ctg gac cct gag ctg ctg ggg gca tcg gcc cgg         2368
Asp Glu Ile Tyr Ile Leu Asp Pro Glu Leu Leu Gly Ala Ser Ala Arg
745                 750                 755                 760 cct gac ctc cca acc ccc act tcc cct ctc ccc acc tca ccc tgc tca         2416
Pro Asp Leu Pro Thr Pro Thr Ser Pro Leu Pro Thr Ser Pro Cys Ser
                765                 770                 775 ccc acg ccc cgg tca ctg caa ggg gat gct gca ccc cct caa ggt gaa         2464
Pro Thr Pro Arg Ser Leu Gln Gly Asp Ala Ala Pro Pro Gln Gly Glu
            780                 785                 790 gag ctg att gag gct gcc aag agg aac gac ttc tgt aag ctc cag gag         2512
Glu Leu Ile Glu Ala Ala Lys Arg Asn Asp Phe Cys Lys Leu Gln Glu
                795                 800                 805 ctg cac cga gct ggg ggc gac ctc atg cac cga gac gag cag agt cgc         2560
Leu His Arg Ala Gly Gly Asp Leu Met His Arg Asp Glu Gln Ser Arg
810                 815                 820 acg ctc ctg cac cac gca gtc agc act ggc agc aag gat gtg gtc cgc         2608
Thr Leu Leu His His Ala Val Ser Thr Gly Ser Lys Asp Val Val Arg
825                 830                 835                 840 tac ctg ctg gac cac gcc ccc cca gag atc ctt gat gcg gtg gag gaa         2656
Tyr Leu Leu Asp His Ala Pro Pro Glu Ile Leu Asp Ala Val Glu Glu
                845                 850                 855 aac ggg gag acc tgt ttg cac caa gca gcg gcc ctg ggc cag cgc acc         2704
Asn Gly Glu Thr Cys Leu His Gln Ala Ala Ala Leu Gly Gln Arg Thr
            860                 865                 870 atc tgc cac tac atc gtg gag gcc ggg gcc tcg ctc atg aag aca gac         2752
Ile Cys His Tyr Ile Val Glu Ala Gly Ala Ser Leu Met Lys Thr Asp
                875                 880                 885 cag cag ggc gac act ccc cgg cag cgg gct gag aag gct cag gac acc         2800
Gln Gln Gly Asp Thr Pro Arg Gln Arg Ala Glu Lys Ala Gln Asp Thr
```

```
                    890                895                900
gag ctg gcc gcc tac ctg gag aac cgg cag cac tac cag atg atc cag         2848
Glu Leu Ala Ala Tyr Leu Glu Asn Arg Gln His Tyr Gln Met Ile Gln
905                910                 915                920 cgg gag gac cag gag acg gct gtg tag cgggccgccc acgggcagca               2895
Arg Glu Asp Gln Glu Thr Ala Val
            925 ggagggacaa tgcggccagg ggacgagcgc cttccttgcc cacctcactg ccacattcca       2955
gtgggacggc cacgggggga cctaggcccc agggaaagag ccccatgccg cccctaagg        3015
agccgcccag acctagggct ggactcagga gctgggggg cctcacctgt tccctgagg         3075
accccgccgg acccggaggc tcacaggaa caagacacgg ctgggttgga tatgcctttg        3135
ccggggttct gggggcaggc gctccctggc cgcagcagat gccctcccag gagtggaggg       3195
gctggagagg gggaggcctt cgggaagagg cttcctgggc ccctggtct tcggccgggt        3255
ccccagcccc cgctcctgcc ccaccccacc tcctccgggc ttcctcccgg aaactcagcg       3315
cctgctgcac ttgcctgccc tgccttgctt ggcacccgct ccggcgaccc tccccgctcc       3375
cctgtcattt catcgcggac tgtgcggcct ggggtgggg ggcgggactc tcacggtgac        3435
atgtttacag ctgggtgtga ctcagtaaag tggattttttt tttctttaaa aaaaa          3490
```

<210> SEQ ID NO 4
<211> LENGTH: 928
<212> TYPE: PRT
<213> ORGANISM: Homo sapiens

<400> SEQUENCE: 4

```
Met Glu Pro Arg Asp Gly Ser Pro Glu Ala Arg Ser Ser Asp Ser Glu
 1               5                  10                  15

Ser Ala Ser Ala Ser Ser Gly Ser Glu Arg Asp Ala Gly Pro Glu
            20                  25                  30

Pro Asp Lys Ala Pro Arg Arg Leu Asn Lys Arg Arg Phe Pro Gly Leu
        35                  40                  45

Arg Leu Phe Gly His Arg Lys Ala Ile Thr Lys Ser Gly Leu Gln His
    50                  55                  60

Leu Ala Pro Pro Pro Thr Pro Gly Ala Pro Cys Ser Glu Ser Glu
65                  70                  75                  80

Arg Gln Ile Arg Ser Thr Val Asp Trp Ser Glu Ser Ala Thr Tyr Gly
                85                  90                  95

Glu His Ile Trp Phe Glu Thr Asn Val Ser Gly Asp Phe Cys Tyr Val
            100                 105                 110

Gly Glu Gln Tyr Cys Val Ala Arg Met Leu Lys Ser Val Ser Arg Arg
        115                 120                 125

Lys Cys Ala Ala Cys Lys Ile Val Val His Thr Pro Cys Ile Glu Gln
    130                 135                 140

Leu Glu Lys Ile Asn Phe Arg Cys Lys Pro Ser Phe Arg Glu Ser Gly
145                 150                 155                 160

Ser Arg Asn Val Arg Glu Pro Thr Phe Val Arg His His Trp Val His
                165                 170                 175

Arg Arg Arg Gln Asp Gly Lys Cys Arg His Cys Gly Lys Gly Phe Gln
            180                 185                 190

Gln Lys Phe Thr Phe His Ser Lys Glu Ile Val Ala Ile Ser Cys Ser
        195                 200                 205

Trp Cys Lys Gln Ala Tyr His Ser Lys Val Ser Cys Phe Met Leu Gln
    210                 215                 220
```

-continued

```
Gln Ile Glu Glu Pro Cys Ser Leu Gly Val His Ala Val Val Ile
225                 230                 235                 240

Pro Pro Thr Trp Ile Leu Arg Ala Arg Arg Pro Gln Asn Thr Leu Lys
            245                 250                 255

Ala Ser Lys Lys Lys Arg Ala Ser Phe Lys Arg Lys Ser Ser Lys
        260                 265                 270

Lys Gly Pro Glu Glu Gly Arg Trp Arg Pro Phe Ile Ile Arg Pro Thr
        275                 280                 285

Pro Ser Pro Leu Met Lys Pro Leu Val Phe Val Asn Pro Lys Ser
    290                 295                 300

Gly Gly Asn Gln Gly Ala Lys Ile Ile Gln Ser Phe Leu Trp Tyr Leu
305                 310                 315                 320

Asn Pro Arg Gln Val Phe Asp Leu Ser Gln Gly Pro Lys Glu Ala
                325                 330                 335

Leu Glu Met Tyr Arg Lys Val His Asn Leu Arg Ile Leu Ala Cys Gly
                340                 345                 350

Gly Asp Gly Thr Val Gly Trp Ile Leu Ser Thr Leu Asp Gln Leu Arg
        355                 360                 365

Leu Lys Pro Pro Pro Val Ala Ile Leu Pro Leu Gly Thr Gly Asn
    370                 375                 380

Asp Leu Ala Arg Thr Leu Asn Trp Gly Gly Tyr Thr Asp Glu Pro
385                 390                 395                 400

Val Ser Lys Ile Leu Ser His Val Glu Glu Gly Asn Val Val Gln Leu
                405                 410                 415

Asp Arg Trp Asp Leu His Ala Glu Pro Asn Pro Glu Ala Gly Pro Glu
                420                 425                 430

Asp Arg Asp Glu Gly Ala Thr Asp Arg Leu Pro Leu Asp Val Phe Asn
        435                 440                 445

Asn Tyr Phe Ser Leu Gly Phe Asp Ala His Val Thr Leu Glu Phe His
    450                 455                 460

Glu Ser Arg Glu Ala Asn Pro Glu Lys Phe Asn Ser Arg Phe Arg Asn
465                 470                 475                 480

Lys Met Phe Tyr Ala Gly Thr Ala Phe Ser Asp Phe Leu Met Gly Ser
                485                 490                 495

Ser Lys Asp Leu Ala Lys His Ile Arg Val Val Cys Asp Gly Met Asp
        500                 505                 510

Leu Thr Pro Lys Ile Gln Asp Leu Lys Pro Gln Cys Val Val Phe Leu
    515                 520                 525

Asn Ile Pro Arg Tyr Cys Ala Gly Thr Met Pro Trp Gly His Pro Gly
530                 535                 540

Glu His His Asp Phe Glu Pro Gln Arg His Asp Asp Gly Tyr Leu Glu
545                 550                 555                 560

Val Ile Gly Phe Thr Met Thr Ser Leu Ala Ala Leu Gln Val Gly Gly
                565                 570                 575

His Gly Glu Arg Leu Thr Gln Cys Arg Glu Val Val Leu Thr Thr Ser
        580                 585                 590

Lys Ala Ile Pro Val Gln Val Asp Gly Glu Pro Cys Lys Leu Ala Ala
    595                 600                 605

Ser Arg Ile Arg Ile Ala Leu Arg Asn Gln Ala Thr Met Val Gln Lys
    610                 615                 620

Ala Lys Arg Arg Ser Ala Ala Pro Leu His Ser Asp Gln Pro Val
625                 630                 635                 640

Pro Glu Gln Leu Arg Ile Gln Val Ser Arg Val Ser Met His Asp Tyr
                645                 650                 655
```

```
Glu Ala Leu His Tyr Asp Lys Glu Gln Leu Lys Glu Ala Ser Val Pro
            660                 665                 670

Leu Gly Thr Val Val Pro Gly Asp Ser Asp Leu Glu Leu Cys Arg
        675                 680                 685

Ala His Ile Glu Arg Leu Gln Gln Glu Pro Asp Gly Ala Gly Ala Lys
690                 695                 700

Ser Pro Thr Cys Gln Lys Leu Ser Pro Lys Trp Cys Phe Leu Asp Ala
705                 710                 715                 720

Thr Thr Ala Ser Arg Phe Tyr Arg Ile Asp Arg Ala Gln Glu His Leu
                725                 730                 735

Asn Tyr Val Thr Glu Ile Ala Gln Asp Glu Ile Tyr Ile Leu Asp Pro
            740                 745                 750

Glu Leu Leu Gly Ala Ser Ala Arg Pro Asp Leu Pro Thr Pro Thr Ser
        755                 760                 765

Pro Leu Pro Thr Ser Pro Cys Ser Pro Thr Pro Arg Ser Leu Gln Gly
770                 775                 780

Asp Ala Ala Pro Pro Gln Gly Glu Leu Ile Glu Ala Ala Lys Arg
785                 790                 795                 800

Asn Asp Phe Cys Lys Leu Gln Glu Leu His Arg Ala Gly Gly Asp Leu
                805                 810                 815

Met His Arg Asp Glu Gln Ser Arg Thr Leu Leu His His Ala Val Ser
            820                 825                 830

Thr Gly Ser Lys Asp Val Val Arg Tyr Leu Leu Asp His Ala Pro Pro
        835                 840                 845

Glu Ile Leu Asp Ala Val Glu Glu Asn Gly Glu Thr Cys Leu His Gln
850                 855                 860

Ala Ala Ala Leu Gly Gln Arg Thr Ile Cys His Tyr Ile Val Glu Ala
865                 870                 875                 880

Gly Ala Ser Leu Met Lys Thr Asp Gln Gln Gly Asp Thr Pro Arg Gln
                885                 890                 895

Arg Ala Glu Lys Ala Gln Asp Thr Glu Leu Ala Ala Tyr Leu Glu Asn
            900                 905                 910

Arg Gln His Tyr Gln Met Ile Gln Arg Glu Asp Gln Glu Thr Ala Val
        915                 920                 925

<210> SEQ ID NO 5
<211> LENGTH: 4094
<212> TYPE: DNA
<213> ORGANISM: Homo sapiens
<220> FEATURE:
<221> NAME/KEY: CDS
<222> LOCATION: (126)..(3479)

<400> SEQUENCE: 5
tgctagctct ccaaactagg acttgctcag cagaggccgc cagcccggag ctggatccag      60
agcccggcct tggggacccc agctcccacc tgcgccctgc cttccagatc agccaaccgc     120 ctgcc atg gag act ttc ttt agg aga cat ttc cgg ggg aag gtg cca ggc     170
      Met Glu Thr Phe Phe Arg Arg His Phe Arg Gly Lys Val Pro Gly
      1               5                   10                  15 cct gga gag ggg cag cgg cgg ccc agc agc gtg ggg ctg ccc aca ggc     218
Pro Gly Glu Gly Gln Arg Arg Pro Ser Ser Val Gly Leu Pro Thr Gly
                20                  25                  30 aag gcc cgg cgt cgc tcc ccc gct ggg cag gcc tcc tca ctg gca        266
Lys Ala Arg Arg Arg Ser Pro Ala Gly Gln Ala Ser Ser Ser Leu Ala
            35                  40                  45 cag cgg cgc cgc tcc agc gcc cag ctc cag ggc tgc ctc ctg agt tgc     314
```

```
          Gln Arg Arg Arg Ser Ser Ala Gln Leu Gln Gly Cys Leu Leu Ser Cys
                   50                  55                  60 ggg gtg agg gcc cag ggt tcc agc cgc cgg cgc tcc agc act gtg ccc      362
Gly Val Arg Ala Gln Gly Ser Ser Arg Arg Arg Ser Ser Thr Val Pro
         65                  70                  75 cct tcc tgc aac ccc cgc ttc atc gtg gat aag gtg ctc act cca cag      410
Pro Ser Cys Asn Pro Arg Phe Ile Val Asp Lys Val Leu Thr Pro Gln
 80                  85                  90                  95 cct acc acc gtg ggg gcc cag ctt ctg ggt gca ccc ctg ctg ttg acc      458
Pro Thr Thr Val Gly Ala Gln Leu Leu Gly Ala Pro Leu Leu Leu Thr
                    100                 105                 110 ggg ctt gtg ggc atg aat gag gag gag ggt gtc cag gag gat gtg gta      506
Gly Leu Val Gly Met Asn Glu Glu Glu Gly Val Gln Glu Asp Val Val
                115                 120                 125 gcc gag gca tcg agc gcc atc cag cca ggc acc aag aca cca ggg cca      554
Ala Glu Ala Ser Ser Ala Ile Gln Pro Gly Thr Lys Thr Pro Gly Pro
            130                 135                 140 ccc cca cct cgg ggc gcc cag ccg ctg ttg ccc cta ccc cga tac gtg      602
Pro Pro Pro Arg Gly Ala Gln Pro Leu Leu Pro Leu Pro Arg Tyr Val
        145                 150                 155 cga cga gcc tcc tcc cac tgc tgc ccc gcg gat gcc gta tat gac cac      650
Arg Arg Ala Ser Ser His Cys Cys Pro Ala Asp Ala Val Tyr Asp His
160                 165                 170                 175 gct ctc tgg ggc ctg cac ggt tac tat cgg cgc ctc agc cag cgg cgg      698
Ala Leu Trp Gly Leu His Gly Tyr Tyr Arg Arg Leu Ser Gln Arg Arg
                    180                 185                 190 ccc tca ggc cag cac cct ggc cct ggg ggc cga aga gcc tca ggc acc      746
Pro Ser Gly Gln His Pro Gly Pro Gly Gly Arg Arg Ala Ser Gly Thr
                195                 200                 205 acc gcc ggc acc atg ctg ccc acc cgt gtg cgc cca ctg tcc cgc agg      794
Thr Ala Gly Thr Met Leu Pro Thr Arg Val Arg Pro Leu Ser Arg Arg
            210                 215                 220 cgc cag gta gcc cta cgg cgc aag gcg gcc gga ccc cag gcc tgg agc      842
Arg Gln Val Ala Leu Arg Arg Lys Ala Ala Gly Pro Gln Ala Trp Ser
        225                 230                 235 gcc ctg ctc gcg aaa gcc atc acc aag tcg ggc ctc cag cac ctg gcc      890
Ala Leu Leu Ala Lys Ala Ile Thr Lys Ser Gly Leu Gln His Leu Ala
240                 245                 250                 255 ccc cct ccg ccc acc cct ggg gcc ccg tgc agc gag tca gag cgg cag      938
Pro Pro Pro Pro Thr Pro Gly Ala Pro Cys Ser Glu Ser Glu Arg Gln
                    260                 265                 270 atc cgg agt aca gtg gac tgg agc gag tca gcg aca tat ggg gag cac      986
Ile Arg Ser Thr Val Asp Trp Ser Glu Ser Ala Thr Tyr Gly Glu His
                275                 280                 285 atc tgg ttc gag acc aac gtg tcc ggg gac ttc tgc tac gtt ggg gag     1034
Ile Trp Phe Glu Thr Asn Val Ser Gly Asp Phe Cys Tyr Val Gly Glu
            290                 295                 300 cag tac tgt gta gcc agg atg ctg aag tca gtg tct cga aga aag tgc     1082
Gln Tyr Cys Val Ala Arg Met Leu Lys Ser Val Ser Arg Arg Lys Cys
        305                 310                 315 gca gcc tgc aag att gtg gtg cac acg ccc tgc atc gag cag ctg gag     1130
Ala Ala Cys Lys Ile Val Val His Thr Pro Cys Ile Glu Gln Leu Glu
320                 325                 330                 335 aag ata aat ttc cgc tgt aag ccg tcc ttc cgt gaa tca ggc tcc agg     1178
Lys Ile Asn Phe Arg Cys Lys Pro Ser Phe Arg Glu Ser Gly Ser Arg
                    340                 345                 350 aat gtc cgc gag cca acc ttt gta cgg cac cac tgg gta cac aga cga     1226
Asn Val Arg Glu Pro Thr Phe Val Arg His His Trp Val His Arg Arg
                355                 360                 365 cgc cag gac ggc aag tgt cgg cac tgt ggg aag gga ttc cag cag aag     1274
```

-continued

```
                Arg Gln Asp Gly Lys Cys Arg His Cys Gly Lys Gly Phe Gln Gln Lys
                                370             375             380 ttc acc ttc cac agc aag gag att gtg gcc atc agc tgc tcg tgg tgc       1322
Phe Thr Phe His Ser Lys Glu Ile Val Ala Ile Ser Cys Ser Trp Cys
385                 390                 395 aag cag gca tac cac agc aag gtg tcc tgc ttc atg ctg cag cag atc       1370
Lys Gln Ala Tyr His Ser Lys Val Ser Cys Phe Met Leu Gln Gln Ile
400                 405                 410                 415 gag gag ccg tgc tcg ctg ggg gtc cac gca gcc gtg gtc atc ccg ccc       1418
Glu Glu Pro Cys Ser Leu Gly Val His Ala Ala Val Val Ile Pro Pro
                420                 425                 430 acc tgg atc ctc cgc gcc cgg agg ccc cag aat act ctg aaa gca agc       1466
Thr Trp Ile Leu Arg Ala Arg Arg Pro Gln Asn Thr Leu Lys Ala Ser
                435                 440                 445 aag aag aag aag agg gca tcc ttc aag agg aag tcc agc aag aaa ggg       1514
Lys Lys Lys Lys Arg Ala Ser Phe Lys Arg Lys Ser Ser Lys Lys Gly
            450                 455                 460 cct gag gag ggc cgc tgg aga ccc ttc atc atc agg ccc acc ccc tcc       1562
Pro Glu Glu Gly Arg Trp Arg Pro Phe Ile Ile Arg Pro Thr Pro Ser
465                 470                 475 ccg ctc atg aag ccc ctg ctg gtg ttt gtg aac ccc aag agt ggg ggc       1610
Pro Leu Met Lys Pro Leu Leu Val Phe Val Asn Pro Lys Ser Gly Gly
480                 485                 490                 495 aac cag ggt gca aag atc atc cag tct ttc ctc tgg tat ctc aat ccc       1658
Asn Gln Gly Ala Lys Ile Ile Gln Ser Phe Leu Trp Tyr Leu Asn Pro
                500                 505                 510 cga caa gtc ttc gac ctg agc cag gga ggg ccc aag gag gcg ctg gag       1706
Arg Gln Val Phe Asp Leu Ser Gln Gly Gly Pro Lys Glu Ala Leu Glu
                515                 520                 525 atg tac cgc aaa gtg cac aac ctg cgg atc ctg gcg tgc ggg ggc gac       1754
Met Tyr Arg Lys Val His Asn Leu Arg Ile Leu Ala Cys Gly Gly Asp
                530                 535                 540 ggc acg gtg ggc tgg atc ctc tcc acc ctg gac cag cta cgc ctg aag       1802
Gly Thr Val Gly Trp Ile Leu Ser Thr Leu Asp Gln Leu Arg Leu Lys
            545                 550                 555 ccg cca ccc cct gtt gcc atc ctg ccc ctg ggt act ggc aac gac ttg       1850
Pro Pro Pro Pro Val Ala Ile Leu Pro Leu Gly Thr Gly Asn Asp Leu
560                 565                 570                 575 gcc cga acc ctc aac tgg ggt ggg ggc tac aca gat gag cct gtg tcc       1898
Ala Arg Thr Leu Asn Trp Gly Gly Gly Tyr Thr Asp Glu Pro Val Ser
                580                 585                 590 aag atc ctc tcc cac gtg gag gag ggg aac gtg gta cag ctg gac cgc       1946
Lys Ile Leu Ser His Val Glu Glu Gly Asn Val Val Gln Leu Asp Arg
                595                 600                 605 tgg gac ctc cac gct gag ccc aac ccc gag gca ggg cct gag gac cga       1994
Trp Asp Leu His Ala Glu Pro Asn Pro Glu Ala Gly Pro Glu Asp Arg
                610                 615                 620 gat gaa ggc gcc acc gac cgg ttg ccc ctg gat gtc ttc aac aac tac       2042
Asp Glu Gly Ala Thr Asp Arg Leu Pro Leu Asp Val Phe Asn Asn Tyr
625                 630                 635 ttc agc ctg ggc ttt gac gcc cac gtc acc ctg gag ttc cac gag tct       2090
Phe Ser Leu Gly Phe Asp Ala His Val Thr Leu Glu Phe His Glu Ser
640                 645                 650                 655 cga gag gcc aac cca gag aaa ttc aac agc cgc ttt cgg aat aag atg       2138
Arg Glu Ala Asn Pro Glu Lys Phe Asn Ser Arg Phe Arg Asn Lys Met
                660                 665                 670 ttc tac gcc ggg aca gct ttc tct gac ttc ctg atg ggc agc tcc aag       2186
Phe Tyr Ala Gly Thr Ala Phe Ser Asp Phe Leu Met Gly Ser Ser Lys
                675                 680                 685 gac ctg gcc aag cac atc cga gtg gtg tgt gat gga atg gac ttg act       2234
```

-continued

| | | |
|---|---|---|
| Asp Leu Ala Lys His Ile Arg Val Val Cys Asp Gly Met Asp Leu Thr<br>690 695 700 | | |
| ccc aag atc cag gac ctg aaa ccc cag tgt gtt gtt ttc ctg aac atc<br>Pro Lys Ile Gln Asp Leu Lys Pro Gln Cys Val Val Phe Leu Asn Ile<br>705 710 715 | 2282 | |
| ccc agg tac tgt gcg ggc acc atg ccc tgg ggc cac cct ggg gag cac<br>Pro Arg Tyr Cys Ala Gly Thr Met Pro Trp Gly His Pro Gly Glu His<br>720 725 730 735 | 2330 | |
| cac gac ttt gag ccc cag cgg cat gac gac ggc tac ctc gag gtc att<br>His Asp Phe Glu Pro Gln Arg His Asp Asp Gly Tyr Leu Glu Val Ile<br>740 745 750 | 2378 | |
| ggc ttc acc atg acg tcg ttg gcc gcg ctg cag gtg ggc gga cac ggc<br>Gly Phe Thr Met Thr Ser Leu Ala Ala Leu Gln Val Gly Gly His Gly<br>755 760 765 | 2426 | |
| gag cgg ctg acg cag tgt cgc gag gtg gtg ctc acc aca tcc aag gcc<br>Glu Arg Leu Thr Gln Cys Arg Glu Val Val Leu Thr Thr Ser Lys Ala<br>770 775 780 | 2474 | |
| atc ccg gtg cag gtg gat ggc gag ccc tgc aag ctt gca gcc tca cgc<br>Ile Pro Val Gln Val Asp Gly Glu Pro Cys Lys Leu Ala Ala Ser Arg<br>785 790 795 | 2522 | |
| atc cgc atc gcc ctg cgc aac cag gcc acc atg gtg cag aag gcc aag<br>Ile Arg Ile Ala Leu Arg Asn Gln Ala Thr Met Val Gln Lys Ala Lys<br>800 805 810 815 | 2570 | |
| cgg cgg agc gcc gcc ccc ctg cac agc gac cag cag ccg gtg cca gag<br>Arg Arg Ser Ala Ala Pro Leu His Ser Asp Gln Gln Pro Val Pro Glu<br>820 825 830 | 2618 | |
| cag ttg cgc atc cag gtg agt cgc gtc agc atg cac gac tat gag gcc<br>Gln Leu Arg Ile Gln Val Ser Arg Val Ser Met His Asp Tyr Glu Ala<br>835 840 845 | 2666 | |
| ctg cac tac gac aag gag cag ctc aag gag gcc tct gtg ccg ctg ggc<br>Leu His Tyr Asp Lys Glu Gln Leu Lys Glu Ala Ser Val Pro Leu Gly<br>850 855 860 | 2714 | |
| act gtg gtg gtc cca gga gac agt gac cta gag ctc tgc cgt gcc cac<br>Thr Val Val Val Pro Gly Asp Ser Asp Leu Glu Leu Cys Arg Ala His<br>865 870 875 | 2762 | |
| att gag aga ctc cag cag gag ccc gat ggt gct gga gcc aag tcc ccg<br>Ile Glu Arg Leu Gln Gln Glu Pro Asp Gly Ala Gly Ala Lys Ser Pro<br>880 885 890 895 | 2810 | |
| aca tgc cag aaa ctg tcc ccc aag tgg tgc ttc ctg gac gcc acc act<br>Thr Cys Gln Lys Leu Ser Pro Lys Trp Cys Phe Leu Asp Ala Thr Thr<br>900 905 910 | 2858 | |
| gcc agc cgc ttc tac agg atc gac cga gcc cag gag cac ctc aac tat<br>Ala Ser Arg Phe Tyr Arg Ile Asp Arg Ala Gln Glu His Leu Asn Tyr<br>915 920 925 | 2906 | |
| gtg act gag atc gca cag gat gag att tat atc ctg gac cct gag ctg<br>Val Thr Glu Ile Ala Gln Asp Glu Ile Tyr Ile Leu Asp Pro Glu Leu<br>930 935 940 | 2954 | |
| ctg ggg gca tcg gcc cgg cct gac ctc cca acc ccc act tcc cct ctc<br>Leu Gly Ala Ser Ala Arg Pro Asp Leu Pro Thr Pro Thr Ser Pro Leu<br>945 950 955 | 3002 | |
| ccc acc tca ccc tgc tca ccc acg ccc cgg tca ctg caa ggg gat gct<br>Pro Thr Ser Pro Cys Ser Pro Thr Pro Arg Ser Leu Gln Gly Asp Ala<br>960 965 970 975 | 3050 | |
| gca ccc cct caa ggt gaa gag ctg att gag gct gcc aag agg aac gac<br>Ala Pro Pro Gln Gly Glu Glu Leu Ile Glu Ala Ala Lys Arg Asn Asp<br>980 985 990 | 3098 | |
| ttc tgt aag ctc cag gag ctg cac cga gct ggg ggc gac ctc atg cac<br>Phe Cys Lys Leu Gln Glu Leu His Arg Ala Gly Gly Asp Leu Met His<br>995 1000 1005 | 3146 | |
| cga gac gag cag agt cgc acg ctc ctg cac cac gca gtc agc act ggc<br> | 3194 | |

-continued

| | | | | | | | | | | | | |
|---|---|---|---|---|---|---|---|---|---|---|---|---|
|Arg|Asp|Glu|Gln|Ser|Arg|Thr|Leu|Leu|His|His|Ala|Val|Ser|Thr|Gly|
| |1010| | | |1015| | | |1020| | | | | | | agc aag gat gtg gtc cgc tac ctg ctg gac cac gcc ccc cca gag atc      3242
Ser Lys Asp Val Val Arg Tyr Leu Leu Asp His Ala Pro Pro Glu Ile
    1025                1030                1035 ctt gat gcg gtg gag gaa aac ggg gag acc tgt ttg cac caa gca gcg      3290
Leu Asp Ala Val Glu Glu Asn Gly Glu Thr Cys Leu His Gln Ala Ala
1040                1045                1050                1055 gcc ctg ggc cag cgc acc atc tgc cac tac atc gtg gag gcc ggg gcc      3338
Ala Leu Gly Gln Arg Thr Ile Cys His Tyr Ile Val Glu Ala Gly Ala
                1060                1065                1070 tcg ctc atg aag aca gac cag cag ggc gac act ccc cgg cag cgg gct      3386
Ser Leu Met Lys Thr Asp Gln Gln Gly Asp Thr Pro Arg Gln Arg Ala
            1075                1080                1085 gag aag gct cag gac acc gag ctg gcc gcc tac ctg gag aac cgg cag      3434
Glu Lys Ala Gln Asp Thr Glu Leu Ala Ala Tyr Leu Glu Asn Arg Gln
        1090                1095                1100 cac tac cag atg atc cag cgg gag gac cag gag acg gct gtg tag          3479
His Tyr Gln Met Ile Gln Arg Glu Asp Gln Glu Thr Ala Val
    1105                1110                1115 cgggccgccc acgggcagca ggagggacaa tgcggccagg ggacgagcgc cttccttgcc    3539
cacctcactg ccacattcca gtgggacggc cacggggggga cctaggcccc agggaaagag   3599
ccccatgccg cccccctaagg agccgcccag acctagggct ggactcagga gctgggggg    3659
cctcacctgt tccctgagg accccgccgg acccggaggc tcacaggaa caagacacgg      3719
ctgggttgga tatgcctttg ccggggttct ggggcagggc gctccctggc cgcagcagat    3779
gccctcccag gagtggaggg gctggagagg gggaggcctt cgggaagagg cttcctgggc    3839
ccctggtct tcggccgggt ccccagcccc cgctcctgcc ccaccccacc tcctccgggc     3899
ttcctcccgg aaactcagcg cctgctgcac ttgcctgccc tgccttgctt ggcacccgct    3959
ccggcgaccc tccccgctcc cctgtcattt catcgcggac tgtgcggcct gggggtgggg    4019
ggcgggactc tcacggtgac atgtttacag ctgggtgtga ctcagtaaag tggatttttt    4079
tttcttttaaa aaaaa                                                    4094

<210> SEQ ID NO 6
<211> LENGTH: 1117
<212> TYPE: PRT
<213> ORGANISM: Homo sapiens

<400> SEQUENCE: 6

Met Glu Thr Phe Phe Arg Arg His Phe Arg Gly Lys Val Pro Gly Pro
1               5                   10                  15

Gly Glu Gly Gln Arg Arg Pro Ser Ser Val Gly Leu Pro Thr Gly Lys
            20                  25                  30

Ala Arg Arg Arg Ser Pro Ala Gly Gln Ala Ser Ser Leu Ala Gln
        35                  40                  45

Arg Arg Arg Ser Ser Ala Gln Leu Gln Gly Cys Leu Leu Ser Cys Gly
    50                  55                  60

Val Arg Ala Gln Gly Ser Ser Arg Arg Arg Ser Ser Thr Val Pro Pro
65                  70                  75                  80

Ser Cys Asn Pro Arg Phe Ile Val Asp Lys Val Leu Thr Pro Gln Pro
                85                  90                  95

Thr Thr Val Gly Ala Gln Leu Leu Gly Ala Pro Leu Leu Thr Gly
            100                 105                 110

Leu Val Gly Met Asn Glu Glu Glu Gly Val Gln Glu Asp Val Val Ala
        115                 120                 125

```
Glu Ala Ser Ser Ala Ile Gln Pro Gly Thr Lys Thr Pro Gly Pro Pro
            130                 135                 140

Pro Pro Arg Gly Ala Gln Pro Leu Leu Pro Leu Pro Arg Tyr Val Arg
145                 150                 155                 160

Arg Ala Ser Ser His Cys Cys Pro Ala Asp Ala Val Tyr Asp His Ala
                165                 170                 175

Leu Trp Gly Leu His Gly Tyr Tyr Arg Arg Leu Ser Gln Arg Arg Pro
            180                 185                 190

Ser Gly Gln His Pro Gly Pro Gly Arg Arg Ala Ser Gly Thr Thr
            195                 200                 205

Ala Gly Thr Met Leu Pro Thr Arg Val Arg Pro Leu Ser Arg Arg Arg
210                 215                 220

Gln Val Ala Leu Arg Arg Lys Ala Ala Gly Pro Gln Ala Trp Ser Ala
225                 230                 235                 240

Leu Leu Ala Lys Ala Ile Thr Lys Ser Gly Leu Gln His Leu Ala Pro
                245                 250                 255

Pro Pro Pro Thr Pro Gly Ala Pro Cys Ser Glu Ser Glu Arg Gln Ile
            260                 265                 270

Arg Ser Thr Val Asp Trp Ser Glu Ser Ala Thr Tyr Gly Glu His Ile
            275                 280                 285

Trp Phe Glu Thr Asn Val Ser Gly Asp Phe Cys Tyr Val Gly Glu Gln
290                 295                 300

Tyr Cys Val Ala Arg Met Leu Lys Ser Val Ser Arg Arg Lys Cys Ala
305                 310                 315                 320

Ala Cys Lys Ile Val Val His Thr Pro Cys Ile Glu Gln Leu Glu Lys
                325                 330                 335

Ile Asn Phe Arg Cys Lys Pro Ser Phe Arg Glu Ser Gly Ser Arg Asn
            340                 345                 350

Val Arg Glu Pro Thr Phe Val Arg His His Trp Val His Arg Arg Arg
            355                 360                 365

Gln Asp Gly Lys Cys Arg His Cys Gly Lys Gly Phe Gln Gln Lys Phe
370                 375                 380

Thr Phe His Ser Lys Glu Ile Val Ala Ile Ser Cys Ser Trp Cys Lys
385                 390                 395                 400

Gln Ala Tyr His Ser Lys Val Ser Cys Phe Met Leu Gln Gln Ile Glu
                405                 410                 415

Glu Pro Cys Ser Leu Gly Val His Ala Ala Val Ile Pro Pro Thr
            420                 425                 430

Trp Ile Leu Arg Ala Arg Arg Pro Gln Asn Thr Leu Lys Ala Ser Lys
            435                 440                 445

Lys Lys Lys Arg Ala Ser Phe Lys Arg Lys Ser Ser Lys Lys Gly Pro
450                 455                 460

Glu Glu Gly Arg Trp Arg Pro Phe Ile Ile Arg Pro Thr Pro Ser Pro
465                 470                 475                 480

Leu Met Lys Pro Leu Leu Val Phe Val Asn Pro Lys Ser Gly Gly Asn
                485                 490                 495

Gln Gly Ala Lys Ile Ile Gln Ser Phe Leu Trp Tyr Leu Asn Pro Arg
            500                 505                 510

Gln Val Phe Asp Leu Ser Gln Gly Gly Pro Lys Glu Ala Leu Glu Met
            515                 520                 525

Tyr Arg Lys Val His Asn Leu Arg Ile Leu Ala Cys Gly Gly Asp Gly
530                 535                 540

Thr Val Gly Trp Ile Leu Ser Thr Leu Asp Gln Leu Arg Leu Lys Pro
```

```
            545                 550                 555                 560
Pro Pro Pro Val Ala Ile Leu Pro Leu Gly Thr Gly Asn Asp Leu Ala
                565                 570                 575

Arg Thr Leu Asn Trp Gly Gly Tyr Thr Asp Glu Pro Val Ser Lys
            580                 585                 590

Ile Leu Ser His Val Glu Glu Gly Asn Val Val Gln Leu Asp Arg Trp
                595                 600                 605

Asp Leu His Ala Glu Pro Asn Pro Glu Ala Gly Pro Glu Asp Arg Asp
            610                 615                 620

Glu Gly Ala Thr Asp Arg Leu Pro Leu Asp Val Phe Asn Asn Tyr Phe
625                 630                 635                 640

Ser Leu Gly Phe Asp Ala His Val Thr Leu Glu Phe His Glu Ser Arg
                645                 650                 655

Glu Ala Asn Pro Glu Lys Phe Asn Ser Arg Phe Arg Asn Lys Met Phe
            660                 665                 670

Tyr Ala Gly Thr Ala Phe Ser Asp Phe Leu Met Gly Ser Ser Lys Asp
                675                 680                 685

Leu Ala Lys His Ile Arg Val Val Cys Asp Gly Met Asp Leu Thr Pro
            690                 695                 700

Lys Ile Gln Asp Leu Lys Pro Gln Cys Val Val Phe Leu Asn Ile Pro
705                 710                 715                 720

Arg Tyr Cys Ala Gly Thr Met Pro Trp Gly His Pro Gly Glu His His
                725                 730                 735

Asp Phe Glu Pro Gln Arg His Asp Asp Gly Tyr Leu Glu Val Ile Gly
            740                 745                 750

Phe Thr Met Thr Ser Leu Ala Ala Leu Gln Val Gly Gly His Gly Glu
                755                 760                 765

Arg Leu Thr Gln Cys Arg Glu Val Val Leu Thr Thr Ser Lys Ala Ile
            770                 775                 780

Pro Val Gln Val Asp Gly Glu Pro Cys Lys Leu Ala Ala Ser Arg Ile
785                 790                 795                 800

Arg Ile Ala Leu Arg Asn Gln Ala Thr Met Val Gln Lys Ala Lys Arg
                805                 810                 815

Arg Ser Ala Ala Pro Leu His Ser Asp Gln Gln Pro Val Pro Glu Gln
            820                 825                 830

Leu Arg Ile Gln Val Ser Arg Val Ser Met His Asp Tyr Glu Ala Leu
            835                 840                 845

His Tyr Asp Lys Glu Gln Leu Lys Glu Ala Ser Val Pro Leu Gly Thr
            850                 855                 860

Val Val Val Pro Gly Asp Ser Asp Leu Glu Leu Cys Arg Ala His Ile
865                 870                 875                 880

Glu Arg Leu Gln Gln Glu Pro Asp Gly Ala Gly Ala Lys Ser Pro Thr
                885                 890                 895

Cys Gln Lys Leu Ser Pro Lys Trp Cys Phe Leu Asp Ala Thr Thr Ala
            900                 905                 910

Ser Arg Phe Tyr Arg Ile Asp Arg Ala Gln Glu His Leu Asn Tyr Val
            915                 920                 925

Thr Glu Ile Ala Gln Asp Glu Ile Tyr Ile Leu Asp Pro Glu Leu Leu
            930                 935                 940

Gly Ala Ser Ala Arg Pro Asp Leu Pro Thr Pro Thr Ser Pro Leu Pro
945                 950                 955                 960

Thr Ser Pro Cys Ser Pro Thr Pro Arg Ser Leu Gln Gly Asp Ala Ala
                965                 970                 975
```

```
Pro Pro Gln Gly Glu Glu Leu Ile Glu Ala Ala Lys Arg Asn Asp Phe
        980                 985                 990

Cys Lys Leu Gln Glu Leu His Arg Ala Gly Gly Asp Leu Met His Arg
        995                 1000                1005

Asp Glu Gln Ser Arg Thr Leu Leu His His Ala Val Ser Thr Gly Ser
    1010                1015                1020

Lys Asp Val Val Arg Tyr Leu Leu Asp His Ala Pro Pro Glu Ile Leu
1025                1030                1035                1040

Asp Ala Val Glu Glu Asn Gly Glu Thr Cys Leu His Gln Ala Ala Ala
        1045                1050                1055

Leu Gly Gln Arg Thr Ile Cys His Tyr Ile Val Glu Ala Gly Ala Ser
        1060                1065                1070

Leu Met Lys Thr Asp Gln Gln Gly Asp Thr Pro Arg Gln Arg Ala Glu
        1075                1080                1085

Lys Ala Gln Asp Thr Glu Leu Ala Ala Tyr Leu Glu Asn Arg Gln His
        1090                1095                1100

Tyr Gln Met Ile Gln Arg Glu Asp Gln Glu Thr Ala Val
1105                1110                1115

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence:synthetic
      peptide

<400> SEQUENCE: 7

Cys Leu Glu Asn Arg Gln His Tyr Gln Met Ile Gln Arg Glu Asp Gln
  1               5                  10                  15
Glu

<210> SEQ ID NO 8
<211> LENGTH: 23
<212> TYPE: DNA
<213> ORGANISM: Artificial Sequence
<220> FEATURE:
<221> NAME/KEY: modified_base
<222> LOCATION: (6)
<223> OTHER INFORMATION: i
<220> FEATURE:
<221> NAME/KEY: modified_base
<222> LOCATION: (9)
<223> OTHER INFORMATION: i
<220> FEATURE:
<221> NAME/KEY: modified_base
<222> LOCATION: (15)
<223> OTHER INFORMATION: i
<220> FEATURE:
<221> NAME/KEY: modified_base
<222> LOCATION: (18)
<223> OTHER INFORMATION: i
<220> FEATURE:
<223> OTHER INFORMATION: Description of Artificial Sequence:synthetic
      oligonucleotide

<400> SEQUENCE: 8
tgyggnggng ayggnacngt ngg                                         23

<210> SEQ ID NO 9
<211> LENGTH: 23
<212> TYPE: DNA
<213> ORGANISM: Artificial Sequence
<220> FEATURE:
<221> NAME/KEY: modified_base
<222> LOCATION: (3)
```

-continued

```
<223> OTHER INFORMATION: i
<220> FEATURE:
<221> NAME/KEY: modified_base
<222> LOCATION: (9)
<223> OTHER INFORMATION: i
<220> FEATURE:
<221> NAME/KEY: modified_base
<222> LOCATION: (15)
<223> OTHER INFORMATION: i
<220> FEATURE:
<223> OTHER INFORMATION: Description of Artificial Sequence:synthetic
      oligonucleotide

<400> SEQUENCE: 9
canggytcnm crtcnayytg cat                                           23

<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 10
gcataagctc gatatcgagg tatcgtcctt g                                  31

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 11
ttgtctcgag gtcgacatct attcagtcgc c                                  31

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 12
atgactacaa ggacgacgat gagaaggc                                      28

<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 13
ctaggccttg tcatcgtcgt ccttgtagtc at                                 32

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 14
```

```
ctaccgtccc gcgaattcat ccg                                              23

<210> SEQ ID NO 15
<211> LENGTH: 18
<212> TYPE: PRT
<213> ORGANISM: Artificial Sequence
<220> FEATURE:
<223> OTHER INFORMATION: Description of Artificial Sequence:synthetic
      peptide

<400> SEQUENCE: 15

Lys Ala Ser Lys Lys Lys Lys Arg Ala Ser Phe Lys Arg Lys Ser Ser
 1               5                  10                  15

Lys Lys

<210> SEQ ID NO 16
<211> LENGTH: 18
<212> TYPE: PRT
<213> ORGANISM: Artificial Sequence
<220> FEATURE:
<223> OTHER INFORMATION: Description of Artificial Sequence:synthetic
      peptide

<400> SEQUENCE: 16

Lys Ala Ser Lys Lys Lys Lys Arg Ala Ala Phe Lys Arg Lys Ser Ser
 1               5                  10                  15

Lys Lys

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 17
gtgcaaagat catccagtct t                                                21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 18
tggagaggat ccagcccacc g                                                21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 19
accccaatcc ctctttccca g                                                21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence:synthetic
```

-continued oligonucleotide

<400> SEQUENCE: 20
gaaagactgg atgatctttg c                              21

<210> SEQ ID NO 21
<211> LENGTH: 35
<212> TYPE: PRT
<213> ORGANISM: Artificial Sequence
<220> FEATURE:
<223> OTHER INFORMATION: Description of Artificial Sequence:consensus
      sequence of DGK-epsilon's first zinc finger

<400> SEQUENCE: 21

Cys Xaa Xaa Cys Xaa Xaa Xaa Xaa Xaa Xaa Xaa Xaa Cys Xaa Xaa
 1               5                  10                  15

Cys Xaa Xaa Xaa Xaa Xaa Xaa Xaa Cys Xaa Xaa Xaa Xaa Xaa Xaa
                20                  25                  30

Xaa Xaa Cys
         35

<210> SEQ ID NO 22
<211> LENGTH: 40
<212> TYPE: PRT
<213> ORGANISM: Artificial Sequence
<220> FEATURE:
<223> OTHER INFORMATION: Description of Artificial Sequence:consensus
      sequence of DGK-epsilon's second zinc finger

<400> SEQUENCE: 22

Cys Xaa Xaa Cys Xaa Xaa Xaa Xaa Xaa Xaa Xaa Xaa Xaa Xaa Xaa
 1               5                  10                  15

Xaa Xaa Cys Xaa Xaa Cys Xaa Xaa Xaa Xaa Xaa Xaa Cys Xaa Xaa
                20                  25                  30

Xaa Xaa Xaa Xaa Xaa Xaa Xaa Cys
         35                  40

<210> SEQ ID NO 23
<211> LENGTH: 15
<212> TYPE: PRT
<213> ORGANISM: Homo sapiens

<400> SEQUENCE: 23

Lys Lys Lys Lys Arg Ala Ser Phe Lys Arg Lys Ser Ser Lys Lys
 1               5                  10                  15

<210> SEQ ID NO 24
<211> LENGTH: 55
<212> TYPE: PRT
<213> ORGANISM: Artificial Sequence
<220> FEATURE:
<223> OTHER INFORMATION: Description of Artificial Sequence: consensus
      sequence of DGK-zeta's first zinc finger

<400> SEQUENCE: 24

His Xaa Xaa Xaa Xaa Xaa Xaa Xaa Xaa Xaa Xaa Xaa Cys Xaa Xaa Xaa
 1               5                  10                  15

Xaa Xaa Xaa Cys Xaa Xaa Xaa Xaa Xaa Xaa Xaa Xaa Xaa Xaa Xaa
                20                  25                  30

Cys Xaa Xaa Cys Xaa Xaa Xaa Xaa His Xaa Xaa Cys Xaa Xaa Xaa Xaa
         35                  40                  45

Xaa Xaa Xaa Xaa Xaa Xaa Cys
         50                  55

```
<210> SEQ ID NO 25
<211> LENGTH: 59
<212> TYPE: PRT
<213> ORGANISM: Artificial Sequence
<220> FEATURE:
<223> OTHER INFORMATION: Description of Artificial Sequence:consensus
      sequence of DGK-zeta's second zinc finger

<400> SEQUENCE: 25

His Xaa Xaa Xaa Xaa Xaa Xaa Xaa Xaa Xaa Xaa Cys Xaa Xaa Cys
  1               5                  10                  15

Xaa Xaa Xaa Xaa Xaa Xaa Xaa Xaa Xaa Xaa Xaa Xaa Xaa Xaa Xaa
             20                  25                  30

Xaa Xaa Xaa Cys Xaa Xaa Cys Xaa Xaa Xaa Xaa His Xaa Xaa Xaa Xaa
         35                  40                  45

Cys Xaa Xaa Xaa Xaa Xaa Xaa Xaa Xaa Xaa Cys
         50                  55

<210> SEQ ID NO 26
<211> LENGTH: 27
<212> TYPE: PRT
<213> ORGANISM: Artificial Sequence
<220> FEATURE: NAME/KEY: SITE LOCATION: (7)..(26)
<223> OTHER INFORMATION: Where 5 of the Xaa's may be absent or present.
<220> FEATURE:
<223> OTHER INFORMATION: Description of Artificial Sequence:consensus
      sequence of DGK-zeta's ATP binding site

<400> SEQUENCE: 26

Gly Asp Gly Thr Val Gly Xaa Xaa Xaa Xaa Xaa Xaa Xaa Xaa Xaa
  1               5                  10                  15

Xaa Xaa Xaa Xaa Xaa Xaa Xaa Xaa Xaa Xaa Lys
             20                  25

<210> SEQ ID NO 27
<211> LENGTH: 27
<212> TYPE: PRT
<213> ORGANISM: Artificial Sequence
<220> FEATURE:
<221> NAME/KEY: SITE
<222> LOCATION: (7)..(26)
<223> OTHER INFORMATION: Where 5 of the Xaa's may be absent or present.
<220> FEATURE:
<223> OTHER INFORMATION: Description of Artificial Sequence:mutated
      variant of consensus sequence of DGK-zeta's ATP binding site

<400> SEQUENCE: 27

Gly Asp Asp Thr Val Gly Xaa Xaa Xaa Xaa Xaa Xaa Xaa Xaa Xaa
  1               5                  10                  15

Xaa Xaa Xaa Xaa Xaa Xaa Xaa Xaa Xaa Xaa Lys
             20                  25

<210> SEQ ID NO 28
<211> LENGTH: 6
<212> TYPE: PRT
<213> ORGANISM: Homo sapiens

<400> SEQUENCE: 28

Gly Asp Gly Thr Val Gly
  1               5

<210> SEQ ID NO 29
<211> LENGTH: 8
<212> TYPE: PRT
<213> ORGANISM: Homo sapiens
```

-continued

<400> SEQUENCE: 29

Cys Gly Gly Asp Gly Thr Val Gly
 1               5

<210> SEQ ID NO 30
<211> LENGTH: 8
<212> TYPE: PRT
<213> ORGANISM: Artificial Sequence
<220> FEATURE:
<221> NAME/KEY: VARIANT
<222> LOCATION: (3)
<223> OTHER INFORMATION: Valine or isoleucine at position 3.
<220> FEATURE:
<221> NAME/KEY: VARIANT
<222> LOCATION: (5)
<223> OTHER INFORMATION: Glycine or valine at position 5.
<220> FEATURE:
<223> OTHER INFORMATION: Description of Artificial Sequence:Consensus
      sequence of human DGK-alpha and the aligned
      sequences of other DGKs except Drosophila DGK2.

<400> SEQUENCE: 30

Met Gln Xaa Asp Xaa Glu Pro Trp
 1               5

<210> SEQ ID NO 31
<211> LENGTH: 358
<212> TYPE: PRT
<213> ORGANISM: Homo sapiens
<220> FEATURE:
<221> NAME/KEY: SITE
<222> LOCATION: (247)..(284)
<223> OTHER INFORMATION: Where 24 of the Xaa's may be absent or present.

<400> SEQUENCE: 31

Pro Leu Ile Ile Leu Ala Asn Ser Arg Ser Gly Thr Asn Met Gly Xaa
 1               5                  10                  15

Xaa Xaa Xaa Xaa Xaa Phe Xaa Xaa Leu Leu Asn Pro Val Gln Val Phe
             20                  25                  30

Asp Val Xaa Xaa Xaa Pro Pro Xaa Xaa Xaa Xaa Gln Leu Xaa Xaa Xaa
         35                  40                  45

Xaa Xaa Xaa Xaa Xaa Xaa Arg Xaa Leu Val Cys Gly Gly Asp Gly Thr
     50                  55                  60

Val Gly Trp Val Leu Asp Ala Val Asp Xaa Xaa Xaa Xaa Xaa Xaa Xaa
 65                  70                  75                  80

Xaa Xaa Xaa Xaa Xaa Xaa Val Ala Val Leu Pro Leu Gly Thr Gly Asn
                 85                  90                  95

Asp Leu Ser Asn Xaa Leu Xaa Trp Gly Thr Gly Tyr Xaa Xaa Xaa Xaa
            100                 105                 110

Xaa Val Xaa Xaa Val Leu Xaa Xaa Val Met Xaa Xaa Xaa Xaa Xaa Xaa
        115                 120                 125

Leu Asp Arg Trp Xaa Xaa Xaa Xaa Xaa Xaa Xaa Xaa Xaa Xaa Xaa Xaa
130                 135                 140

Xaa Xaa Xaa Xaa Xaa Xaa Xaa Xaa Asn Asn Tyr Phe Ser Val Gly Pro
145                 150                 155                 160

Asp Ala Xaa Met Ala Xaa Xaa Phe His Xaa Xaa Arg Glu Xaa Xaa Pro
                165                 170                 175

Ser Leu Phe Ser Ser Arg Xaa Leu Asn Lys Xaa Val Tyr Xaa Xaa Xaa
            180                 185                 190

Xaa Xaa Xaa Xaa Xaa Xaa Xaa Xaa Xaa Lys Xaa Leu Xaa Xaa Xaa
        195                 200                 205

Xaa Xaa Leu Glu Leu Asp Gly Xaa Xaa Xaa Xaa Xaa Xaa Xaa Xaa

```
                210               215                  220
Xaa Xaa Leu Xaa Gly Ile Ile Xaa Leu Asn Ile Gly Xaa Xaa Xaa Gly
225                 230                 235                 240

Gly Xaa Arg Xaa Trp Glu Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa Xaa
                260                 265                 270

Xaa Xaa Xaa Xaa Xaa Xaa Xaa Xaa Xaa Xaa Xaa Asp Xaa Leu Leu
                275                 280                 285

Glu Val Val Gly Xaa Xaa Xaa Xaa Xaa Xaa Xaa Xaa Xaa Xaa Xaa Xaa
                290                 295                 300

Xaa Xaa Xaa Xaa Xaa Xaa Arg Ile Xaa Gln Ala Xaa Xaa Val Xaa Xaa
305                 310                 315                 320

Xaa Xaa Xaa Xaa Xaa Xaa Xaa Pro Met Gln Val Asp Gly Glu Pro Trp
                325                 330                 335

Xaa Gln Xaa Pro Xaa Xaa Val Xaa Ile Xaa His Lys Thr Xaa Ala Xaa
                340                 345                 350

Met Leu Xaa Xaa Xaa Xaa
        355

<210> SEQ ID NO 32
<211> LENGTH: 49
<212> TYPE: PRT
<213> ORGANISM: Homo sapiens

<400> SEQUENCE: 32

His Gly Trp Arg Asp Thr Asp Leu Phe Ser Gln Pro Thr Tyr Cys Cys
  1               5                  10                  15

Val Cys Ala Gln His Ile Leu Gln Gly Ala Phe Cys Asp Cys Cys Gly
                 20                  25                  30

Leu Arg Val Asp Glu Gly Cys Leu Arg Lys Ala Asp Lys Arg Phe Gln
            35                  40                  45

Cys

<210> SEQ ID NO 33
<211> LENGTH: 53
<212> TYPE: PRT
<213> ORGANISM: Homo sapiens

<400> SEQUENCE: 33

His His Trp Ile Arg Gly Asn Val Pro Leu Cys Ser Tyr Cys Met Val
  1               5                  10                  15

Cys Lys Gln Gln Cys Gly Cys Gln Pro Lys Leu Cys Asp Tyr Arg Cys
                 20                  25                  30

Ile Trp Cys Gln Lys Thr Val His Asp Glu Cys Met Lys Asn Ser Leu
            35                  40                  45

Lys Asn Glu Lys Cys
        50
```

DIACYLGLYCEROL KINASE ISOFORMS EPSILON AND ZETA AND METHODS OF USE THEREOF

1. RELATED APPLICATIONS

This application is related to United States Provisional Application 60/016,210 of Steven M. Prescott, Michaeline Bunting, Wen Tang and Matthew M. Topham filed Apr. 22, 1996 and entitled "Molecular Cloning and Detection of Two Novel Diacylglycerol Kinase Isoforms" which provisional application is incorporated herein by this reference.

This invention was made with government support under NIH Grant No. 5 R01 CA59548-03. The government may have certain rights in the invention.

2. FIELD OF THE INVENTION

The present invention relates to the isolation and characterization of two novel diacylglycerol kinase (DAG kinase) isoforms. More specifically, the invention relates to the isolation of DAG kinase ε, DAG kinase ζ, and an alternatively spliced species of DAG kinase ζ, DAG kinase ζ-2 expressed in muscle and methods of use thereof.

3. TECHNICAL BACKGROUND

Lipids are molecules that are fundamental to the existence of all living organisms. Lipids are non-polar molecules that are water-insoluble. As such, the term lipids includes a large number of structurally distinct biomolecules, including phospholipids, glycolipids and sterols, like cholesterol.

Lipids have a variety of biological roles. First, lipids are the major component of biological membranes. Like exterior walls of houses, biological membranes are structurally organized barriers which define and separate cells from the environment and other cells. Like interior walls of houses, biological membranes are structurally organized barriers that compartmentalize and organize the cell's intracellular components.

Biological membranes, however, are not impervious walls. Instead, they are highly selective permeable barriers which regulate the quality and quantity of molecules which are allowed to pass through the membrane. The cell membrane, for example, tightly regulates the amount of water, ions and sugar which can pass into the cell.

One class of lipids which is abundant in all biological membranes is phosphoglycerides. Phosphoglycerides are comprised of a glycerol (a three-carbon alcohol) backbone, two fatty acid chains (long hydrocarbon molecules), and a phosphate. The simplest phosphoglyceride that can be formed is phosphatidic acid. Phosphatidic acid has two fatty acid chains esterified to the hydroxy groups at the C-1 and C-2 positions of glycerol, respectively. The C-3 hydroxyl group of glycerol is esterified to phosphoric acid. While phosphatidic acid is not a major component of biological membranes, it is a key intermediate in the formation of structurally related phosphoglycerides such as phosphatidylethanolamine, phosphatidylserine, and phosphatidylinositol which in addition have a sugar moiety attached to the phosphate.

Second, fatty acid-containing lipids are an energy source for cells and organisms. Fatty acids in a series of biological reactions are oxidized by certain cells to yield large amounts of energy necessary to carry out essential biological functions. Fatty acids used for fuel are stored as triglycerides, also referred to as triacylglycerols, or neutral fats. Like phosphatidic acids, triglycerides have a glycerol backbone. Rather than having two fatty acid and a phosphate group, however, triglycerides contain three fatty acid chains.

Triglycerides are an efficient way to store large quantities of energy, and thus are the major energy reservoir in humans and other mammals. The complete oxidation of a typical fatty acid yields approximately 9 kcal/g, as compared to about 4 kcal/g for proteins and carbohydrates. Moreover, unlike carbohydrate energy stores, triglycerides are anhydrous (i.e., do not contain water). Consequently, a gram of triglycerides contains more than six times the energy of one gram of carbohydrate. Taken together, triglycerides account for about 80% of all the energy of an average individual.

Finally, lipids participate in cell-cell communication, differentiation and proliferation. Normal development and function in living organisms requires interactions between cells and the molecules in the surrounding environment. One way cells communicate is via molecules, called transmembrane proteins, that span the cell's biological membrane. When the portion of the transmembrane protein which is outside of the cell encounters specific molecules in the surrounding environment, it undergoes structural and conformational changes which triggers a biological cascade inside the cell.

The binding or interaction of a molecule in the environment with a transmembrane protein frequently activates a membrane-bound enzyme called phospholipase C. The activation of phospholipase C is at the center of many major biological events. For example, the activation of phospholipase C is correlated with cell proliferation. Vasopressin, prostaglandin F2, and bombesin which stimulate cell proliferation stimulate phospholipase C. In addition, phospholipase C plays a role in activation of T lymphocytes of the immune system and fertilization of eggs.

Phospholipase C exerts its biological effects by catalyzing a reaction which cleaves the sugar moiety of the cell membrane lipid phosphatidylinositol 4,5 bisphosphate. The reaction releases diacylglycerol (DAG) and inositol triphosphate. Diacylglycerol and inositol triphosphate, referred to as second messengers, in turn, activate other molecules within the cell. Diacylglycerol, for example, activates an enzyme called protein kinase C (PKC) which is central to numerous biological processes, including the regulation of cell growth and differentiation.

As illustrated in FIG. 1, DAG is at the heart of lipid mediated biological events. Diacylglycerol is a precursor to phosphatidylcholine, phosphatidylethanolamine and phosphatidylinositol which are indispensable components of biological membranes. In addition, diacylglycerol is a precursor to triglycerides biosynthesis, and therefore, is central to energy stores of organisms. Finally, diacylglycerol is a second messenger which binds and activates protein kinase C leading to numerous biological events.

The proper regulation of diacylglycerol in cells, therefore, is critical for proper biological function. Abnormally high or low levels of diacylglycerol is predicted to alter the lipid biosynthesis and the activity of enzymes that depend on diacylglycerol, like PKC. As expected, when the phosphatidylcholine biosynthetic pathway is blocked in hepatic tissues as a result of choline deficiency, diacylglycerol levels significantly increase. As a result, choline deficient hepatic tissue demonstrate enhanced PKC activity and a higher incident of spontaneous cancer. Indeed, elevated levels of diacylglycerol have been measured in ras-, sis-, src-, fms-, and erbB-transformed cells which have lost their ability to regulate growth. Similar results are observed when cells are treated with phorbol esters, a compound that, like diacylglycerol, activates PKC.

From the foregoing, it will be appreciated that it would be an advancement in the art to provide means for regulating the intracellular pool of diacylglycerol in cells. It would also be an advantage in the art to provide means for regulating cell proliferation by decreasing the pools of diacylglycerol available to activate PKC. It would be yet another advancement in the art to describe enzymes capable of decreasing the pools of diacylglycerol by converting it to phosphatidic acid. It would be a further advancement in the art to identify and disclose the native DNA sequence of various enzymes which catalyze the conversion of DAG to phosphatidic acid, thereby enabling the production of large quantities of the enzymes and their use in gene therapy. Finally, it would be an advancement in the art to provide methods of detecting the messenger RNA and protein levels of these enzymes in a cell.

Such enzymes and DNA sequences are disclosed and claimed herein.

4. BRIEF SUMMARY OF THE INVENTION

The present invention relates to two novel human DAG kinase isoforms capable of catalyzing the conversion of DAG to phosphatidic acid. The first DAG kinase isoform, DGKε, was isolated from an endothelial cell library. The cDNA is 2.6 kilobases (kb) in length and has an open reading frame of 567 amino acid residues which gives a predicted molecular mass of 64 kDa. DGKε has two distinctive zinc finger domains at its N-terminal region, but lacks the E-F hand motifs found in other mammalian DAG kinases. The DGKε catalytic domain is related to the catalytic domain of other DAG kinases and contains two ATP binding motifs.

DGKε mRNA is expressed predominantly in the testis. In one embodiment, COS-7 cells transfected with DGKε had a marked increase in DAG kinase activity. The catalytic activity of DGKε, however, is highly selective for arachidonoyl-containing species of DAG.

The second DAG kinase isoform, DGKζ, is 3.5-kb and has a predicted molecular mass of 103.9 kDa. DGKζ contains two zinc finders, an ATP binding site, and four ankyrin repeats near the carboxyl terminus. A unique feature, as compared with other DAG kinases, is the presence of a sequence homologous to the MARCKS phosphorylation site domain.

Northern blot analysis of multiple tissues, indicates that DGKζ mRNA is expressed at highest levels in brain. COS-7 cells transfected with DGKζ cDNA express 117-kDa and 114-kDa proteins that react specifically with an antibody to a peptide derived from a unique sequence in DGKζ. The transfected cells also express increased DAG kinase activity, which is not altered in the presence of R59949, an inhibitor of human platelet DAG kinase activity. DGKζ displays stereoselectivity for 1,2-diacylglycerol species in comparison to 1,3-diacylglycerol, but does not exhibit any specificity for molecular species of long chain DAGs.

Subcellular localization of DGKζ indicates the protein is localized in the nucleus. Moreover, the MARCKS domain of DGKζ is necessary and sufficient to confer nuclear localization. The nuclear targeting is regulated by PKC phosphorylation of serines within the MARCKS domain. This is the first evidence that the MARCKS domain acts as a nuclear localization signal.

Finally, a muscle specific DAG kinase, DGKζ-2, was discovered and isolated. The cDNA is 4.1 kb in length with a unique 5' sequence of 853 bp compared to endothelial DGKζ. Like DGKζ, skeletal muscle DGKζ-2 contains two zinc finders, an ATP binding site, and four ankyrin repeats near its carboxyl terminus. COS-7 cells transfected with DGKζ-2 cDNA express a 139-kDa protein that react specifically with an antibody to a peptide derived from a unique sequence in DGKζ. Like DGKζ, skeletal muscle DGKζ-2 is localized in the nucleus.

The DGKζ gene (genomic clone) was also isolated and characterized. The DGKζ gene has 32 exons, spans approximately 50 kb of genomic sequence, and maps to chromosome 11p11.2. Based on the genomic data, it was determined that DGKζ uses exons 1 and 3–32, while DGKζ-2 uses exons 2–32.

These and other objects and advantages of the present invention will become apparent upon reference to the accompanying drawings and graphs and upon reading the following detailed description and appended claims.

5. SUMMARY OF THE DRAWINGS

A more particular description of the invention briefly described above will be rendered by reference to the appended drawings and graphs. These drawings and graphs only provide information concerning typical embodiments of the invention and are not therefore to be considered limiting of its scope.

FIG. 1 is a schematic of the various metabolic fates of diacylglycerol.

FIG. 2 illustrates the primary structure of cDNA encoding human DGKε. FIG. 2A is a map of the isolated DGKε cDNA clones used to construct the full length DGKε cDNA of the present invention. FIG. 2B is the nucleotide sequence of the composite cDNA, the deduced amino acid sequence, and domains residing within human DGKε. The cysteine residues that comprise zinc finger like domains are indicated by open triangles (Δ), and the predicted zinc finger structural motifs are underlined. Residues characteristic of ATP-binding sites found in other proteins are marked with an asterisk (*). The positions of the PCR primers (GP1–GP4) are indicated with a line above the nucleotide sequence.

Figure 3A:
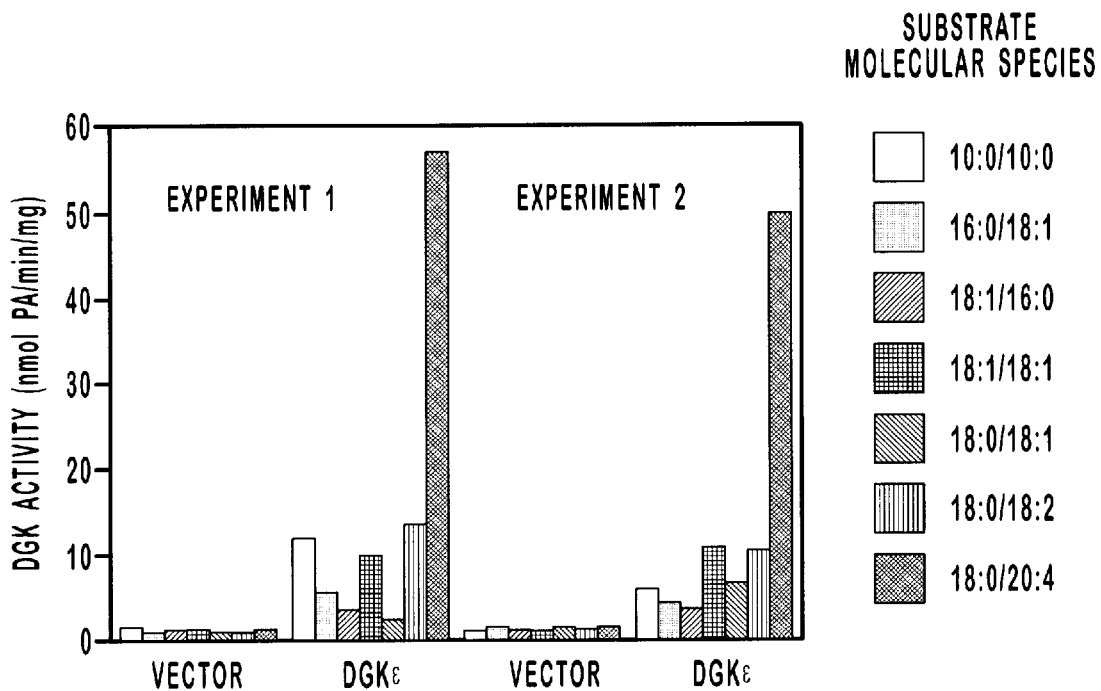
Figure 3B:
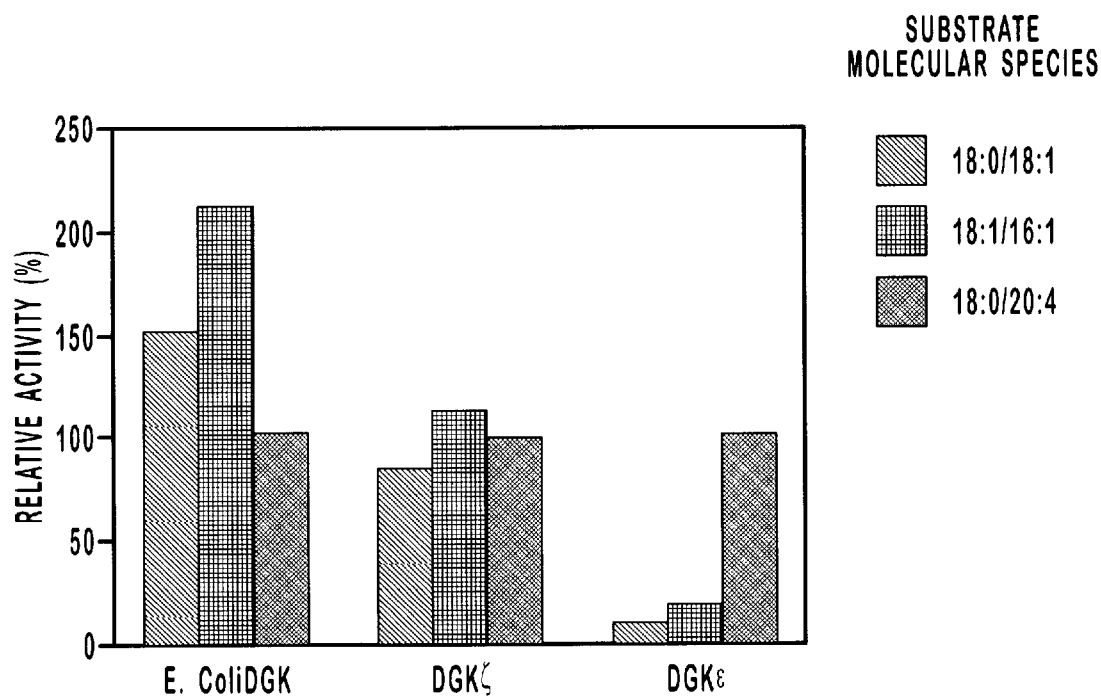

FIG. 3 is a bar graph illustrating DGKε's catalytic activity and marked specificity for arachidonate-containing diacylglycerols. In FIG. 3A, DGKε was transfected into COS-7 cells and compared to vector alone (pcDNAI). DGK activity was assayed with the following DAG substrates: 1,2-didecanoyl-sn-glycerol (10:0/10:0), 1-palmitoyl-2-cleoyl-sn-glycerol (18:0/18:1), 1-stearoyl-2-linoleoyl-sn-glycerol (18:0/18:2), and 1-stearoyl-2-arachidonoyl-sn-glycerol (18:0/20:4). The data were collected from two independent transfections, which are shown as individual experiments. FIG. 3B is a comparison of the substrate specificity of different diacylglycerol kinases. Transfections as above were carried out, but, as a control, cells were transfected with DGKζ (pcDNAI/DGKζ). Additionally, assays were performed with recombinant DGK from *E. coli* (1 μl of enzyme from the Amersham diacylglycerol assay kit). The substrates used are indicated using the abbreviations as above. For ease of comparison, the values obtained with each DGK using 1-stearoyl-2-arachidonoyl-sn-glycerol (18:0/20:4) as the substrate are shown as 100%. The activities measured using the other substrates are expressed as relative to the arachidonate-containing diacylglycerol. The values shown are the averages of two separate experiments.

Figure 4:
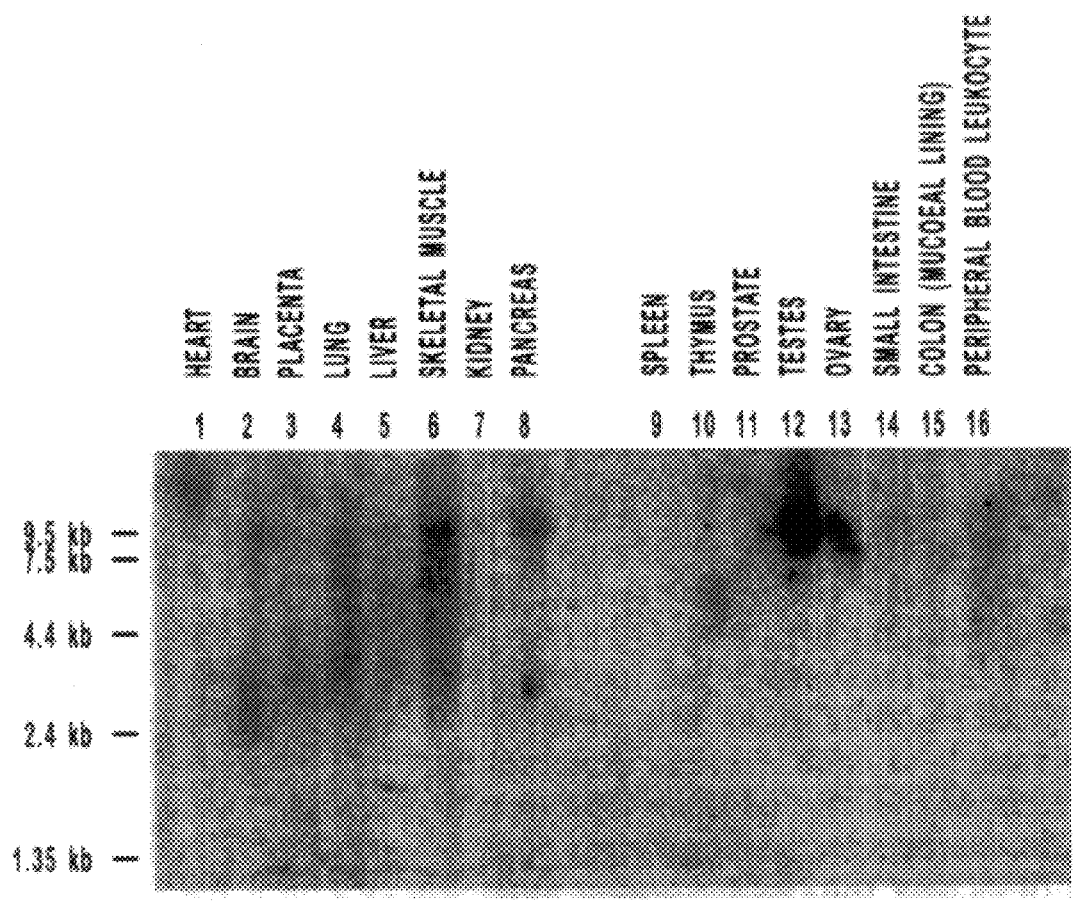

FIG. 4 is a photograph of a Northern Blot analysis of mRNA from human tissues illustrating the tissue specific expression of DGKε. Filters with poly(A+)RNA from multiple human tissues were purchased (Clontech, Palo Alto, Calif.) and hybridized with a $^{32}$P-labeled 0.9-kb ApaI/SalI fragment of pBS/DGKε. Lanes: 1, heart; 2, brain; 3, placenta; 4, lung; 5, liver; 6, skeletal muscle; 7, kidney; 8, pancreas; 9, spleen; 10, thymus; 11, prostate; 12, testis; 13, ovary; 14, small intestine; 15, colon (mucosal lining); 16, peripheral blood leukocytes.

Figures 5B, 5C:
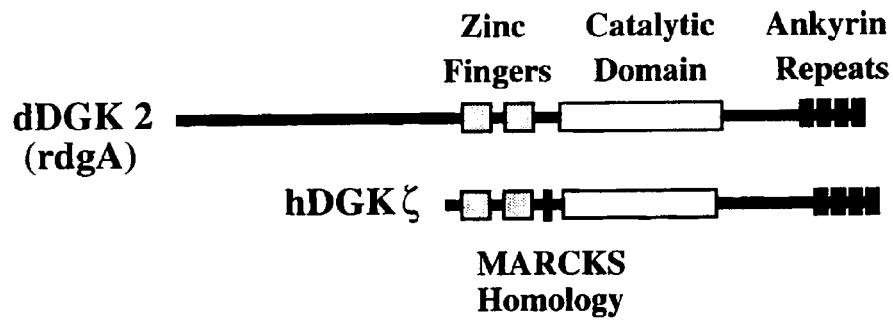

FIG. 5 is the nucleic acid sequence and deduced amino acid sequence of DGKζ. FIG. 5A is the cDNA nucleic acid sequence, the deduced amino acid sequence, and the various domains residing within DGKζ. The zinc fingers are underlined, and key cysteine and histidine residues are marked with filled diamonds (♦). Serine residues within the MARCKS homology are marked by an asterisk (*). The residues within the ATP-binding motif are double underlined. The ankyrin motifs are displayed with boxes. FIG. 5B is a comparison of the predicted protein sequences of DGKζ and rdgA. FIG. 5C is an alignment of the DGKζ carboxyl-terminal sequences with the consensus repeat found in ankyrin. Conservative substitutions were included in the alignment as shown.

Figure 6A:
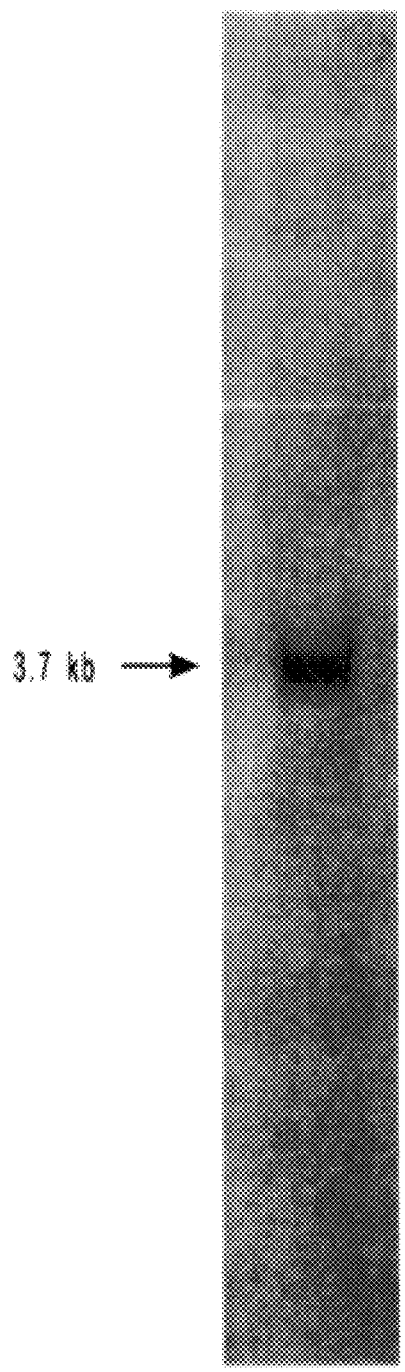
Figure 6B:
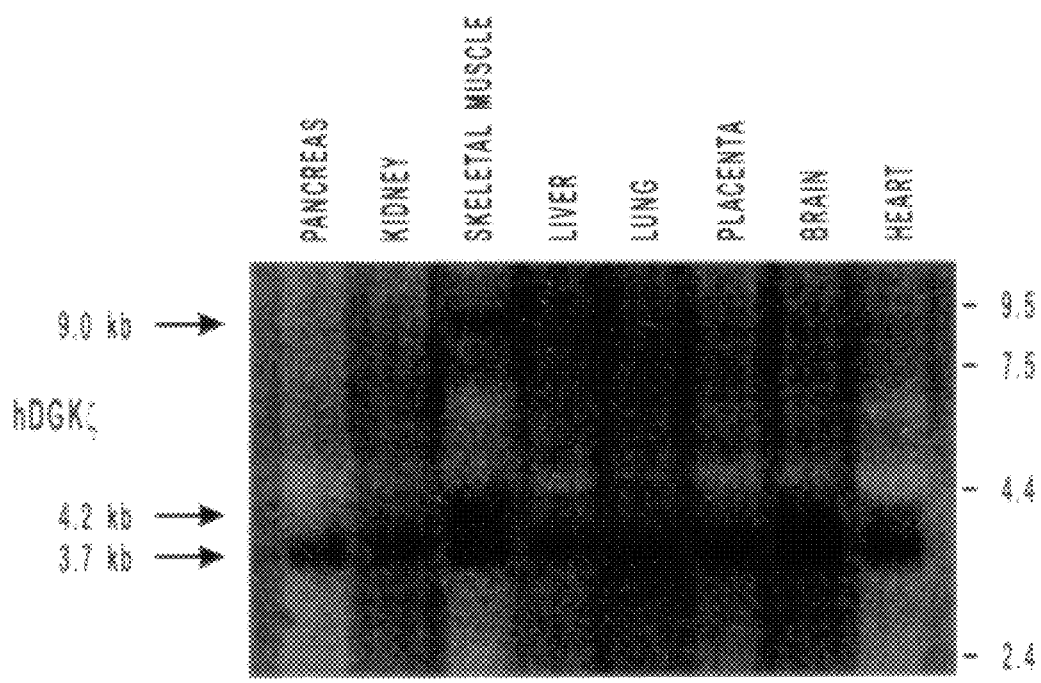
Figure 6C:
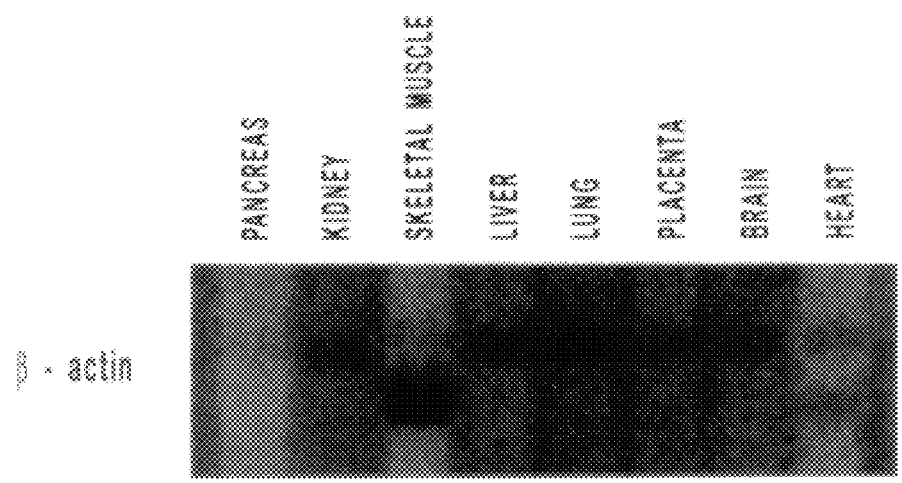

FIG. 6 illustrates the mRNA expression of DGKζ. FIGS. 6A and 6B are pictures of Northern blots illustrating DGKζ expression in human endothelial cell cultures (HUVEC) and multiple human tissue, respectively. FIG. 6C illustrates actin mRNA expression in the corresponding lanes of the human multiple tissue Northern blot which served as a positive control.

Figure 7:
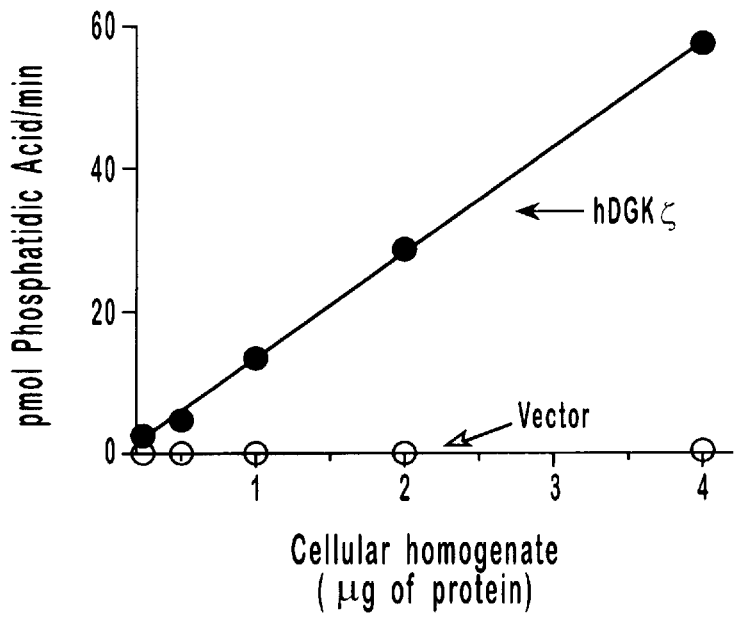

FIG. 7 is a graph illustrating the activity of heterologous expression of DGKζ. COS-7 cells which were transfected with either DGKζ (●) or vector alone (○). After 48 hrs the cells were harvested, and the indicated amounts of cellular homogenate were assayed for DGK activity using 1,2-dioleoyl-sn-glycerol as the substrate. This experiment is representative of results observed with cells from two different transfections.

Figure 8:
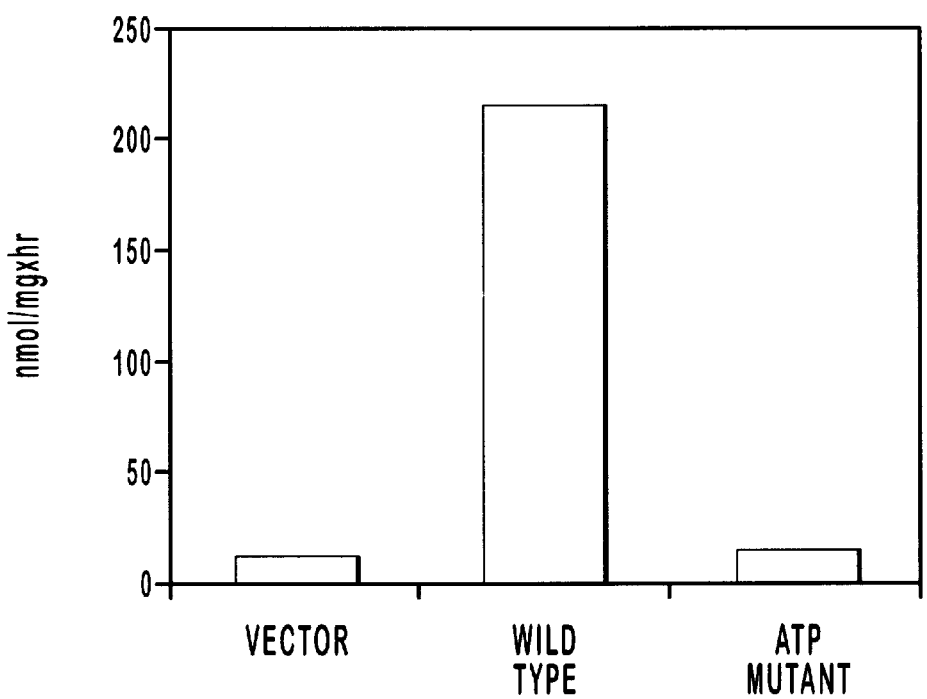

FIG. 8 is a bar graph illustrating the relative activities of native (wild-type) DGKζ versus DGKζ with its ATP binding site mutated.

Figure 9:
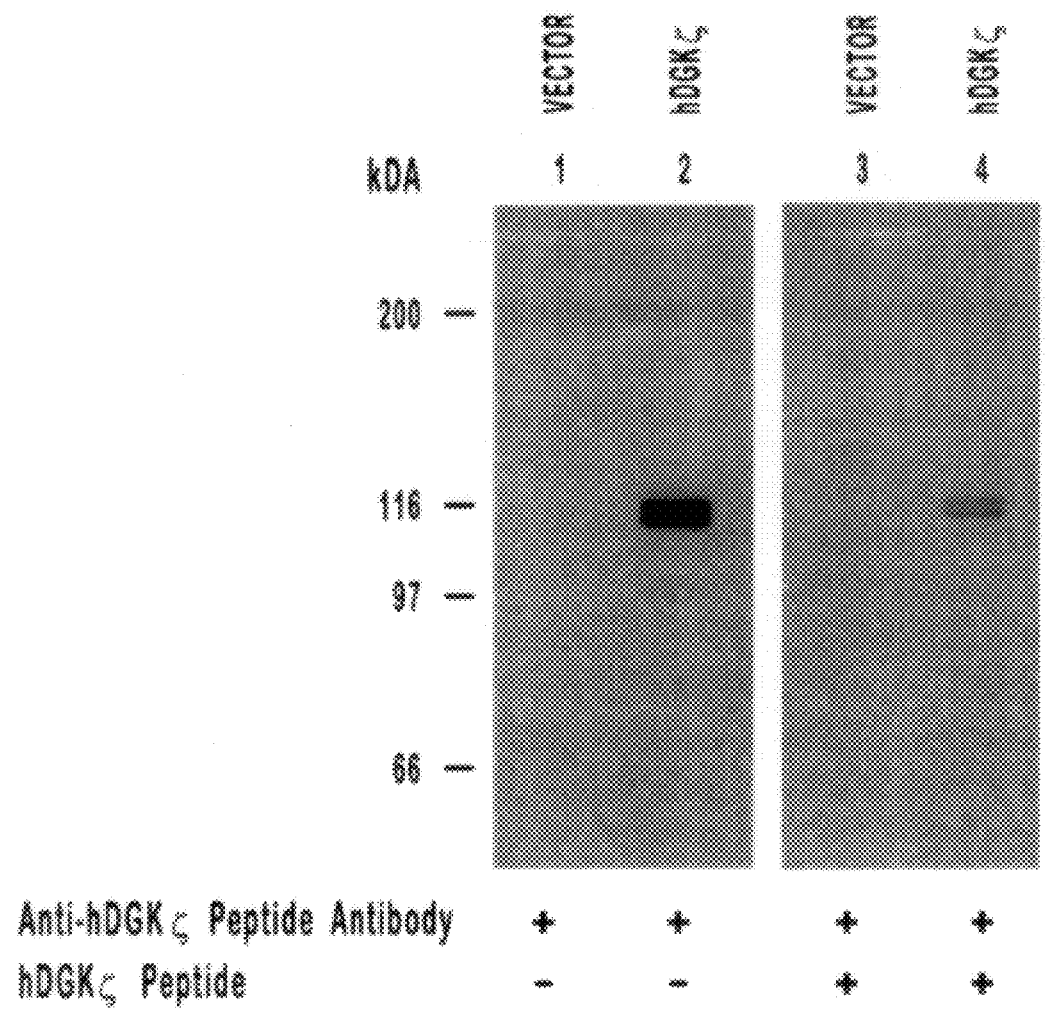

FIG. 9 is a photograph of COS-7 cells transfected with the DGKζ clone. Lanes 1 and 3 contain 25-μg samples of vector (pcDNA1/AMP) transfected COS-7 cells and lanes 2 and 4 contain 25-μg. Lanes 1 and 2 were probed with the carboxyl-terminal anti-peptide rabbit antibody. Lanes 3 and 4 were probed with the carboxyl-terminal anti-peptide rabbit antibody after preincubation with the corresponding peptide.

Figure 10:
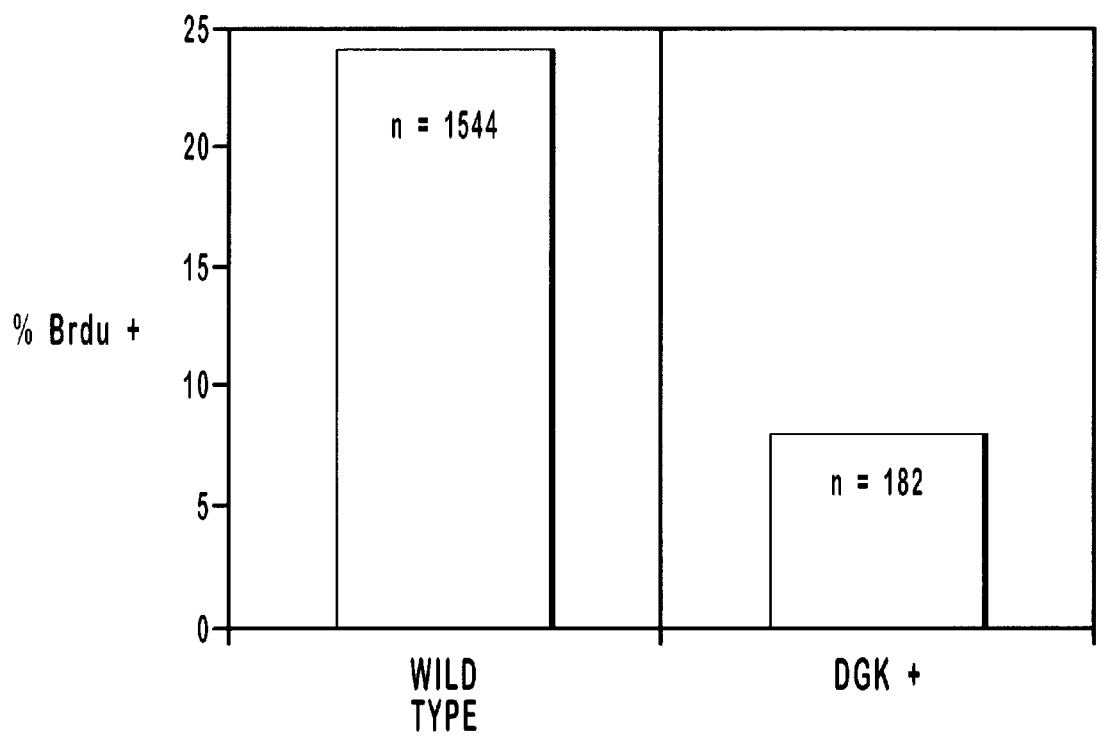

FIG. 10 is a bar graph illustrating 5-bromo-2'deoxyuridine (BrdU) uptake in COS-7 cells overexpressing DGKζ.

FIG. 11 is a photograph illustrating the subcellular localization of DGKζ. FIG. 11A is a picture of COS-7 cells transfected with a cDNA encoding fill-length DGKζ. Cells were immunostained with an anti-peptide antibody specific for DGKζ and a FITC-conjugated secondary antibody. FIG. 11B is a picture of the same field shown in FIG. 11A using a DAPI fluorescence filter. FIG. 11C is a picture of a negative control (vector alone) using a filter that detects FITC fluorescence. FIG. 11D is a picture of A172 cells immunostained with anti-DGKζ and detected with a FITC-conjugated secondary antibody.

Figure 12A:
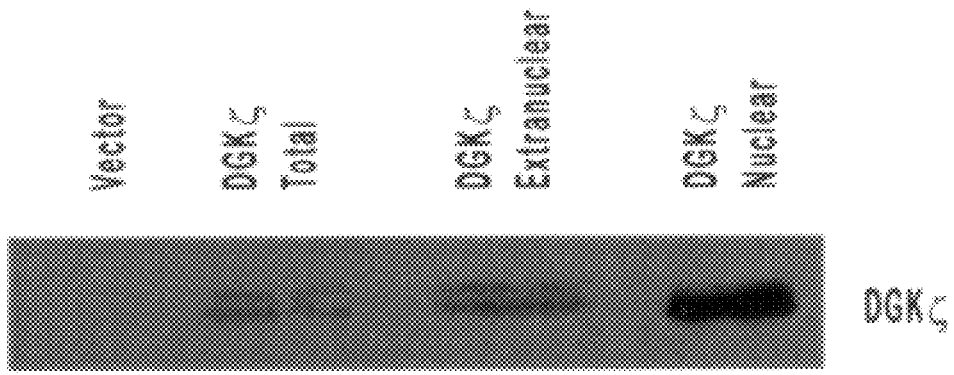
Figure 12B:
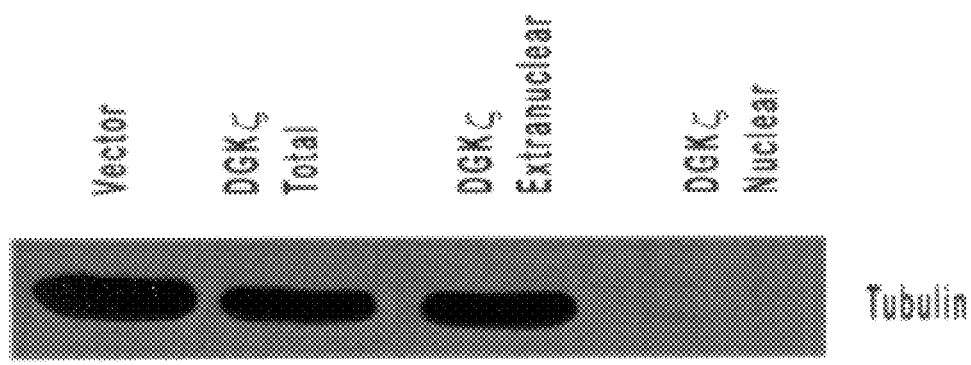

FIG. 12 is a photograph of an SDS-page gel illustrating that DGKζ appears in the nuclear fraction of transfected COS-7 cells. COS-7 cells were transfected with control vector or DGKζ cDNA and then fractioned into nuclear and extranuclear components. SDS-PAGE was performed, the gel was electroblotted, and then the blot was probed with either anti-DGKζ (FIG. 12A) or with anti-tubulin (FIG. 12B).

Figures 13A, 13B:
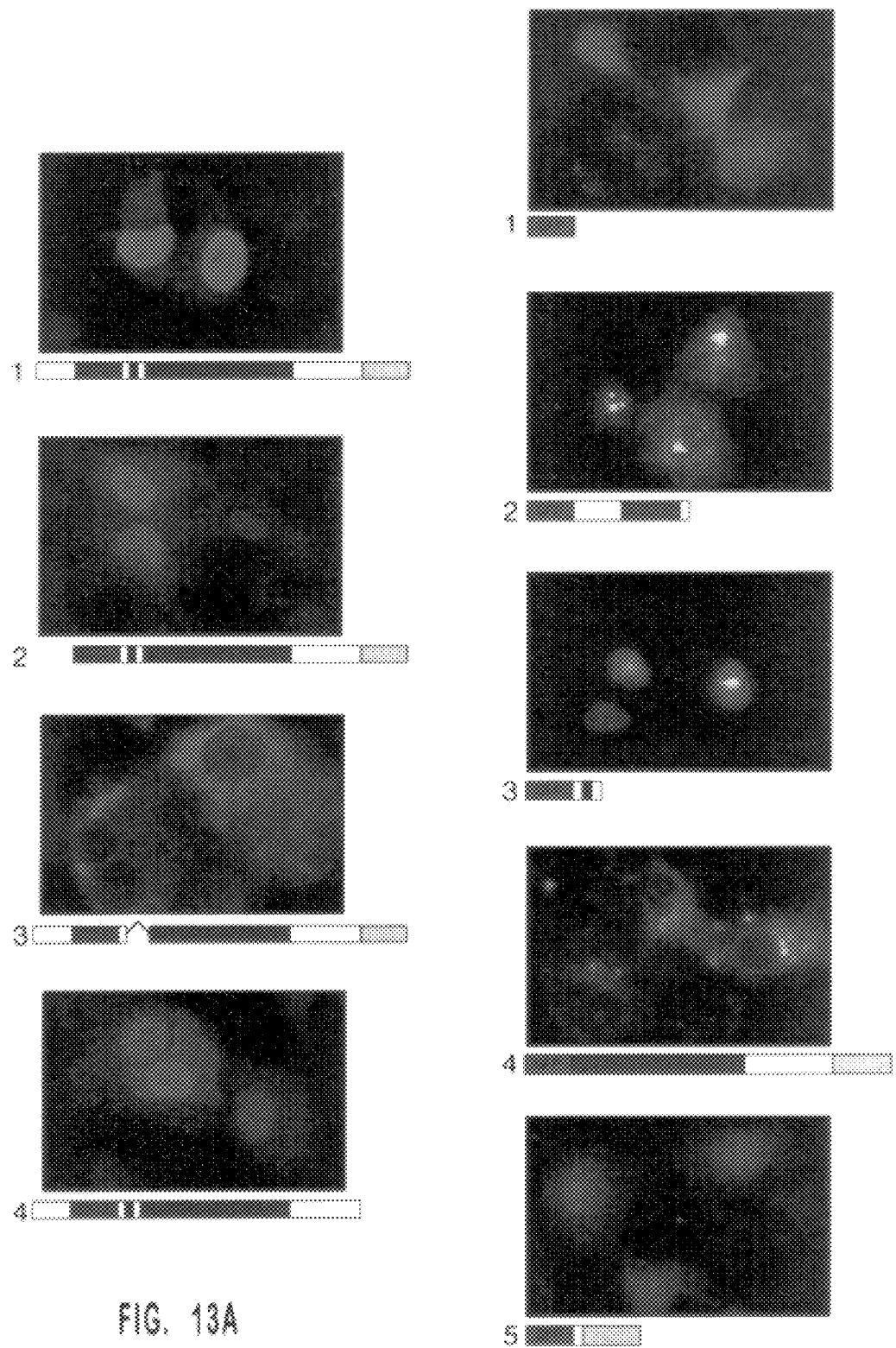

FIG. 13 is a photograph of the subcellular localization of native and mutant DGKζ illustrating that the MARCKS phosphorylation site domain of DGKζ is necessary and sufficient for nuclear targeting. FIG. 13A is a photograph of the subcellular localization of COS-7 cells which were transfected with constructs containing: native DGKζ (1), DGKζ with the amino terminus deleted (2), DGKζ with the MARCKS domain deleted (3), or DGKζ with the carboxyl terminus deleted (4). In FIG. 13B regions of DGKζ were individually fused to the carboxyl-terminus of the green fluorescent protein (GFP) and transfected into COS-7 cells. The numbers represents the following: GFP alone (1), cysteine-rich zinc finger domains (2), MARCKS phosphorylation site domain (3), catalytic domain and ankyrin repeats (4), and ankyrin repeats (5). Above each construct, its subcellular localization is shown.

FIG. 14 (A–D from top to bottom) is a photograph of the subcellular localization of the native and mutant MARCKS domains illustrating that the lysines of the MARCKS phosphorylation domain are required for nuclear targeting. A fragment of DGKζ that contains the putative MARCKS phosphorylation domain was fused to GFP. In addition, several mutant fusion proteins were constructed to test which amino acids are necessary for nuclear localization. Subcellular localization of the fusion protein is pictured above.

FIG. 15 is a graph illustrating the MARCKS domain of DGKζ is a substrate for phosphorylation by PKM (PKC lacking its regulatory domain). In FIG. 15A, both peptides were present in the reaction mixtures at final concentrations of 0.2 mM. The two reactions were carried out under identical conditions in parallel; aliquots were removed and subjected to SDS PAGE. The phosphorylated peptides were identified by autoradiography, and then cut out of the gel and subjected to scintillation counting. Blanks consisting of portions of the gel that did not contain peptide were subtracted from each value. The vertical axis indicates pooling of ATP transferred to peptide. The closed circles (●) indicate the DGK peptide; the open circles (○) indicate the DGK (A/S) peptide. In FIG. 15B, varying concentrations of DGK peptide were phosphorylated by PKM; the vertical axis refers to pmol of ATP transferred to the peptide in a 10 minute reaction. The average $K_m$ from two identical experiments was 500 nM. In FIG. 15C, varying concentrations of the DGK(A/S) peptide were phosphorylated by PKM in a 10 minute reaction, as described above. In FIG. 15D, histone HIS (final concentration: 0.2 mg/ml) was phosphorylated by PKM in a 10 minute reaction, with or without the indicated concentrations of the DGK(A/S) peptide as a potential inhibitor. A portion of each reaction was assayed by spotting onto P81 papers, followed by precipitation with trichloroacetic acid, washing and scintillation counting. Half-maximal inhibition occurred at about 800 nM peptide under these conditions.

FIG. 16 (A–D from top to bottom) is a photograph of the subcellular localization of the native and mutant MARCKS domains illustrating that the introduction of a negative charge into the phosphorylation site domain of DGKζ results in its exclusion from the nucleus. A fragment containing the native MARCKS DGKζ domain or constructs in which serines were altered to alanines, aspartates, or asparagines were fused to GFP and then transfected into COS-7 cells.

FIG. 17 is a photograph illustrating phosphorylation of the DGKζ domain by PKCα in exclusion of DGKζ from the nucleus. GFP constructs fused with either native DGKζ MARCKS domain or serine-to-alanine DGKζ MARCKS mutants were co-transfected into COS-7 cells with vector alone (FIG. 17A) or with PKCα (FIG. 17B). The cells were treated with phorbol ester (PMA) and the subcellular localization of the fusion protein was observed. Similar results were obtained with PKCγ, but not with PKC βI, βII, ε, μ, or ζ. FIG. 17C is a DGKζ MARCKS domain mutant with all serines changed to alanines that was co-transfected with PKCα into COS-7 cells. The cells were treated with PMA as above. FIG. 17D shows a western blot of total cellular homogenates (10 μg) or nuclear fractions (10 μg) from COS-7 cells where DGKζ was co-transfected with either control vector or with PKCα. Similar results were obtained by co-transfecting with PKCγ.

Figure 18:
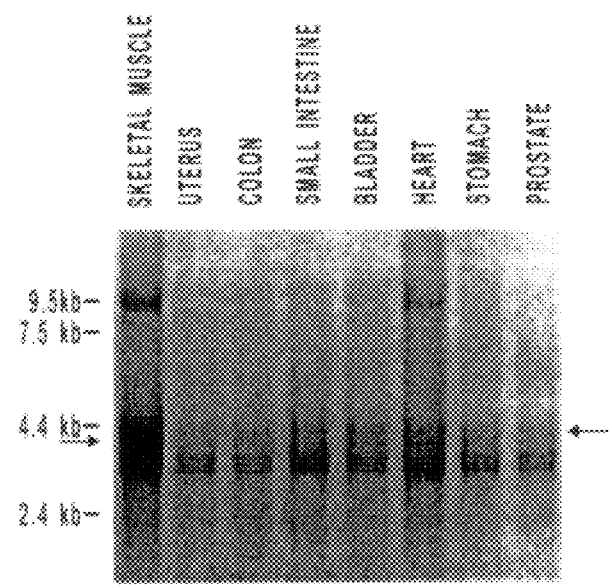

FIG. 18 is a photograph of a Northern blot illustrating DGKζ mRNA expression in muscle from human tissues. A filter with mRNA from muscle from various human tissues was probed with a fragment of the endothelial cDNA encoding DGKζ. All of the samples show a band at about 3.7 kb. In addition, there was a prominent band at 4.1–4.2 kb (denoted with arrows) in the sample from skeletal muscle. Cardiac muscle and the muscle component from bladder and small intestine showed smaller amounts of this mRNA.

Figure 19A:
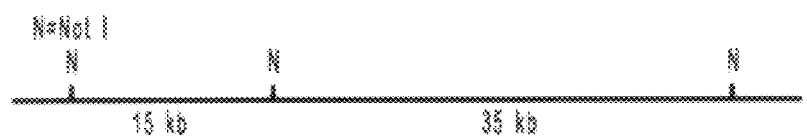
Figure 19B:
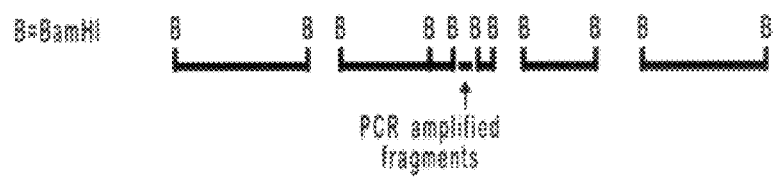
Figure 19C:
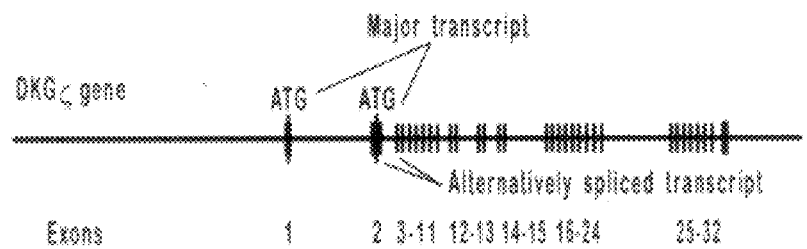

FIG. 19 is a graphic illustration of the organization of the human DGKζ gene. A genomic fragment of approximately 100 kb was isolated and shown to contain the entire coding region for DGKζ. In FIG. 19A, the positions of NotI restriction endonuclease sites (indicated by N) are shown. In FIG. 19B, the sizes and positions of BamHI fragments that hybridized with the endothelial DGKζ cDNA are shown. In FIG. 19C, the intron-exon structure of the gene and the alternative splicing that yields the two different forms are shown. The exons are represented by vertical bars and numbers.

Figure 20:
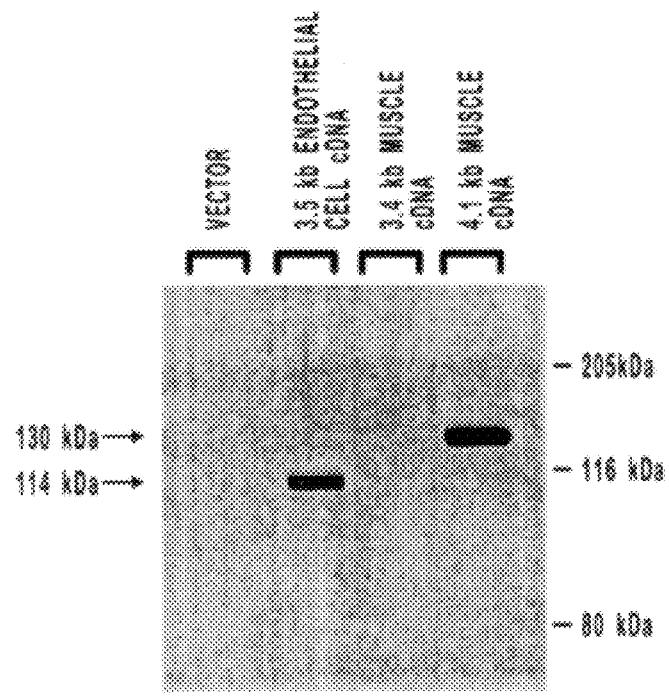

FIG. 20 is a photograph of an SDS-page gel illustrating that muscle specific DGKζ-2 expresses a 130-kDa protein. COS-7 cells were transfected with DGKζ-2 cDNA, a truncated 3.4-kb cDNA isolated from skeletal muscle, the endothelial cell DGKζcDNA, or vector alone. After 48 h, the cells were harvested and examined by Western blotting for expression. Forty micrograms of protein of the COS-7 homogenate was loaded in each lane. In control experiments, preincubation with the immuno-peptide significantly blocked the recognition of the 114- and 130-kDa proteins.

Figure 21:
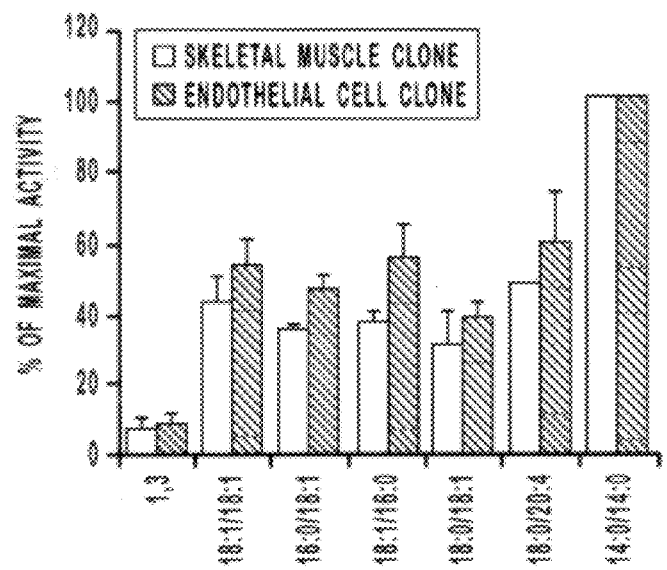

FIG. 21 is a graph illustrating the activity of DGKζ and DGKζ-2 in the presence of various DAG substrates. COS-7 cells were transfected with vectors encoding the skeletal muscle DGKζ-2 cDNA and the 3.5-kb endothelial cell DGKζ cDNA, respectively, and the homogenates were assayed for DGK activity. The total activity varied among experiments, but in each one, the homogenates from cells transfected with the two different cDNAs were assayed identically in parallel. In a typical experiment, the DGK activity was 7.5 and 6.8 nmol/mg/min of protein for the endothelial cell and muscle forms, respectively, using 1,2-dicapryl-sn-glycerol as the substrate. The results are presented as the percentage of the activity observed against 1,2-dicapryl-sn-glycerol substrate (which is reported as 100% for both forms) and represent the mean of the values obtained in two separate experiments. The error bars indicate the standard deviation. Figure legends represent the following: 18:1/18:1, 1,2-dioleoyl-sn-glycerol; 1,3, 1,3-dioleoyl-sn-glycerol; 16:0/18:1, 1-palmitoyl-2-oleoyl-sn-glycerol; 18:1/16:0, 1-oleoyl-2-palmitoyl-sn-glycerol; 18:0/18:1, 1-stearoyl-2-oleoyl-sn-glycerol; 18:0/20:4, 1-stearoyl-2-arachidonyl-sn-glycerol; 13:0/14:0, 1,2-dicapryl-sn-glycerol.

Figure 22B:
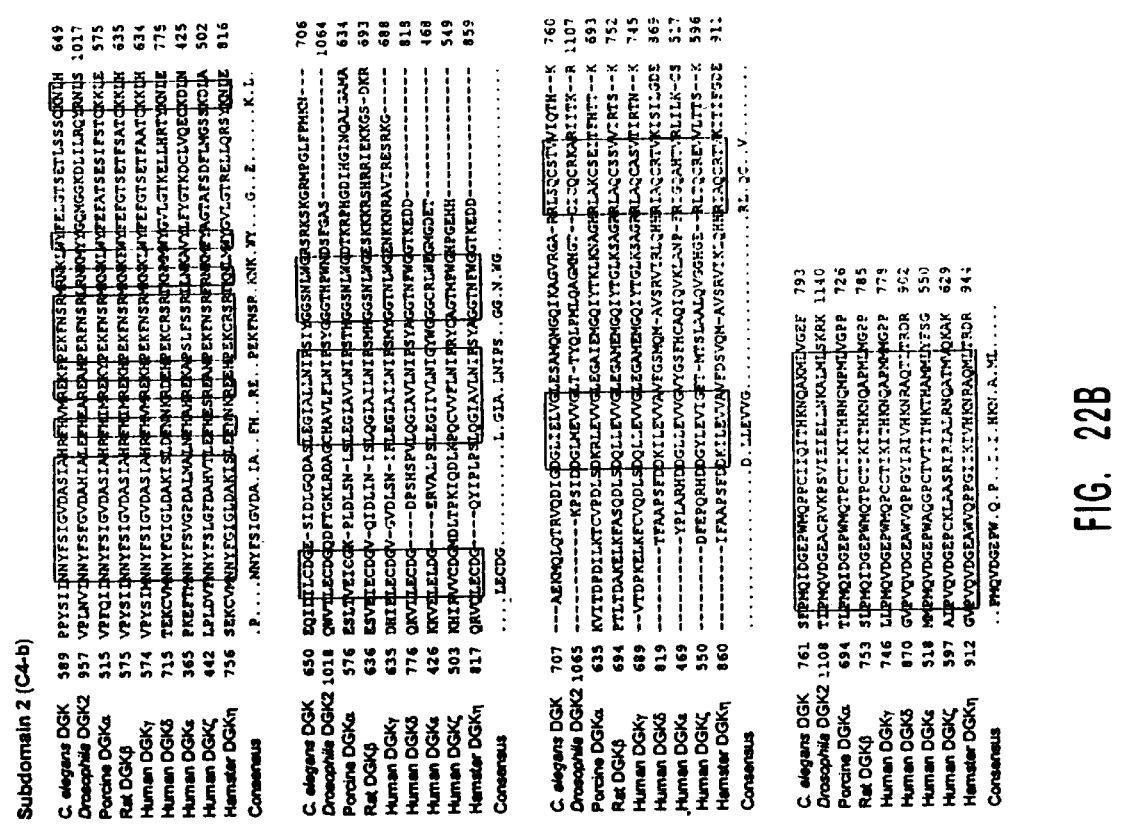

FIG. 22 is an amino acid alignment of the catalytic domains of various DAG kinases. Residues are boxed if 4 out of the 6 residues are identical. The consensus sequence is given at the bottom. Dashes (-) indicate gaps that were inserted for alignment purposes and periods (.) indicate non-conserved residues.

6. DETAILED DESCRIPTION OF THE INVENTION

The present invention relates to novel cDNA and genomic clones for two novel DAG kinase isoforms. More particularly, the present inventions relates to the isolation and characterization of DGKε (SEQ ID NO: 1), DGKζ (SEQ ID NO: 3), and DGKζ-2 (SEQ ID NO: 5).

Increased DGK activity correlate with endothelial cells quiescence. Whatley, R. E. Stroud, E. D. Bunting, M., Zimmerman, G. A., McIntyre, T. M., and Prescott, S. M. (1993) *J. Biol. Chem* 268, 16130–16138. To identify the enzyme(s) responsible for the increased DAG kinase activity, total RNA from confluent cultures of human endothelial cells was isolated and subjected to reverse transcription-PCR using degenerate oligonucleotides (primers). The degenerate primers were designed to detect conserved regions of DAG kinases. Two novel DGKs containing the conserved sequences that the degenerate primers were designed to detect, but otherwise had unique primary structure not found in other DAG kinases, were identified. One of the PCR products, which had a length of 746 bp, was named DGKε. The second PCR product had a length of 761 bp and was designated DGKζ. Further studies using DGKζ suggested that muscle cells contained a structurally related form of DGKζ. Indeed, a third isoform designated herein as DGKζ-2 or muscle specific DGKζ was identified.

In order to better understand the details of the present invention, the following discussion is divided in four sections: (1) DGKε; (2) DGKζ; (3) DGKζ-2; and (4) DGKε and DGKζ nucleic acid and protein modifications.

6.1 Diacylglycerol Kinase ε

6.1.1 cDNA Cloning of DGKε

The 746 bp PCR fragment described above was used to probe a cDNA library from human endothelial cells. The isolated cDNA molecules are depicted in FIG. 2A. Of two million plaques screened, there was one positive, DGKE1. The 5'-portion of DGKE1 was subsequently used as the probe in another round of screening, which yielded two more positive clones, DGKE2 and DGKE3, all of which were sequenced. The full-length cDNA, DGKE13, was created by combining two isolated clones, DGKE1 and DGKE3, at the BamHI site (SEQ ID NO: 1). In FIG. 2A, the length of each clone is denoted by the length of the labeled lines. The top diagram is the composite clone with the open box depicting the coding region and the solid line the non-coding region, respectively.

As illustrated in FIG. 2B, the cDNA of DGKε (SEQ ID NO: 1) has an open reading frame encoding 567 amino acids (SEQ ID NO: 2) including the initiator methionine (calculated $M_r=63,884$). The translation initiation codon corresponds well with the Kozak sequence. Kozak, M. (1987) *Nucleic Acids Res.* 15, 8125–8148. However, in the clones shown, in-frame stop codons in the 5'-untranslated region were not detected, nor were there typical polyadenylation signals in the 3'-untranslated region. In a subsequent experiment, a library from human testis (Clontech, Palo Alto, Calif.) was screened and another DGKε clone isolated with a longer 5' region. This clone contained an in-frame stop codon was found at position -129 from the initiating methionine.

The DGKε contains several previously described domains. However, DGKε clearly differs from the other cloned DGKs as it does not contain the N-terminal conserved region and E-F hand sequences found in other mammalian DGKs. Moreover, the two zinc finger-like cysteine-rich sequences found in DGKε have distinctive patterns. The zinc finger domain spanning residues $His^{60}$-$Cys^{108}$ is herein defined as DGKε's first zinc finger domain, and the zinc finger domain spanning residues $His^{125}$-$Cys^{177}$ is herein defined as DGKε's second zinc finger domain (FIG. 2B). The consensus sequence of the first zinc finger domain is: Cys-$X_2$-Cys-$X_9$-Cys-$X_2$-Cys-$X_7$-Cys-$X_9$-Cys (SEQ ID NO: 21), while the second zinc finger has the consensus sequence: Cys-$X_2$-Cys-$X_{14}$-Cys-$X_2$-Cys-$X_7$-Cys-$X_9$-Cys (SEQ ID NO: 22). These precise zinc finger motifs are not found in any other DGKs, or in PKC. In particular, the number of amino acids separating the last two cysteines in both the first and the second zinc finger-like motifs is 9 in DGKε instead of 5–8 as in most other mammalian DGKs or PKC. These features make DGKε unique among the known DGKs. In FIG. 2B, the cysteine residues that comprise zinc finger like domains are indicated by open triangles (Δ), and the predicted zinc finger structural motifs are underlined.

Additionally, DGKε contains a catalytic domain at its C-terminus roughly spanning $Pro^{219}$-$Gly^{548}$ which is herein referred to as the native catalytic domain of DGKε. Two ATP binding motifs reside within the catalytic domain. The first ATP binding motif spans residues $Gly^{279}$-$Lys^{300}$ and is herein referred to as DGKε's first ATP binding motif. The second ATP binding motif spans residues $Gly^{323}$-$Lys^{346}$, and is herein referred to as DGKε's second ATP binding motif. In FIG. 2B, conserved residues characteristic of ATP-binding sites found in other proteins are marked with an asterisk (*). The positions of the PCR primers (GP1–GP4) described above are indicated with a line above the corresponding nucleotide sequence.

6.1.2 Characterization of DGKε

In order to characterize DGKε, the full-length cDNA of DGKε was subcloned into the XhoI site of pcDNAI/Neo and transfected into COS-7 cells. Initially DAG kinase activity could not be detected. One possibility was that the DAG kinase mRNA was being rapid degraded by the cell. This hypothesis was corroborated by the 3'-untranslated region of DGKε which contains A/T-rich sequences shown to confer mRNA instability. Accordingly, the entire 3'-untranslated region and part of the 5'-untranslated region were deleted and cloned into pcDNA/Neo.

The truncated DGKε was again transfected into COS-7 cells and compared to vector alone (pcDNAI). As illustrated in FIG. 3A, DGK activity was assayed with the following DAG substrates: 1,2-didecanoyl-sn-glycerol (10:0/10:0), 1-palmitoyl-2-cleoyl-sn-glycerol (18:0/18:1), 1-stearoyl-2-linoleoyl-sn-glycerol (18:0/18:2), and 1-stearoyl-2-arachidonoyl-sn-glycerol (18:0/20:4). The data were collected from two independent transfections which are shown as individual experiments. With this DNA construct, a marked increase in DAG kinase activity was observed compared to cells transfected with vector alone when the substrate was 1-stearoyl-2-arachidonoyl-sn-glycerol (18:0/20:4).

To confirm that the activity of DGKε is highly selective for 1-stearoyl-2-arachidonoyl-sn-glycerol as compared to DAG containing other fatty acids, different molecular species of DAG in the same assay, but with different isoforms (E. coli DGK, DGKε, and DGKζ), were compared. As shown in FIG. 3B, only DGKε was selective for arachidonoyl-DAG, confirming that the substrate preference is an intrinsic property of DGKε.

Phosphatidylserine has been shown to activate and inhibit DAG kinase activity. To determine the effect of phosphatidylserine on DGKε, an additional 3.5 mm phosphatidylserine was added to the reaction mixture. The increased phosphatidylserine concentration only slightly increased the activity of DGKε. Furthermore, two compounds, R59022 and R59949, that inhibit some, but not all isoforms of DAG kinase, marginally inhibited DGKε activity. The activity in homogenates from transfected cells was inhibited by approximately 11% and 41% in the presence of 100 μm R59022 or R59949, respectively. Thus, DGKε does not seem to be a primary target for these inhibitors.

6.1.3 Tissue Distribution of DGKε

The tissue distribution of DGKε, was determined by Northern Blot analysis well known in the art. Filters with poly(A+)RNA from multiple human tissues were purchased and hybridized with a $^{32}$P-labeled 0.9-kb ApaI/SalI fragment of pBS/DGKε. (Clontech, Palo Alto, Calif.). DGKε mRNA expression in heart, brain, placenta, lung, liver, skeletal muscle, kidney, pancreas, spleen, thymus, prostate, testis, ovary, small intestine, colon (mucosal lining), and peripheral blood leukocytes was assayed. As illustrated in FIG. 4, DGKε is expressed in testis, at a lower level in ovary, and at a barely detectable level in skeletal muscle and pancreas. The mRNA of DGKε detected in Northern blotting was about 8 kb. This is much larger than the cDNA cloned which was only 2557 bp. These data suggests that the 5'-untranslated and/or the 3'-untranslated region(s) of the DGKε messenger RNA is very long.

6.2 Diacylglycerol Kinase ζ

6.2.1 Cloning of a cDNA Encoding DGKζ

As discussed above, reverse transcriptase-PCR using degenerate primers complementary to the conserved catalytic domain of known DAG kinases yielded 761 bp DNA fragment from human endothelial cells. The fragment coded for a unique DAG kinase, herein designated DGKζ. The 761 bp PCR fragment was used to screen two cDNA libraries derived from human endothelial cells, and multiple clones were identified in each. These were analyzed by restriction mapping and, in several cases, by partial sequence determination.

A clone 3.5 kb in length, which was selected for further analysis including complete nucleic acid sequencing on both strands, is shown in FIG. 5A. The DGKζ cDNA (SEQ ID NO: 3) contains a single large open reading frame encoding a 928-amino acid protein (SEQ ID NO: 4) with a predicted molecular mass of 103.9 kDa. The 5'-untranslated sequence contains a single termination codon in-frame with the predicted translation start site, which conforms reasonably well to the Kozak consensus sequence. The 3'-untranslated region includes a poly(A) tail and a sequence from $A^{3459}$ to $A^{3464}$ that is similar to the polyadenylation site consensus.

The domain structures of DGKζ differ significantly from presently known DAG kinases, particularly the mammalian isozymes α, β, and γ. Among the known mammalian isoforms, DGKζ uniquely lacks an E-F hand motif, a domain implicated in calcium binding. The most intriguing difference, however, is the presence of a sequence, $K^{259}$KKKRASFKRKSSKK$^{273}$ (SEQ ID NO: 2), which is similar to the phosphorylation site of the myristoylated, alanine-rich C-kinase substrate and is herein referred to as the DGKζ MARCKS domain. See Blacksbear, P. J. (1993) *J. Biol Chem.* 268, 1501–1504. MARCKS is a major substrate for PKC, which is activated by DAG. In FIG. 5A, serine residues within the DGKζ MARCKS domain are marked by an asterisks (*).

Moreover, DGKζ contains four tandem ankyrin repeats at the carboxyl terminus (FIG. 5A–C). In contrast to DGKζ, ankyrin consistently contains an aspartic acid or an asparagine at position 29 within this motif, whereas DGKζ has a methionine at this position in three of the four tandem repeats. Finally, in DGKζ, the N-terminal sequence $Leu^{65}$ to $Glu^{80}$ and internal sequence $Pro^{761}$ to $Pro^{779}$ scored favorably (9.5 and 16.1, respectively) in a PEST FIND program. PEST sequences are frequently observed in rapidly degraded proteins, suggesting that DGKζ may be regulated by protein degradation. In FIG. 5A, the ankyrin motifs are displayed with boxes. An alignment of the DGKζ carboxyl-terminal sequences with the consensus repeat found in ankyrin is shown in FIG. 5C. Conservative substitutions were included in the alignment as shown.

Like the other DAG kinases, DGKζ contains two zinc finger-like structures in a cysteine-rich region at the amino terminus. The zinc finger domain spanning residues $His^{98}$-$Cys^{152}$ is herein defined as DGKζ's first zinc finger domain, and the zinc finger domain spanning residues $His^{172}$-$Cys^{230}$ is herein defined as DGKζ's second zinc finger domain (FIG. 5A). The first zinc finger has a consensus sequence His-Xaa$_{11}$-Cys-Xaa$_6$-Cys-Xaa$_{12}$-Cys-Xaa$_2$-Cys-Xaa$_4$-His-Xaa$_2$-Cys-Xaa$_{10}$-Cys (SEQ ID NO: 24) and the second has a consensus sequence His-Xaa$_{11}$-Cys-Xaa$_2$-Cys-Xaa$_{19}$-Cys-Xaa$_2$Cys-Xaa$_4$His-Xaa$_4$-Cys-Xaa$_9$-Cys (SEQ ID NO: 25). In FIG. 5A, the zinc finger domains are underlined, and key cysteine and histidine residues are marked with a filled diamond (♦).

DGKζ contains a catalytic domain at its C-terminus roughly spanning $Pro^{295}$-$Lys^{626}$ which is herein referred to as the native catalytic domain of DGKζ. The DGKζ contains a single motif within the catalytic domain that conforms to an ATP binding site ($Gly^{353}$ to Lys370) which is herein referred to as DGKζ's ATP binding domain. Hanks, S. K. Quinn, A. M., and Hunter, T. (1988) *Science* 241, 42–62. In FIG. 5A, the residues within the ATP-binding motif are double underlined.

6.2.2 Expression of DGKζmRNA by Mammalian Cells

DGKζ mRNA expression in a variety of mammalian tissues was determined by Northern blot analysis. The 761-bp PCR product corresponding to DGKζ was used as a probe in Northern blots of 10 μg of total RNA. As illustrated in FIG. 6A, endothelial cells expressed a transcript of 3.7 kb that hybridized to the DGKζ. The human multiple tissue Northern blot indicated that DGKζ transcript was expressed at the highest levels in brain, but with substantial levels in skeletal muscle, heart, and pancreas. (FIG. 6B) All other tissues tested showed only low levels of expression. Actin mRNA expression in the correspondence lanes of the human multiple tissue Northern blot served as a positive control. (FIG. 6C). Moreover, as will be discussed in greater detail below, additional transcripts corresponding to 4.2 kb and 9.0 kb were detected in skeletal muscle and heart.

6.2.3 Characterization of DGKζ

To determine whether the isolated cDNA encoded a functional DAG kinase, COS-7 cells were transfected for 48 h with either vector alone (pcDNA1/AMP) or vector containing the DGKζ cDNA in the forward orientation (pcDNA1/AMP:DGKζ). Following transfections, cell homogenates were assayed for DGK activity in the presence of 1,2-dioleoyl-sn-glycerol. As illustrated in FIG. 7, cells transfected with the DGKζ cDNA (●) displayed a 267-fold increase in DGK activity, compared to vector-transfected cells (○), confirming that DGKζ encodes a functional diacylglycerol kinase. As further illustrated by FIG. 7, the formation of phosphatidic acid was linear with respect to the amount of protein assayed.

The lack of an E-F hand domain in the protein structure suggests that calcium would not influence the DGKζ activity. This was confirmed in two ways. First, despite the fact that the assay conditions used to generate FIG. 7 included EDTA and EGTA which would chelate free calcium, substantial activity was observed. Moreover, no increase in activity was observed when excess calcium (0.1–2 mm) was added to the reaction mixture at the start of the reaction.

Table I reviews the DAG specificity of DGKζ. A strong preference for 1,2-diacylglycerol over 1,3-diacylglycerol was observed, and DGKζ catalyzed the phosphorylation of a short chain DAGs (diC$_{10}$) in preference to all the long chain DAGs examined. This result likely reflects the fact that the short chain substrate is more soluble than the other substrates tested. Among the long chain diacylglycerols examined, a slight preference for 1-stearoyl-2-arachidonyl-sn-glycerol was observed. Interestingly, the observed DAG kinase activity did not distinguish between molecular species that varied only in the relative position of the fatty acids (i.e., 1-palmitoyl-2-oleoyl-sn-glycerol versus 1-oleoyl-2palmitoyl-sn-glycerol). Further, the expression of DGKζ was not significantly inhibited (94% of control) by 100 μm R59949.

TABLE I

| Substrate | nmol phosphatidic acid/mg/h |
|---|---|
| 1,2-Dicapryl-sn-glycerol | 1440 ± 42 |
| 1,2-Dioleoyl-sn-glycerol | 1021 ± 9 |
| 1,3-Dioleoyl-sn-glycerol | 110 ± 8 |
| 1-Palmitoyl-2-oleoyl-sn-glycerol | 805 ± 8 |
| 1-Oleoyl-2-palmitoyl-sn-glycerol | 856 ± 35 |
| 1-Stearoyl-2-oleoyl-sn-glycerol | 801 ± 13 |
| 1-Stearoyl-2-arachidonyl-sn-glycerol | 1106 ± 34 |

In an attempt to determine the domains within DGKζ that were essential for catalytic activity, various mutations of the native DGKζ cDNA were made using techniques well known in the art. The mutant DGKζ cDNA molecules were then cloned into expression vectors, transfected into mammalian cell lines, and the DGKζ activity was assayed.

In one embodiment, the requirement of the two zinc finger domains located 5' of the catalytic domain was tested. Using techniques well known in the art, two DGKζ cDNA mutants were constructed, each containing only one of the zinc finger domains. The relative DGKζ activity of the mutant DGKζ kinases in comparison to the native DGKζ is shown in Table II.

TABLE II

| Kinase | DGKζ activity | |
|---|---|---|
| | nmol PA†/mg/hr | Relative activity |
| Control | 2.7 | — |
| Native DGKζ | 243 | 100 |
| DGKζ Δ 3'ZFD* | 24 | 9.9 |
| DGKζ Δ 5'ZFD⁺ | 13.8 | 5.6 |

†Phosphatidic acid;
*3' zinc finger deleted;
⁺5'zinc Finger deleted

As indicated in Table II, native DGKζ displays between 10 and 20 more activity than mutants containing only one zinc finger domain. Nevertheless, mutants containing only one zinc finger domain retained significant catalytic activity. These results are consistent with reports that DAG kinase α lacking zinc fingers retains catalytic activity. See Sakane et al., "The C-terminal part of DAG kinase α lacking zinc fingers serves as a catalytic domain." (1996) *Biochem. J.* 318:583–590. Moreover, in one embodiment, the native DGKζ zinc finger domains was substituted with the zinc finger domain of another DAG kinases without lose of catalytic activity.

In another embodiment, the requirement of the tandem ankyrin repeats at the 3' end of DGKζ was tested. The ankyrin repeats of DGKζ were deleted and the catalytic activity of the truncated DGKζ was measured as before. Deletion of the ankyrin repeats did not abolish catalytic activity. The relative catalytic activities of the native and truncated forms was 1764 and 924 nmol PA/mg/hr. As is commonly done in the art, the truncated mutant was fused to an epitope tag, FLAG, in order to detect the mutant protein using common antibody techniques. When the DGK activities were normalized for protein concentration, the truncated DGKζ lacking ankyrin repeats displayed higher catalytic activity than that native DGKζ.

In yet another embodiment, the importance of the ATP binding site of the DGKζ catalytic domain to DGK activity was determined. The second conserved glycine in the native ATP binding site Gly-Asp-Gly-Thr-Val-Gly-Xaa$_{15-20}$-Lys (SEQ ID NO: 26) was mutated to an aspartic acid to give Gly-Asp-Asp-Thr-Val-Gly-Xaa$_{15-20}$-Lys (SEQ ID NO: 27). As illustrated by the graph in FIG. 8, the ATP mutant lost all catalytic activity. Interestingly, however, deletion of the 3' lysine residue typically associated with ATP binding motifs does not result in the loss of catalytic activity. Thus, either the ATP binding motif of DGKζ does not require a downstream lysine residue, or remote lysine residues can readily substitute.

6.2.4 Antibodies to DGKζ

In order to detect the DGKζ protein, polyclonal antibody were prepared based on the carboxyl-terminal peptide sequence: Cys-Leu-Glu-Asn-Arg-Gln-His-Tyr-Gln-Met-Ile-Gln-Arg-Glu-Asp-Gln-Glu. (SEQ ID NO: 7). This antibody was used to probe a Western blot containing protein form DGKζ or vector-transfected COS-7 cells. As illustrated in FIG. 9, proteins with apparent masses of 1 17 kDa were recognized by the polyclonal antibody in DGKζ-transfected cells, but were not present in control cells. Furthermore, the recognition of these proteins was blocked by preincubation of the antibody with the corresponding peptide antigen confirming that the interaction of the antibody with these proteins was specific. In subsequent studies, the expression of endogenous DGKζ in a glioblastoma-derived human cell line (A-172) by Western blotting was detected. Similarly, A-172 cells expressed two immunoreactive proteins which exhibited apparent molecular weights indistinguishable from those detected from transfected COS-7 cells.

6.2.5 Overexpression of DGKζ Inhibits Cell Proliferation

As discussed above, it has been reported that certain transformed cells and actively dividing endothelial cells exhibit higher levels of DAG and lower DAG kinase activity. Moreover, it is well known that substances such as phorbol-esters activate PKC which regulates many cellular responses, including growth and differentiation. It follows, therefore, that overexpression of DAG kinase would convert more of the intercellular DAG into phosphatidic acid, making less DAG available to activate PKC.

To test this hypothesis, COS-7 mammalian cells were stably transfected with an expression vector containing DGKζ under the control of an inducible promoter. In one embodiment, the Ecdysone Inducible System was employed. (In Vitrogen, San Diego, Calif.). The amount of cell proliferation was determined by measuring the rate of DNA synthesis using the immunochemically detectable nucleotide 5-bromo-2'deoxy-uridine (BrdU) techniques well known in the art. As graphically illustrated in FIG. 10, overexpression of DGKζ significantly inhibited BrdU uptake, and by corollary, cell proliferation.

6.2.6 Intracellular Localization of DGKζ

Figure 11A:
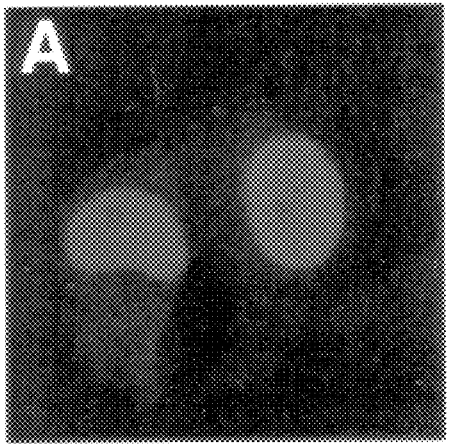
Figure 11B:
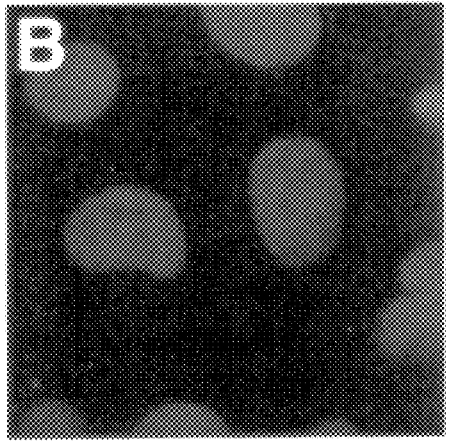
Figure 11C:
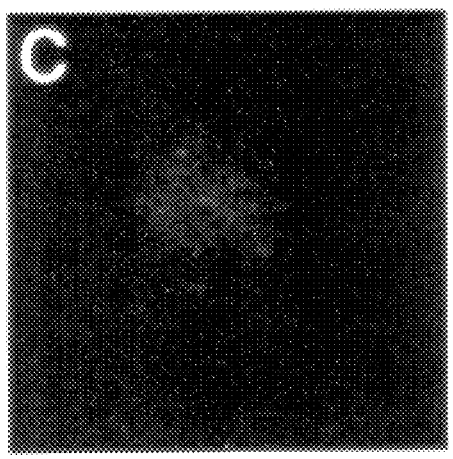
Figure 11D:
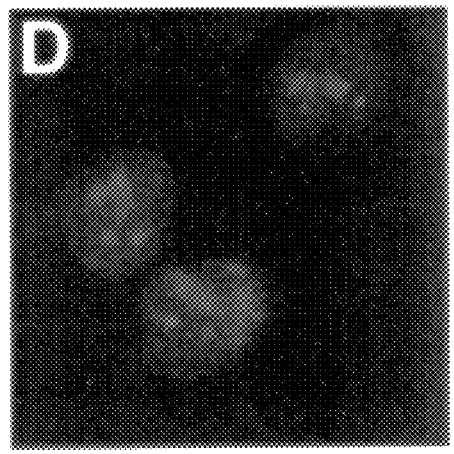

Because DGK activity may be dependent on spatially restricted DAG pools within the cell, the intracellular localization of human DGKζ was determined. In these experiments, COS-7 cells were transfected with a DGKζ cDNA and its location determined by immunofluorescent staining using antibodies raised against a peptide from DGKζ. As illustrated in FIG. 11A, the protein was located predominantly in the nucleus, but there also was light staining of the cytoplasm in an homogeneous distribution. All staining was abolished by preincubating the antibody with the peptide prior to the procedure, and a similar staining pattern was observed after transfection of a DGKζ cDNA construct that contained a FLAG epitope tag followed by detection with an anti-FLAG antibody. FIG. 11B is a picture of the same field shown in FIG. 11A using a DAPI fluorescence filter with a nuclear counterstain. FIG. 11C is a photograph of a negative control (vector alone) using a filter that detects FITC fluorescence.

Next, the subcellular localization of native DGKζ was determined. Since, as discussed above, DGKζ mRNA is predominantly expressed in brain tissue by northern blot, A172 cells, a glioblastoma-derived line, was tested and found to express DGKζ mRNA and protein. By immunofluorescence, DGKζ was found in a patchy distribution within the nucleus (FIG. 11D), occasionally with nucleolar ringing. As with transfected COS-7 cells, the cytoplasm stained lightly and homogeneously.

As an independent test of these results, and to obtain a more quantitative analysis, a subcellular fractionation followed by immunoblotting of COS-7 cells transfected with the DGKζ cDNA was performed. As illustrated in FIG. 12 A, DGKζ is localized to the nucleus, but there was a significant amount in the extranuclear fraction. In this fractionation protocol, tubulin was found only in the extranuclear fraction (FIG. 12 B), which excluded the possibility that the immunoreactivity of the nuclear fraction was the result of cytosolic contamination. The DGKζ was associated with a particulate (membrane) fraction since both the nuclear and extranuclear portions were found in the pellet following centrifugation at 100,000×g. The same results were obtained when subcellular fractionation was performed followed by immunoblotting of A172 cells.

6.2.7 Nuclear Localization Signal

As discussed above, one interesting structural feature of DGKζ is that it contains a sequence homologous to the phosphorylation site domain of MARCKS. It was hypothesized that this sequence, which is very basic, might localize the protein to the nucleus. To determine which portion of the protein accounted for the nuclear localization, DGKζ cDNAs that lacked the coding sequence for the amino terminal portion of the protein because there was a potential nuclear localization signal (NLS) in that region, or a central sequence of 100 amino acids that included the region of the DGKζ MARCKS domain, or the carboxy-terminal region that included the sequence encoding the ankyrin repeats were constructed. These plasmids were transfected into COS-7 cells and the location of the DGKζ protein was determined by immunofluorescence.

As illustrated in FIG. 13A1, A2, and A4, native DGKζ protein, and the DGKζ proteins truncated at either the amino or carboxyl terminus, respectively, were localized to the nucleus. However, the DGKζ with the deletion of the MARCKS domain was almost entirely extranuclear. Immunoblotting of subcellular fractions revealed that this deletion resulted in a greater than 70% reduction in nuclear protein compared to native DGKζ. From these observations the nuclear localization of human DGKζ was identified as the central 100 amino acid sequence containing the DGKζ MARCKS domain.

Moreover, similar results were obtained when the DGKζ domains were individually fused to the carboxyl-terminus of the green fluorescent protein (GFP) reporter and transfected into COS-7 cells, indicating that the MARCKS domain is sufficient to confer nuclear localization. FIGS. 13B(1–5) illustrates the subcellular localization of GFP alone (1), cystein-rich zinc finger domains (2), MARCKS domain (3), catalytic domain and ankyrin repeats (4), and ankyrin repeats (5). Each sequence that contained the MARCKS sequence was localized to the nucleus, while all others were predominantly extranuclear. Next, the C-terminus of the 100 amino acid sequence was truncated. A 32 amino acid fragment, which contained the MARCKS homology, still directed GFP to the nucleus. Thus, the MARCKS region is both necessary and sufficient for the nuclear localization.

To further define the nuclear signal, specific amino acids that were potentially involved in nuclear localization were mutated. As illustrated in FIG. 14, mutating the basic amino acids at either end of the DGKζ MARCKS domain abolished the nuclear localization of the GFP fusion proteins, while altering the upstream arginine amino acids only partially diminished nuclear staining. This indicates that the MARCKS homology domain of human DGKζ acts as its predominant nuclear localization signal.

The region in MARCKS that is homologous to DGKζ MARCKS domain is phosphorylated by PKC, and subsequently dissociates MARCKS from membranes by an electrostatic effect. See e.g., Swierczynski, S. L., and Blackshear, P. J. (1996). "Myristoylation-dependent and electrostatic interactions exert independent effects on the membrane association of the myristoylated alanine-rich PKC substrate protein in intact cells" *J Biol Chem* 271: 23424–23430 and publications cited therein. To test whether a similar mechanism might regulate the subcellular localization of DGKζ, the ability of PKC to phosphorylate the DGKζ MARCKS domain was determined. In these in vitro experiments, a fragment of PKC lacking its regulatory domain, protein kinase M (PCKM), was incubated with either a peptide with the native sequence of the DGKζ MARCKS domain (native peptide), $K^{256}$ASKKKKRASFKRKSSKK$^{273}$ (SEQ ID NO: 15, or a peptide in which serine 10 of the native peptide was changed to an alanine (A/S peptide) (SEQ ID NO: 16).

Figure 15A:
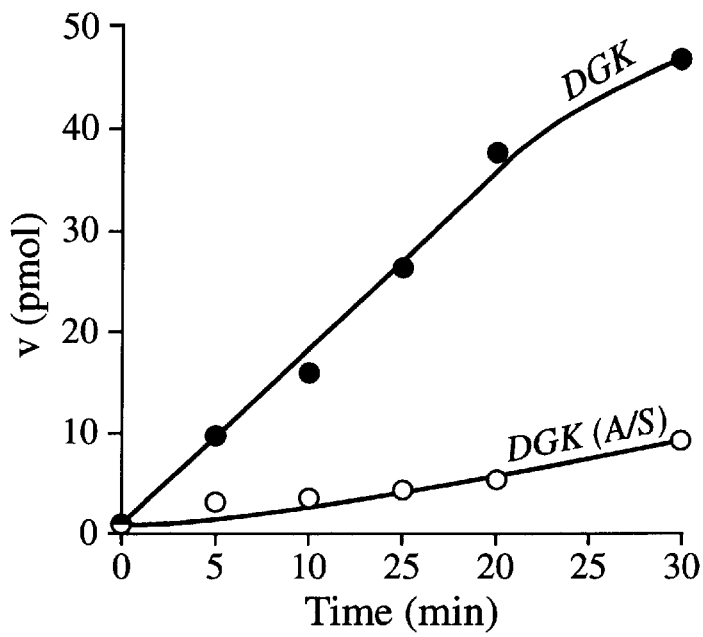

As illustrated in FIG. 15A, PKM phosphorylated both the native DGKζ and DGKζ (A/S) peptides in a linear fashion for at least 20 minutes albeit at markedly different rates. Under identical conditions and substrate concentrations (0.2 mM peptide), the phosphorylation of DGKζ (A/S) proceeded at a rate approximately ⅙that of the native peptide. This confirmed that the substituted serine in the native peptide is the primary site of PKM-dependent phosphorylation as predicted by the homology of this sequence to the high affinity PKC sites in MARCKS and MARCKS-related protein (MRP). All subsequent reactions in which the peptides were used as substrates were conducted for 10 minutes under these reaction conditions.

Figure 15B:
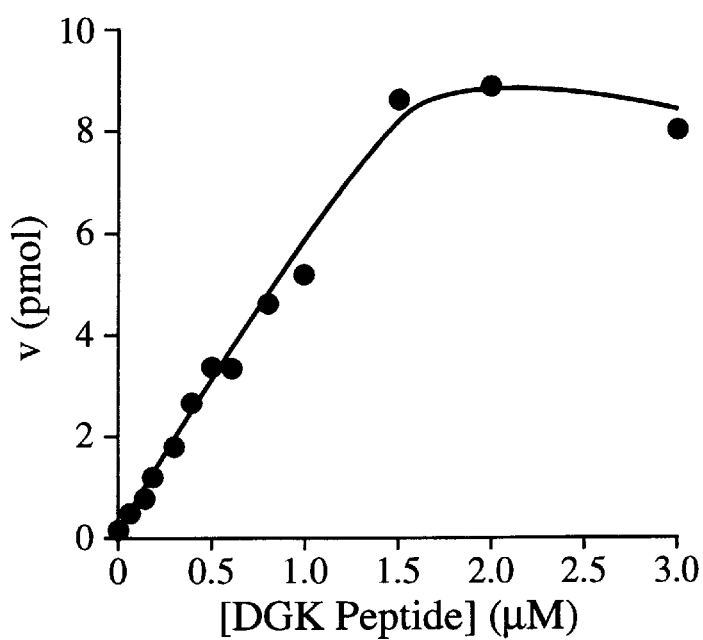

As illustrated in FIG. 15B, kinetic analysis of the native peptide revealed that the peptide was a high affinity substrate for PKM, with a $K_m$ of approximately 500 nM. This compares favorably with the $S_{0.5}$ calculated for the MARCKS and MRP synthetic peptides, which were 20 and 173 nM, respectively. In contrast to the MARCKS and MRP peptides, which are phosphorylated by PKM with pronounced positive cooperativity, the native DGKζ peptide exhibited conventional Michaelis-Menten kinetics, with a Hill constant of only 0.7.

Figure 15C:
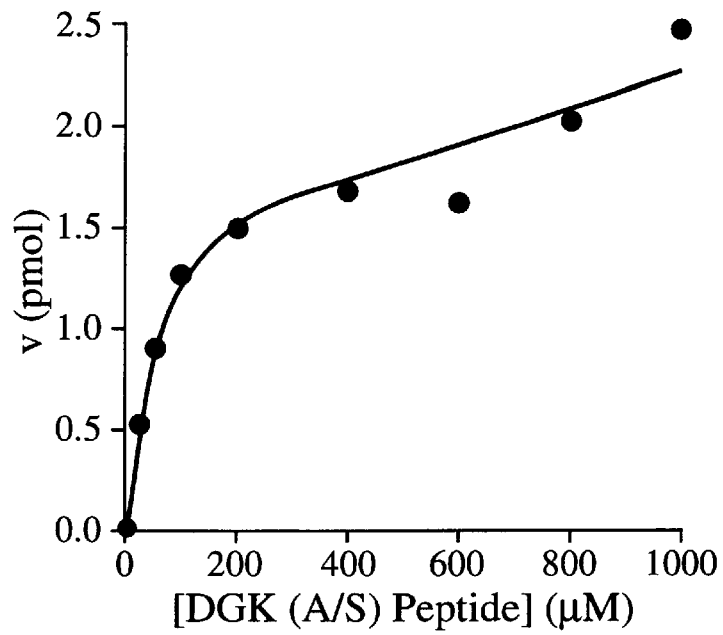
Figure 15D:
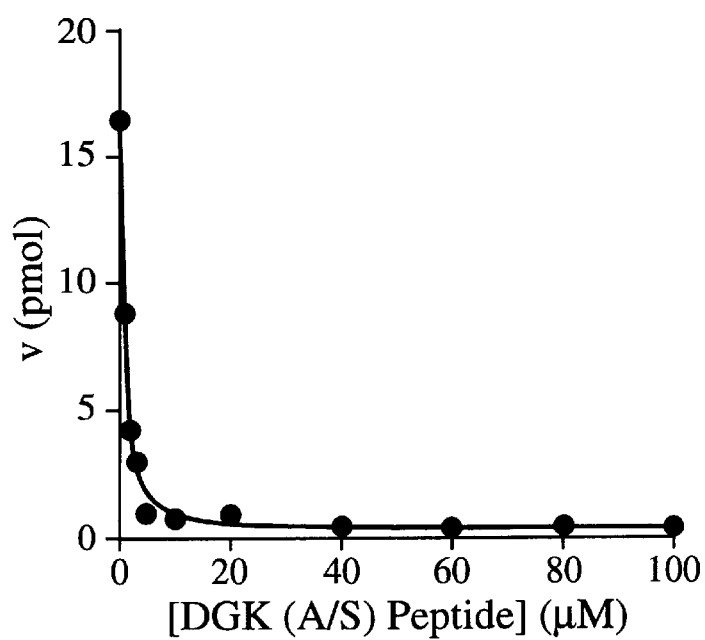

As shown in FIG. 15C, the DGK (A/S) peptide was phosphorylated by PKM with much lower affinity, and exhibited possible biphasic kinetics, suggesting the peptide was phosphorylated by PKM at one or perhaps two other lower affinity sites. Analysis of the initial portion of the rectangular hyperbola in FIG. 15C yielded a $K_m$ of approximately 50 μM. The possibility of a second, still lower affinity (Km>800 μM) site is suggested by a continuing increase in phosphorylation of the peptide by PKM (FIG. 15C). Therefore, the A/S peptide was a poorer substrate for PKM than the native peptide (500 nM for the DGK peptide vs. 50 μM for the DGKζ (A/S) peptide), but additional phosphorylation sites within this peptide are probable. However, serine 10 of the native DGKζ peptide, corresponding to Ser$^{265}$ of the DGKζ protein, is the highest affinity PKC phosphorylation site. In addition, as predicted from previous results with the MARCKS tetra-ala peptide, the DGKζ (A/S) peptide was a potent inhibitor of PKM when histone IIIS was used as a substrate (FIG. 15D), with half-maximal inhibition occurring at about 800 nM under these reaction conditions. Thus, these experiments demonstrated that the serines in the DGKζ MARCKS domain are targets for PKC.

To assess whether the phosphorylation of DGKζ by PKC has a regulatory role, a plasmid encoding a GFP fused to the 32 amino acid sequence that contained the DGKζ MARCKS domain was transfected into cells. Two peptides were used: one peptide contained the native DGKζ MARCKS domain sequence, and the other a mutant where all of the serines of the native DGKζ MARCKS domain had been changed to alanines. As illustrated in FIG. 16, both of these constructs were found in the nucleus of transfected cells. This result indicated that phosphorylation of the serines in this region is not necessary for nuclear targeting.

Next, the converse possibility was tested: that phosphorylation of one or more serines in this region resulted in an extranuclear localization. To test this the serines were changed to aspartates, which mimics the effect of phosphorylation. As illustrated in FIG. 16, in this case, the GFP fusion protein was extranuclear. As a control, a construct in which the serines were mutated to asparagines was tested. This mutation would be structurally similar to the aspartate-containing construct but without the charge that mimics phosphorylation. This protein was nuclear (FIG. 16). Thus, phosphorylation of the serines in the MARCKS homology region of DGKζ regulates the intracellular location of DGKζ: the unphosphorylated form is in the nucleus while the phosphorylated form is extranuclear.

Figure 17A:
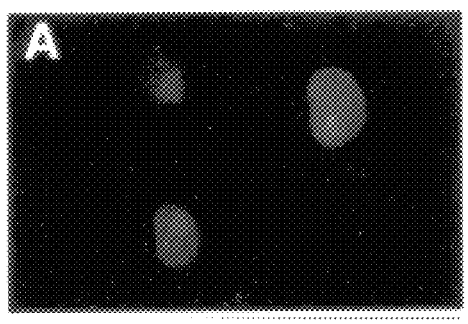
Figure 17B:
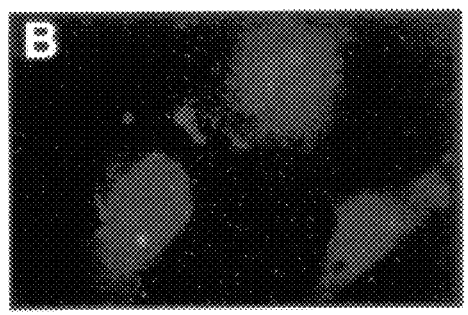
Figure 17C:
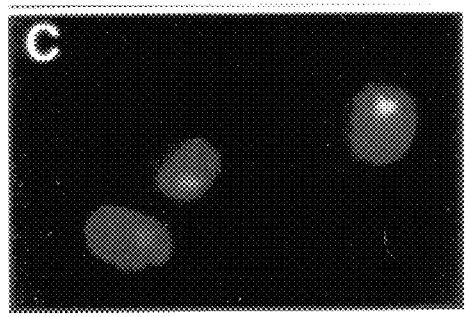

The MARCKS phosphorylation site domain was discovered on the basis of being a primary target of PKC and the above studies demonstrated the homologous region in DGKζ is an excellent substrate for PKC. Combined with the cellular localization experiments, this suggested that the location of DGKζ is likely regulated by PKC. However, there are at least 12 isoforms of PKC and it seemed likely that there could be selectivity in which of them catalyzed the phosphorylation of DGKζ. Accordingly, cells were co-transfected with cDNAs encoding different isoforms of human PKC (α, βI, βII, γ, δ, μ, or ζ) with the GFP-reporter constructs containing the native DGKζ MARCKS domain or the mutant sequence with the serines changed to alanines. As illustrated in FIG. 17A, no localization was observed in the control vector lacking the DGKζ MARCKS domain. When the native DGKζ MARCKS domain was co-expressed with PKCα or PKCγ (FIG. 17B), the reporter was redistributed from the nucleus to the cytoplasm. However, in the construct in which the serines had been replaced with alanines, the GFP fusion protein was nuclear (FIG. 17C). Co-expression of the native DGKζ sequence with other isoforms of human PKC did not influence the location of the GFP fusion protein.

Figure 17D:
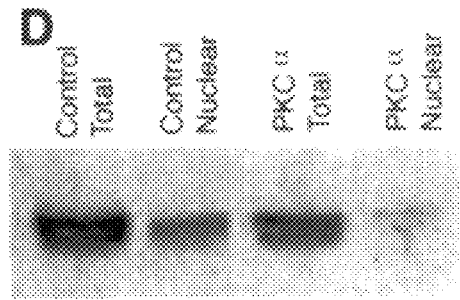

To insure that the GFP reporter constructs reflected the behavior of the native protein, experiments were performed in which the full-length coding sequence of DGKζ were co-expressed with PKCα or PKCγ and then measured the location of DGKζ by subcellular fractionation and in-immunoblotting (FIG. 17D). In these experiments, coexpression of PKCα or PKCγ reduced the nuclear localization of DGKζ by over 50%. Thus, the two different approaches demonstrate the nuclear localization conferred by the DGKζ MARCKS homology region of DGKζ is regulated by PKC, and that the regulation was specific for two isotypes of PKC.

6.3 Muscle specific Diacylglycerol Kinase ζ

6.3.1 Isolation of a Muscle cDNA Encoding a Novel DGKζ

As described above, analysis of the mRNA distribution of DGKζ in human tissues showed the predominant mRNA in most tissues was about 3.7 kb, but that skeletal and heart muscle had prominent bands of about 4.2 kb. As illustrated in FIG. 18, further examination confirmed DGKζ mRNA expression in skeletal and heart muscle, as well as smooth muscle from bladder and small intestine.

To determine whether the 4.1- to 4.1-kb transcript detected in muscle was an alternatively spliced form of DGKζ or a closely related, but different, isoform, human skeletal muscle of cDNA library were screened. Eighteen positive clones were identified; three of the clones share a 5' sequence that is different from the DGKζ cDNA isolated from an endothelial cell library described above. One of the three, which was about 4.1 kb, was analyzed by restriction digestion and fully sequenced. The clone, herein referred to as muscle specific DGKζ or DGKζ-2 (SEQ ID NO: 5), had an 853-bp-long 5' sequence that differed from the 249-bp-long 5' sequence of the endothelial cell cDNA, including the translation initiation site. The DGKζ-2 clone has a different predicted translation initiation site at position 124–126, which conforms well to the Kozak consensus sequence. DGKζ-2 contains a single large open reading frame encoding a 1,117 amino acid protein (SEQ ID NO: 6) with a calculated molecular mass of 124 kDa. From this initiation site, the DGKζ-2 mRNA produce a protein with a unique N-terminal 242 amino acid sequence that does not show significant homology to any sequences in the existing databases. Apart from this 5' region, the rest of DGKζ-2 had the same sequence as the DGKζ isolated from endothelial cells, including the polyadenylylation site.

6.3.2 Structure and Location of the Human DGKζ Gene

Three positive clones in a human genomic library that reacted with the DGKζ cDNA from human endothelial cells were identified. Based on Southern blot and sequence analysis, one clone (P 137F4) which was about 100 kb long appeared to contain the entire coding sequence and substantial additional sequence. The positions of exon-containing genomic fragments were determined by a combination of restriction endonuclease mapping and Southern blot hybridization techniques well known in the art. The physical map and genomic organization of the human DGKζ gene are illustrated in FIG. 19. The exon/intron boundaries were determined by DNA sequence analysis of BamHI fragments that hybridized to a DGKζ cDNA probe and are illustrated in Table III below.

TABLE III

| Exon | Length, bp | cDNA location | Splice acceptor | Splice donor |
| --- | --- | --- | --- | --- |
| 1 | Unknown | ...–161 |  | TCGGGCACAG/gtgaacgggg |
| 2 | 744 | –16*–728* | ctgtgcccaa/CAGCCAACCG | CCCTGTTCGC/ctaggtatag |
| 3 | 110 | 162–271 | tcctctctag/GAAAGCCATC | GACTGGAGCG/tgagtgcctg |
| 4 | 95 | 272–366 | cgtggctaga/AGTCAGCGAC | CAGGATGCTG/gtgagtgctc |
| 5 | 75 | 367–441 | cctgcagcag/AAGTCAGTGT | GCTGGAGAAG/gtgggtgggt |
| 6 | 57 | 442–498 | atgttcacag/ATAAATTTCC | TGTCCGCGAG/gtaagtgccc |
| 7 | 69 | 499–567 | tctcccccag/CCAACCTTTG | CTGTGGGAAG/gtgagaggcc |
| 8 | 72 | 568–639 | ctaccctcag/GGATTCCAGC | CAAGCAGGCA/gtgagtggtg |
| 9 | 117 | 640–756 | ctctcctcag/TACCACAGCA | GAGGCCCCAG/gtgagtactg |
| 10 | 72 | 757–828 | tcccttgcag/AATACTCTGA | AGGGCCTGAG/gtcagcccca |
| 11 | 96 | 829–924 | tgtctcccag/GAGGGCCGCT | GGGCAACCAG/gtgaacgcgg |

TABLE III-continued

| Exon | Length, bp | cDNA location | Splice acceptor | Splice donor |
|---|---|---|---|---|
| 12 | 83 | 925–1,007 | tcccatccag/GGTGCAAAGA ... | CCAAGGAGGC/gtaagtactt |
| 13 | 61 | 1,008–1,068 | atgagcccag/GCTGGAGATG ... | CGACGGCACG/gtgagcttcc |
| 14 | 114 | 1,069–1,182 | cctcccccg/GTGGGCTGGA ... | CTGGGGTGGG/gtaagcaccc |
| 15 | 141 | 1,183–1,323 | gctccccag/GGCTACACAG ... | CACCGACCGG/gtaagttggc |
| 16 | 79 | 1,324–1,402 | cttttccag/TTGCCCCTGG ... | GAGTCTCGAG/gttggcagcc |
| 17 | 56 | 1,403–1,458 | ctccacccag/AGGCCAACCC ... | CTACGCCGGG/gtgagtgggg |
| 18 | 63 | 1,459–1,521 | tctcccacag/ACAGCTTTCT ... | CCGAGTGGTG/gtgagcgggg |
| 19 | 74 | 1,522–1,595 | ccgcctccag/TGTGATGGAA ... | ACATCCCCAG/gtgaggaggg |
| 20 | 112 | 1,596–1,707 | gcctttcaag/GTACTGTGCG ... | GACGTCGTTG/gtgagtgggc |
| 21 | 200 | 1,708–1,907 | gtgcccacag/GCCGCGCTGC ... | TGCACAGCGA/gtacgtccca |
| 22 | 101 | 1,908–2,008 | tgcccgacag/CCAGCAGCCG ... | AAGGAGGCCT/gtgagtgcgg |
| 23 | 80 | 2,009–2,088 | tgttctccag/CTGTGCCGCT ... | ACTCCAGCAG/gtaaggggtg |
| 24 | 70 | 2,089–2,158 | ctctcaacag/GAGCCCGATG ... | TTCCTGGACG/gtgagtctac |
| 25 | 41 | 2,159–2,199 | ttcccacag/CCACCACTGC ... | CCGAGCCCAG/gtgagcgatt |
| 26 | 140 | 2,200–2,339 | cccccacag/GAGCACCTCA ... | CCACGCCCCG/gtgagtcctg |
| 27 | 32 | 2,340–2,371 | tctgttgcag/GTCACTGCAA ... | CCCCCTCAAG/gtgaggcctc |
| 28 | 44 | 2,372–2,415 | ttccgtgcag/GTGAAGAGCT ... | CTTCTGTAAG/gtactagctg |
| 29 | 121 | 2,416–2,536 | ctgccctcag/CTCCAGGAGC ... | CTGGACCACG/gtgagccggg |
| 30 | 34 | 2,537–2,570 | ccttctccag/CCCCCCCAGA ... | TGGAGGAAAA/gtaagtatct |
| 31 | 100 | 2,571–2,670 | gctcccccag/CGGGGAGACC ... | AGACCAGCAG/gtgagcagac |
| 32 | 732 | 2,671–3,402 | cctcctccag/GGCGACACTC ... | Polyadenylylation |

Nucleotide sequences around the exon/intron boundaries are presented. Exon sequences are shown in uppercase letters, and intron sequences are shown in lowercase letters. The locations of the splice junctions are indicated by slashes. The first base of the ATG initiation codon is designated +1.
*Positions in the 4.1-kb muscle cDNA.

The small gap between the 0.7- and 0.4-kb BamHI fragments was amplified by PCR from clone P137F4, subcloned, and sequenced. The coding sequence spans about 50 kb and has 31 exons ranging in size from 32 to 732 bp. The unique 5' sequence of DGKζ-2 is generated from an additional exon that lies between the previously determined first two exons. Thus, as illustrated in FIG. 19C, the gene has 32 exons: DGKζ employs exons 1 and 3–32, whereas the muscle form DGKζ-2 employs exons 2–32. In addition, the physical location of the DGKζ gene, was determined by fluorescence in situ hybridization with clone P137F4 and found that it localized to chromosome 11p11.2.

6.3.3 The Muscle-Specific DGKζ cDNA Encodes a Functional Enzyme Located in the Nucleus To determine whether DGKζ-2 encoded a catalytically active protein, the DGKζ-2 cDNA was subcloned into an expression vector and transfected into COS-7 cells. As illustrated by FIG. 20, proteins with apparent molecular masses of 114 and 30 kDa were recognized by an antibody to DGKζ in the cells transfected with the endothelial DGKζ cDNA and the skeletal muscle DGKζ-2 cDNA, respectively. The molecular mass of the protein expressed from the DGKζ-2 cDNA compares favorably with the predicted size of 124 kDa. Extracts from cells transfected with vector alone or with a truncated 3.4-kb cDNA from skeletal muscle did not react strongly with the antibody. Further, preincubation of the antibody with the peptide antigen blocked the recognition of the 114- and 130-kDa proteins, confirming that the interaction between the antibody and these proteins was specific. Thus, the larger, but not the smaller, clone from skeletal muscle was translated.

Next, homogenates from cells transfected with the muscle DGKζ-2 cDNA, vector alone, or the endothelial cell DGKζ cDNA were assayed for DAG kinase activity. The DAG kinase activity in cells transfected with DGKζ-2 was more than 50-fold higher than those with vector alone and similar to those transfected with DGKζ. In FIG. 21, the substrate selectivity of DGKζ-2 was compared to DGKζ. Both phosporylated 1,2-diacylglycerols, demonstrated greater activity in the presence of short chain, as compared with long chain, DAGs. However, there were no substantial differences in their use of other DAG substrates.

As discussed above, DGKζ is expressed in the cell nucleus. Because DGKζ-2 retains the MARCKS domain present in DGKζ, DGKζ-2 was also expected to be localized to the nucleus. Indeed, immunoreactive protein in DGKζ-2-transfected cells colocalized with the counterstain for DNA, establishing a nuclear location. Again, inclusion of the peptide to which the antibody had been raised completely abolished the nuclear staining.

6.4 Protein Modifications

Included within the scope of the present invention are protein modifications of the diacylglyceride isoforms. Protein modifications can be subdivided into three general classes: substitutions, additions and deletions. These general groups apply to both the nucleic acid and amino acid sequences of the DAG kinase isoforms. While protein modifications may occur naturally, most often protein modifications are deliberately engineered into the nucleic acid sequence that codes for the protein. Protein modification techniques such as site-directed mutagenesis are well known in the art and in many cases are commercially available as kits complete with instructions from, for example, Amersham and Bethesda Research Laboratories.

It is well known in the art that amino acid substitutions may be made without significantly altering the protein's function. Substitutions as defined herein are modifications made to the native nucleic acid or amino acid sequence of a protein or domain which yield a recombinant protein or domain which contains a different amino acid sequence than the native protein or domain without significantly altering its biological function. The most favorable substitutions occur when an amino acid is substituted with a similar or "conserved" amino acid. Conserved amino acids are defined as natural or synthetic amino acids which because of size, charge, polarity and conformation can be substituted without significantly affecting the structure and function of the protein. Frequently, many amino acids may be substituted by conservative amino acids without deleteriously affecting the protein's function.

In general, the non-polar amino acids Gly, Ala, Val, Ile and Leu; the non-polar aromatic amino acids Phe, Trp and Tyr; the neutral polar amino acids Ser, Thr, Cys, Gln, Asn and Met; the negatively charged amino acids Lys, Arg and His; the positively charged amino acids Asp and Glu, represent groups of conservative amino acids. This list is not exhaustive. For example, it is well known that Ala, Gly, Ser and sometimes Cys can substitute for each other even though they belong to different groups.

Conservative amino acid substitutions are not limited to naturally occurring amino acids, but also include synthetic amino acids. Commonly used synthetic amino acids are ω amino acids of various chain lengths and cyclohexyl alanine which are neutral non-polar analogs; citulline and methionine sulfoxide which are neutral non-polar analogs, phenylglycine which is an aromatic neutral analog; cysteic acid which is a positively charged analog and ornithine which is a negatively charged amino acid analog. Like the naturally occurring amino acids, this list is not exhaustive, but merely exemplary of the substitutions that are well known in the art.

Whether an amino acid can be substituted at all, or whether it can only be substituted by a conserved amino acid is best determined by comparing the amino acid sequence of one or more members of the protein family. Amino acids that are identical in all the members of a protein family usually cannot be substituted. Amino acids which are conserved can usually be substituted by other conserved amino acids without significantly affecting the protein's function. Finally, amino acids which are not conserved within a family can usually be freely substituted.

It will be appreciated by one skilled in the art, that a comparison of the amino acid sequences of the DGK isoforms of the present invention with other DGK proteins indicates that many amino acid substitutions can be made without destroying the kinases' catalytic activity. DGKε, for example, has 34%, 36%, 36%, and 32% overall identity with human DGKα, rat DGKβ, human DGKγ, and human DGKζ, respectively. Identity is defined herein as amino acid residues that are identical between two or more proteins being compared. In another example, DGKζ is overall 42% identical and 61% conserved to Drosophila DGK2.

It will also be appreciated by one skilled in the art that proteins are comprised of distinct domains For example, as discussed above, the DGKζ protein is comprised of two zinc finger domains, a MARCKS nuclear localization domain, a catalytic domain having an ATP binding motif, and four ankyrin repeats. A comparison of the amino acids residing within these domains reveals an even greater degree of conservation. For example, the catalytic domain of DGKε, has 41%, 42%, 42%, and 38% overall identity with human DGKα, rat DGKβ, human DGKγ, and human DGKζ, respectively.

As illustrated in FIG. 22, however, even within domains, subdomains, motifs and individual amino acids are identified which are highly conserved and others that are poorly conserved. It will be appreciated that using an amino acid sequence alignment like the one shown in FIG. 22, one skilled in the art can predict, with a high degree of certainty, which amino acids can be substituted without destroying the protein or domain's biological activity. For example, the Gly residues in the ATP binding motif ($G^{253}DGTVG^{258}$) (SEQ ID NO: 28) within the catalytic domain of DGKζ are identical in all the DAG kinase isolated to date. (FIG. 22). The fact that the amino acid residues that comprise the ATP binding motif have not change with evolution, strongly suggests that these exact amino acids, or at least conserved amino acids, are required at those exact positions for proper biological activity. In one embodiment above, the third Gly in the ATP binding motif was mutated to an Asp and, as expected, all catalytic activity was lost. Similar alignments for various domains can be easily generated using computer programs well known in the art, such as GenBank™/EMBL Databank comparison and alignment programs. Accordingly, the term recombinant equivalent herein refers to a deliberate, non-natural occurring nucleic acid or amino acid substitution wherein the effect on the biological activity of the resulting protein or domain, based on sequence alignment data, would have been reasonably predicted by one skilled in the art.

Protein modifications may also occur through deletions. Deletions as defined herein are modifications made to the native nucleic acid or amino acid sequence of a protein or domain which produce a recombinant protein or domain containing at least one amino acid less than the native amino acid sequence of the protein or domain without significantly altering its biological function.

As discussed above, proteins are comprised of distinct domains. Often, these domains possess unique biological functions which are manifested independently of the native protein or other domains. For example, as discussed above, the DGKζ protein is comprised of two zinc finger domains, a MARCKS nuclear localization domain, a catalytic domain having an ATP binding motif, and four ankyrin domains. The functional distinctness of these domains and the ability to delete even large portions of the protein without destroying its biological function was demonstrated in several embodiments. For example, the catalytic domain was shown not to be completely dependent on the zinc finger domains and was shown to be completely independent of the ankyrin domains. Moreover, the MARCKS nuclear localization alone was shown to be sufficient to confer nuclear localization.

Also included within the scope of the present invention are additions. Additions as defined herein are modifications made to the native nucleic acid or amino acid sequence of a protein or domain which yields a recombinant protein or domain containing at least one amino acid more than the native amino acid sequence of the protein or domain without significantly altering its biological function. In several embodiments the ability to make additions was demonstrated. For example, a FLAG epitope was added to cDNA molecules and domains for identification purposes without altering the protein or domain's biological function. Similar addition are routinely employed in the art and are not expected to alter the biological of the protein.

7. EXAMPLES

The following examples are given to illustrate various embodiments which have been made with the present invention. It is to be understood that the following examples are not comprehensive or exhaustive of the many types of embodiments which can be prepared in accordance with the present invention.

Example 1

Cell Culture—Primary cultures of human umbilical vein endothelial cells (HUVEC) were plated and maintained. Zimmerman, G. A., Whatley, R. E., McIntyre, T. M., Benson, D. M., and Prescott, S. M. (1990) *Methods Enzymol*, 187, 520–535. COS-7 cells were maintained in Dulbecco's modified Eagle's medium (Life Technologies, Inc.) Containing 10% fetal bovine serum (Hyclone Laboratories), 110 mg/liter pyruvate, 100 units/ml penicillin, and 100 µg/ml streptomycin sulfate.

Example 2

Reverse Transcription-PCR—Degenerate primers containing inosine were designed based on the amino acid sequences conserved among the sequenced catalytic domains of DGK isozymes. The forward primer (SEQ ID NO: 8):

5'-TG(C/T)GGIGGIGA(C/T)GGIACIGT(N)GG-3'

(GP-1) where I is inosine, was based on the amino acid sequence, Cys-Gly-Gly-Asp-Gly-Thr-Val-Gly (SEQ ID NO: 29), and corresponded to the amino acids $Cys^{432}$-$Gly^{439}$ of human DGKα and the corresponding sequences, following optimal alignment, of other DKGs. The reverse primer (SEQ ID NO: 9):

5'-CAIGG(C/T)TCI(A/C)C(A/G)TCIA(C/T)-(C/T)TGCAT-3' (GP-2)

was based on the amino acid sequence (SEQ ID NO: 30), MQV/IDG/VEPW, which corresponds to amino acids $Met^{695}$-$Trp^{702}$ of human DGKα and the aligned sequences of other DGKs except Drosophila DGK2. Total RNA from confluent HUVEC monolayers was isolated by the guanidinium thiocyanate method. Single strand cDNA was synthesized with 1 µg of total RNA from HUVEC at 37° C. for 1 h using oligo(dT)$_{15}$ as the primer and M-MuLV reverse transcriptase (Life Technologies, Inc.) The reverse transcription mixture was then used as the template in the PCR amplification which was performed as follows: 94° C. for 5 min., followed by 30 cycles of 94° C. for 75 s, 53° C. for 2 min., and 72° C. for 2 min., and concluding with a 5 minute incubation at 72° C. The amplified PCR fragment (about 750 bp) was gel-purified and subcloned into pBluescript II SK(+) (Stratagene) that had been cut with EcoRV and had a single T added (T-vector). The cloned fragments were sugjected to sequence analysis by the dideoxy chain termination method using a Sequenase 2.0 kit (U.S. Biochemical Corp.).

Example 3

Screening of HUVEC cDNA library—The cloned DGK fragment with a novel sequence was labeled with [α-$^{32}$P] dCTP by PCR and used as a probe to screen a HUVEC Agt11 cDNA library provided by Dr. Evan Sadler (Washington University, St. Louis). The plaques were transferred to Hybond-N nylon membrane (Amersham) and hybridized overnight at 65° C. in a solution containing 5× Denhardt's, 0.5×SSC, 0.1% SDS, and 0.1 mg/ml denatured herring sperm DNA. The filters were washed once in 2×SSC, 0.1% SDS, and once in 0.1×SSC, 0.1% SDS at room temperature for 20 min. Approximately 4×10$^6$ plaques were screened. Positive clones were subcloned into pBluescript II SK(+) and sequenced on both strands by the automated dideoxy method (ABI, University of Utah Cancer Center Core Sequencing Facility).

Example 4

COS-7 Transfection and Assay of DGK Activity—COS-7 transfection was carried out using LipofectAMINE reagent (Life Technologies, Inc.), and all steps were followed by the protocol provided by the manufacturer. After 2.5 days, the cells were harvested and lysed by sonication (twice with 5 watts for 5 s at 4° C.) in the lysis buffer (0.1 ml/35 mm well) containing 20 mm Tris-HCL, pH 7.4, 0.25 m sucrose, 1 mm EDTA, 4 mm EGTA, 1 mm dithiothreitol, 1 mm phenylmethylsulfonyl fluoride, a 20 µg/ml concentration of each: leupeptin, pepstatin, aprotinin, and soybean trypsin inhibitor. Kai, M., Sakane, F., Imai, S., Wada, I., and Kanoh, H. (1994) *J. Biol. Chem.* 269, 18492–18498. The protein concentration of the cell homogenate was determined with the BCA protein assay reagent (Pierce). In two experiments, the homogenate was separated into soluble and membrane-bound fractions by centrifugation at 100,000×g for 60 min. (4° C.). The pellet was resuspended in lysis buffer, and both fractions were assayed for DGK activity.

Since the full-length cDNA of DGKε could not be expressed in COS-7 cells, a PCR product of the DGKε cDNA lacking the 3'-untranslated region and part of the 5'-untranslated region was amplified and cloned into pcDNA/Neo (Invitrogen). The forward primer (SEQ ID NO: 10):

5'-GCATAAGCTCGATATCGAGGTATCGTCCTTG-3' (GP-3)

contained 10 random nucleotides, and EcoRV site, and 15 nucleotides complementary to nucleotide-21 to -7 of DGKε. The reverse primer (SEQ ID NO: 11):

5'-TTGTCTCGAGGTC-GACATCTATTCAGTCGCC-3' (GP-4)

contained 10 random nucleotides, a SalI site, and 15 nucleotides complementary to nucleotide 1692–1706 of DGKε. The PCR amplification was performed as follows: 94° C. for 30 s, 30° C. for 30 s, and 72° C. for 2 min. and 30 s for 5 cycles, followed by 94° C. for 20 s, 65° C. for 30 s, and 72° C. for 2 min. and 30 s for 30 cycles using Pfu (Stratagene) DNA polymerase. The PCR product was gel-purified, cut with EcoRV/SalI, and cloned into the EcoRV/XhoI side of pcDNAI/Neo (Invitrogen).

The octyl glucoside/PS mixed-micelle assay of DGK activity was performed as described. Walsh, J. P., Suen, R., Lemaitre, R. N., and Glomset, J. A. (1994) *J. Biol. Chem.* 269, 21155–21164. In brief, the assay mixture contained 50 mm MOPS, pH 7.2, 100 mm NaCl, 20 mm MgCl$_2$, 1 mm EGTA, 1 mm dithoiothreitol, 2 mm discylglycerol, 3.5 mm phosphatidylserine, 75 mm octyl-β-glucopyranoside, 500 µm [γ-$^{32}$P] ATP, and 20 µg of cellular protein in a volume of 200 µl. The reaction was initiated by the addition of [γ-$^{32}$P] ATP (20–30 µCi/µmol) and processed for 10 min at 24° C. To stop the reaction, 1 ml of MeOH, 1 ml of CHCl$_3$, 0.7 ml of 1% perchloric acid, and 50 µg of phosphatidic acid were added. The lower phase of each sample was washed twice with 2 ml of 1% perchloric acid and then dried. They were resuspended in 100 µl of 9:1 CHCl$_3$/MeOH and separated by thin layer chromatography (20×20 cm Silica 60A plates; Whatman). The plates were developed in (325:75:25) CHCl$_3$/MeOH/HOAc. The region containing phosphatidic acid was scraped, and the rediactivity was estimated by liquid scintillation spectrometry. The amount of phosphatidic acid formed per reaction was calculated by dividing the radioactivity in phosphatidic acid by the specific radioactivity of the ATP in the reaction.

Example 5

Multiple Tissue Northern Blotting—Multiple tissue Northern blots were purchased from Clontech. The ApaI/SalI fragment corresponding to nucleotides 1582–2470 of DGKε was gel-purified and labeled with [α-$^{32}$P]dCTP by random priming. Hybridization was carried out in QuickHyb (Stratagene). The conditions of hybridization and washing were described in the protocol provided by the manufacturer.

Example 6

Cell culture—COS-7 and A172 cells were cultured in DNEM with high glucose containing 110 mg/liter pyruvate, 10% fetal bovine serum, 100 units/ml penicillin, and 100 μg/ml streptomycin sulfate.

Example 7

COS-7 transfection—The human DGKζ cDNA was transfected into COS-7 cells and then were harvested as previously descβribed (Bunting et al., 1996). In the PKC cotransfection experiments, 500 ng of PKCα, βI, βII, γ, δ, ε, μ, or ζ or control vector were combined in transfection medium with 500 ng of either full-length DGKζ or a GFP construct containing the nuclear localization sequence of DGKζ. In the GFP experiments where PKC was cotransfected, the transfection medium was removed at 5 hours and replaced with 60 ng/mL phorbol 12-myristate 13-acetate (PMA) or ethanol vehicle for another 18 hours. The cells were then fixed. In the experiments where full length DGKζ was contransfected with PKC constructs, the transfection medium was removed at 5 hours and replaced with DMEM for another 18 hours. At that point, PMA (60 ng/mL) was added for 30 minutes and then the cells were washed and harvested as above.

Example 8

DGKζ CDNA constructs—The human DGKζ CDNA was expressed in pcDNA1/Amp or pcDNA3.1/Zeo(+) in the forward orientation. An amino-terminal truncation was generated by NdeI cleavage of the pcDNAI/AMP construct. The resulting CDNA encoded for an 88 kD protein with two minor products at 68 and 70 kD, presumably derived from initiation of translation at alternative downstream methionines. The carboxyl-terminal deletion was generated by engineering a FLAG tag with a stop codon at the BsaBI site (nucleotide 2325) of DGKζ, using the oligonucleotide 5'-ATGACTACAAGGACGACGATGAGAAGGC-3' (SEQ ID NO: 12) and oligonucleotide 5'CTAGGCCTTGTCATCGTCGTCCTTGTAGTCAT-3' (SEQ ID NO: 13) which were annealed and ligated into the BsaBI/Xba I-digested vector using the same procedure described for the GFP fusion constructs.

Example 9

GFP constructs—An EcoRI site was placed at the amino terminus of DGKζ using a BioRad mutagenesis kit and the following oligonucleotide (SEQ ID NO: 14):

5'-CTACCGTCCCGCGAATTCATCCG-3'.

Different coding regions were then fused to the carboxy terminus of GFP by using the following restriction sites: EcoRI/BamHI (nucleotides 94–818), BamHI/BamHI (nucleotides 819–1128), ApaI/XbaI (nucleotides 1082–3490), and SacI/XbaI (nucleotides 2140–3490). To generate the GFP NLS constructs, forward and reverse oligonucleotides corresponding to the coding region of interest, some with codons expressing altered amino acids, were synthesized at the University of Utah peptide/DNA user facility. Appropriate 3' and 5' overhanging regions were included for ligation into the ApaI/BamHI digested GFP vector. The oligonucleotides were annealed at 75° C. for two minutes and then the temperature was reduced 45° C. at 1° C./minute. The digested GFP vector was then ligated to the annealed oligos overnight at 16° C. All constructs were sequenced in both forward and reverse directions using manual dideoxy sequencing (Sequenase, U.S. Biochemical Corp.).

Example 10

Immunocytochemistry—COS-7 cells grown in 8-well chamber slides were transfected. Forty eight hours after transfection, the cells were washed three times with PBS and then fixed with 4% paraformaldehyde. They were washed again with PBS and then permeabilized with methanol (10 minutes at RT). After washing three times with PBS, they were blocked with 2% BSA and 2% goat serum in PBS for 15 minutes at 37° C. Anti-DGKζ (Bunting et al., 1996), which was affininy purified using a peptide column, was added at a 1:100 dilution and incubated for 30 minutes at 37° C. The cells were washed with PBS and then incubated with goat anti-rabbit FITC conjugate for 30 minutes at 37° C. They were then washed with PBS, stained with DAPI for one minute, and then washed with PBS again. The slides were air dried and cover slips were mounted.

Cells transfected with GFP alone were washed with PBS and then fixed for 20 minutes with 4% paraformaldehyde. They were then washed, counterstained with DAPI, washed again, and then dried and mounted.

A172 cells were stained as above except the incubation times for anti-DGKζ and goat anti-rabbit were 90 and 45 minutes respectively. Also, these incubations were carried out at room temperature.

Example 11

Nuclear isolation—COS-7 and A172 nuclear isolation was carried out as described (Payrastre et al., 1992). Western blots of cell homogenates were carried out as previously reported (Bunting et al., 1996).

Example 12

Synthesis and purification of peptides—Two peptides were synthesized and purified by reverse-phase HPLC as described previously (Verghese et al., 1994). These were an 18 amino acid peptide corresponding to residues 256–273 of DGKζ, with the sequence KASKKKKRASFKRKSSKK (DGK) (SEQ ID NO: 15); and the same peptide with an alanine substituted for the serine at residue 10 of this peptide (DGK A/S) (SEQ ID NO: 16). The purity of both peptides was confirmed by reverse phase high performance liquid chromatography as described (Verghese et al., 1994). Each peptide was dissolved in water as a stock solution of 10–30 mM, and stored at −70° C. until used.

Example 13

Phosphorylation of peptides and proteins—Peptides were phosphorylated by the purified catalytic fragment of mixed rat brain PKC isozymes (protein kinase M; PKM). In all cases involving kinetic measurements, the peptides were phosphorylated by PKM (1:120 dilution of frozen stock solution) at 30° C. All reactions were performed in the linear range of peptide phosphorylation, in an assay mixture containing 40 mM Hepes (pH 7.4), 0.25 mM EGTA, 12.5 mM MgCl$_2$, 75 μM y-[$^{32}$P]ATP, and various concentrations of peptides. In the peptide experiments, the reactions were stopped after 10 minutes by the addition of 1/5 vol of 5×SDS sample buffer, boiled for 5 minutes and then subjected to electrophoresis on 20% acrylamide gels. After the gels were dried, the phosphorylated peptides were localized by autoradiography, excised from the gel, and subjected to Cerenkov scintillation counting.

When the inhibitory effects of the DGK A/S peptide were assayed, histone IIIS (final concentration 20 μg/ml or as specified) was used as a substrate for PKM (1:80 dilution of frozen stock) in the reaction mixture described above. The reaction was linear for at least 40 minutes at 30° C.; 10 and 15 minute time points were chosen to evaluate inhibitory effects of the peptide. The peptide was added to the reaction mixture for 10 min at 30° C. in a shaking water bath before the reactions were started by the addition of Mg/ATP; samples were assayed using filter papers (P81, Whatman) and trichloroacetic acid precipitation.

Example 14

Cell Culture and Platelet Isolation—Primary cultures of human umbilical vein endothelial cells (HUVEC) were plated and maintained. COS-7 cells were cultured in Dulbecco's modified Eagle's medium with high glucose containing 110 mg/liter pyruvate, 10% fetal bovine serum, 100 units/ml penicillin, and 100 μg streptomycin sulfate. Human platelets were isolated from whole blood.

Example 15 cDNA Synthesis and Degenerate PCR—Total RNA was isolated from confluent HUVEC monoplayers, and cDNA was synthesized using Moloney murine leukemia virus reverse transcriptase and oligo(dT) as a primer. Two degenerate PCR primers (SEQ ID NO: 8): 5'-TG(C/T)GGIGGIGA(C/T)GGIACIGTNGG-3', and (SEQ ID NO: 9) 5'-GAIGG(C/T)TCI(A/C)-C(A/G)TCIA(C/T)(C/T)TGCAT-3' were used to amplify HUVEC cDNA as follows: 94° C. for 5 min., (94° C.) for 75 s, 53° C. for 2 min., 72° C. for 2 min.) 30 cycles, and 72° C. for 5 min. The resulting PCR product was gel-purified and directly cloned into the EcoRV site of pBluescript II (Strategene). Single clones were sequenced by manual dideoxy sequency (Sequence, U.S. Biochemical Corp.).

Example 16 cDNA Isolation and Sequencing—The unique 761-bp PCR product was labeled with [a-$^{32}$P]dCTP by random priming and used to screen two cDNA libraries; one from endothelial cells in the basal state, and the other from TNF-stimulated endothelial cells (from ICOS Corp., Bothell, Wash.). All colonies and plaques were transferred to Hybond-N nylon membranes (Amersham) according to manufacturer guidelines. Membranes were hybridized with the DGKζ PCR probe at 65° C. for 12 to 18 h in a solution containing 5× Denhardt's, 0.5×SSC, 0.1% SDS, and 100 μg/ml denatured herring sperm DNA. The membranes were washed, following hybridization, for 20 min in 2×SSC, 0.1% SDS and 20 min. In 0.1×SSC, 0.1% SDS at room temperature. All membranes were exposed to x-ray film for a minimum of 12 h prior to development. After screening 4×10$^5$ recombinants, 17 positive single phage clones were isolated from the unstimulated endothelial cell library. Additionally, 6 positive single clones were isolated from the TNF-stimulated endothelial cell library after screening 7.5× 10$^5$ recombinants. Two of the largest clones from the former and all of the clones from the latter library were analyzed by a combination of restriction mapping and partial nucleic acid sequencing. All of the clones that were analyzed demonstrated similar restriction maps. The largest of the representative clones from the TNF-stimulated endothelial cell library was selected for further analysis and sequenced from both strands by a combination of automated (ABI, University of Utah Cancer Core Sequency Facility) and manual diedoxy sequencing (Sequenase, U.S. Biochemical Corp.).

Example 17

Northern Blot—RNA was isolated from confluent HUVEC monolayers as described previously. Total RNA 10 μg/lane) was electrophoresed through a 0.8% agarose gel containing formaldehyde and blotted to a Hybond-N membrane by capillary transfer. Probe synthesis, hybridization, and detection methods for all Northern blots wer performed according to Boehringer Mannheim specifications for digoxigenin-labeled probes. A pBluescript II vector containing the DGKζ PCR-amplified 761-bp product was linearized with HindIII and used as a template for digoxigenin-labeled riboprobe synthesis. DGKζ-probed membranes were washed twice at room temperature in 2×SSC with 0.1% SDS for 5 min. Followed by two washes in 0.1×SSC, 0.1% SDS at 68° C. for 15 min. Followed by incubation for 1 h at 68° C. in 50% formamide, 50 mM Tris-HCl, pH 8.0, and 1% SDS prior to immunological detection. The β-action probed Human Multiple Tissue Northern blot was washed at room temperature twice in 2×SSC, 0.1% SDS for 15 min. Followed by two washes in 0.1×SSC, 01.% SDDS for 15 min prior to immunological detection.

Example 18

COS-7 Transfection—The DGKζ cDNA was expressed in pcDNA 1/AMP (Invitrogen) in the foward orientation. Each p35 dish containing COS-7 cells at 60–80% confluence was transfected with 1 μg of plasmid DNA and 5 μl of LipofectAMINE according to manufacturer specifications (Life Technologies Inc.). The cells were harvested by washing with ice-cold Hanks' balanced salt solution (Ca$^{2+}$- and Mg$^{3+}$-free) and were scraped into resuspension buffer (20 mM Tris-HCl, pH 7.4, 0.25 M sucrose, 1 mM EDTA, 4 mM EGTA, 1 mM dithiothreitol, 1 mM pheylmethylsulfonyl fluoride, 20 μg/ml each leupeptin, pepstain, aprotinin, and soybean trypsin inhibitor) 48 h following transfection. All homogenates were frozen on dry ice and stored at −70° C. until assayed.

Example 19

DAG Kinase Assay—Cell homogenates were sonicated twice with 5 watts for 5 at 4° C. The protein concentration of each cell homogenate was measured following trichloracetic acid precipitation utilizing the BCA protein assay reagent (Pierce). Each assay contained 50 mM MOPS, pH 7.2, 100 mM NaCl, 20 mM MgCl$_2$, 1 mM EGTA, 1 mM dithiothreitol, 2 mM 1,2-dieleoyl-an-glycerol, 3.5 mM phosphatidylserine, 75 mM octyl-β-glucopyranoside, 500 μM [γ$^{32}$]ATP, and 0–20 μg of cell homogenate in a volume of 200 μl. For substrate specificity experiments, various diacylglycerol species were substituted for 1,2-dioleoyl-an-glycerol. The reactions were initiated by the addition of ATP (20–30 μCi/μmol), were incubated for 10 min. At 24° C., and were terminated by the addition of 200 μl of 1% perchloric acid. Then, to each tube, we added 1.0 ml of MeOH, 1.0 ml of CHCl$^5$, 500 μl of 1% perchloric acid, and 50 μg of phosphatidic acid, vortexed them well, and centrifuged them for 10 min at 400×g. The remaining lower phase was dried under N$_2$ and resuspended in 100 μl of 9:1 CHCl$_3$/MeOH. Fifty μl of each sample were counted directly by liquid acintillation spectrometry, and the remainder was applied to a 20×20 cm Silica 60A thin layer chromatography plate (Whatman). The plates were developed in (325:75:25) $CHCl_3$/MeOH/HOAc. The region containing phosphatidic acid (as indicated by radiolabeled standards) and the remaining areas of each lane were scraped separately, and the radioactivity was estimated by liquid scintillation spectrometry. The amount of phosphatidic acid formed per reaction was calculated as [2(direct count)(PA cpm)(total lane cpm)]×[mole ATP/cpm]. R59959 was dissolved in dimethyl sulfoxide and added to relevant enzymatic reactions just prior to the addition of ATP.

Example 20

Antibody Production and Western Blot Analysis—An anti-peptide rabbit polyclonal antibody was made by Quality Controlled Biochemicals (Hopkinton, Mass.) to the carboxyl-terminal peptide ((C)LENRQHYQMIQREDQE (SEQ ID NO: 7)). This peptide corresponds to DGKζ residues $Leu^{910}$ to $Glu^{925}$ with an additional N-terminal cysteine. The extra cysteine residue was used to couple the peptide to a carrier protein, keyhole limpet hemocyanin, prior to immunization. The antibody was isolated by precipitation with caprylic acid from rabbit serum and dialyzed overnight in phosphate-buffered saline at 4° C. Samples from transfected cells (25 μg of protein) were loaded on a 7.5% acrylamide SDS-polyacrylamide gel electrophoresis gel following electrophoresis gel and, following electrophoresis, were transferred to polyvinylidene difluoride. The lane corresponding to the molecular weight standards (Bio-Rad) was cut from the blot and stained with 0.4% Ponceau red, 0.3% trichloroacetic acid and destained in water. The primary antibody was diluted with an equal volume of either phosphate-buffered saline or 100 μg/ml peptide and incubated for 30 min. at room temperature prior to incubation with the membrane. All subsequent incubation steps were performed at room temperature while shaking. Each membrane was first blocked in for 2 h in 100 ml of TBST (50 mm Tris-HCl, pH 7.5, 250 mm NaCl, 0.1% Tween 20) containing 5% nonfat dry milk. Each membrane was then incubated with the anti-peptide antibody (1:1000 dilution) in 20 ml of TBST with 5% nonfat dry milk for 1 h. The membranes subsequently were washed 5 times each for 10 min in 100 ml of TBST containing 5% nonfat dry milk. The membranes then were incubated for 1 h with a goat $F(ab')_2$ anti-rabbit immunoglobulin antibody at a 1:2000 dilution in TBST with 5% nonfat dry milk. This secondary antibody had been affinity-isolated preadsorbed with human immunoglobulin, and conjugated with horseradish peroxidase. The membranes were subsequently washed twice for 20 min. and then twice for 10 min, with 100 ml of TBST. The membranes were then developed with the ECL detection reagent (Amersham) according to manufacturer specification.

Example 21

Isolation of P1 Genomic Clone of DGKζ—Replica membranes of P1 human genomic library (University of Utah Genomics Core Facility) were screened with a 2-kb HindIII fragment of the human DGKζ cDNA that had been labeled with [$\alpha^{32}P$]dCTP by hexanucleotide random priming. Membranes were prehybridized (4 h; 42° C.) in 5× standard saline citrate (SSC/10× Denhardt's solution/0.05 M sodium phosphate, pH 6.7/500 μg/ml denatured human DNA/5% Dextran/50% formamide/0.5% SDS. Hybridization was performed (overnight; 42° C.) in the same solution. The filters were washed once in 2×SSC/0.01% SDS and then in 0.1×SSC/0.1% SDS (20 min each; both at room temperature). Membranes were exposed to x-ray film overnight. After primary and secondary screening, three positive clones were isolated.

Example 22

Mapping of Genomic Clones and Analysis of Exon/Intron Organization—The positive P1 clones were analyzed by a combination of restriction mapping and Southern blot analysis. P1 DNA samples were digested with various restriction enzymes, separated on agarose gels, and analyzed by Southern blot hybridization using cDNA probes. Strongly positive bands were subcloned into a pBluscript II SK vector (Stratagene) and sequenced by automated dideoxy sequencing (ABI, University of Utah DNA Sequencing Core Facility). A small segment of the cDNA sequence was not present in any of the sublcones, and the PCR was performed to amplify two genomic fragments containing the missing sequence. The PCR products were subcloned into a pBluescript II SK vector for sequencing analysis. The PCR primers and were [5'-GTGCAAAGATCATCCAGTCTT-3' (SEQ ID NO: 17), 5'-TGGAGAGGATCCAGCCCACCG-3' (SEQ ID NO: 18)] and [5'-ACCCCAATCCCTCTTTCCCAG-3' (SEQ ID NO: 19), 5'-GAAAGACTGGATGATCTTTGC-3' (SEQ ID NO: 20)]. The DGKζ gene was physically mapped by fluorescence in situ hybridization using P137F4 DNA as a prove.

Example 23

Isolation and Characterization of cDNAs—One million phage recombinants were plated from a human skeletal muscle cDNA library. All plaques were transferred to Hybond-N nylon membranes (Amersham), which were screened with the previously described DGKζ cDNA. Membranes were prehybridized (4 h; 65° C.) in 5× standard saline phosphate/EDTA (SSPE)/5× Denhardt's solution/0.2% SDS/0.1% $Na_2P_4O_7$. Hybridization was performed (overnight; 65° C.) in the same solution. The membranes were washed twice in 0.6×SSPE/0.1% $Na_2P_4O_7$ (15 min; 65° C.). After primary and secondary screening, 18 positive clones were identifies; all were analyzed by restriction digestion, and those of >3 kb were sequenced.

Example 24

Cell Culture, Transfection, and DGK Activity Assay—COS-7 cells were maintained in DMEM (GIBCO/BRL) containing 10% fetal bovine serum, 100 units/ml penicillin, and 100 μg/ml streptomycin. The two alternatively spliced forms were subcloned into pcDNAI/MP (Invitrogen) in the forward orientation. COS-7 cells at 50–60% confluence in p35 dishes were transfected with 1 μg of plasmid DNA and 5 μl of Lipofectamine for 5 h according to the manufacturer's guidelines. After 48 h, the cells were washed with PBS and were scraped into lysis buffer (20 mM Tris-HCl, pH 7.5/0.25 M sucrose/1 mM EDTA/f mM EGTA/1 mM DTT/1 mM PMSF/20 μg/ml leupeptin, pepstatin, aprotinin, and soybean trypsin inhibitor). All homogenates were frozen and stored at −70° C. until assayed; the assay was performed as described.

Example 25

Western Blotting and Immunocytochemistry—Samples from transfected cells were separated in a SDS/7.5% polyacrylamide gel, and Western blotting was performed. For immunocytochemical analysis, COS-7 cells were transfected with the alternatively spliced forms DGKζ as described above. In the following procedure, the cells were washed three times with PBS between steps. After 48 h, the cells were fixed with 3.7% paraformaldehyde (10 min) and then permeabilized with 100% methanol (5 min; room temperature). The cells subsequently were blocked in PBS with 2% BSA and 2% goat serum (15 min; room temperature) and incubated with the anti-peptide DGKζ antibody (1:100 dilution) in blocking solution (30 min; 37° C.). The cells were then incubated with a fluorescein-conjugated goat anti-rabbit immunoglobulin antibody (1:20 dilution) in blocking solution (30 immunoglobulin antibody (1:20 dilution) in blocking solution (30 min; 37° C.) in the dark. The cells were counterstained with 4',6-diamidino-2-phenylindole (1:5,000 dilution) for 1 min. The cells were photographed with fluorescent microscopy after mounting slides.

What is claimed and desired to be secured by United States Letters Patent is:

1. An isolated and purified nucleic acid sequence whose complement hybridizes to SEQ ID NO: 1 under the conditions of 65° C. overnight in a solution comprising 5×Denhardt's, 0.5×SSC, 0.1% SDS, and 0.1 mg/ml denatured herring sperm DNA, followed by washing once in 2×SSC, 0.1% SDS at room temperature for 20 minutes, and once in 0.1 X SSC, 0.1% SDS at room temperature for 20 minutes, wherein said nucleic acid sequence codes for a protein having diacylglycerol kinase enzymatic activity.

2. The nucleic acid sequence defined in claim 1 wherein said nucleic acid sequence is subcloned into a plasmid.

3. The nucleic acid sequence defined in claim 1 wherein said nucleic acid sequence is subcloned into a prokaryotic or eukaryotic expression vector.

4. The nucleic acid sequence defined in claim 1 wherein said nucleic acid sequence is stably or transiently incorporated into a prokaryotic or eukaryotic host cell.

5. An in vitro method of decreasing the intracellular levels of diacylglycerol and increasing intracellular levels of phosphatidic acid comprising introducing into a eukaryotic cell the nucleic acid sequence of claim 1.

6. An isolated and purified nucleic acid, said nucleic acid comprising nucleotides which code for the amino acid sequence of SEQ ID NO: 2.

7. An isolated and purified nucleic acid which codes for human diacylglycerol kinase ε, said nucleic acid comprising the nucleotide sequence of SEQ ID NO: 1.

8. A recombinant vector comprising the nucleic acid molecule of claim 7.

9. The recombinant vector of claim 8, wherein said recombinant vector is a plasmid.

10. The recombinant vector of claim 8, wherein said recombinant vector is a prokaryotic or eukaryotic expression vector.

11. The recombinant vector of claim 8, wherein the nucleic acid molecule is operably linked to a heterologous promoter.

12. A host cell comprising the nucleic acid of claim 7.

13. The host cell of claim 12, wherein the host cell is a eukaryotic host cell.

14. The host cell of claim 12, wherein the host cell is a prokaryotic host cell.

15. An in vitro method of decreasing the intracellular levels of diacylglycerol and increasing intracellular levels phosphatidic acid comprising introducing into a eukaryotic cell a nucleic acid sequence, said nucleic acid comprising the nucleotide sequence of SEQ ID NO: 1.

* * * * *

UNITED STATES PATENT AND TRADEMARK OFFICE
CERTIFICATE OF CORRECTION

PATENT NO. : 5,976,875

DATED : November 2, 1999

INVENTOR(S) :. Stephen M. Prescott et al.

It is certified that error appears in the above-identified patent and that said Letters Patent is hereby corrected as shown below:

ON THE TITLE PAGE

Item [73] Assignee should read --University of Utah Foundation --

Signed and Sealed this

Eighth Day of May, 2001

*Attest:*

NICHOLAS P. GODICI

*Attesting Officer*  *Acting Director of the United States Patent and Trademark Office*